United States Patent
Crowe et al.

(10) Patent No.: US 12,173,054 B2
(45) Date of Patent: Dec. 24, 2024

(54) POLYPEPTIDES

(71) Applicant: Sorriso Pharmaceuticals, Inc., San Diego, CA (US)

(72) Inventors: Scott Crowe, Cambridge (GB); Mike West, Cambridge (GB); Kevin Roberts, Cambridge (GB); Tim Carlton, Cambridge (GB)

(73) Assignee: SORRISO PHARMACEUTICALS, INC., San Diego, CA (US)

( * ) Notice: Subject to any disclaimer, the term of this patent is extended or adjusted under 35 U.S.C. 154(b) by 600 days.

(21) Appl. No.: 16/950,758

(22) Filed: Nov. 17, 2020

(65) Prior Publication Data

US 2021/0317195 A1 Oct. 14, 2021

Related U.S. Application Data

(63) Continuation of application No. 15/717,230, filed on Sep. 27, 2017, now abandoned, which is a continuation of application No. PCT/EP2016/057024, filed on Mar. 31, 2016.

(30) Foreign Application Priority Data

Mar. 31, 2015 (EP) .................... 15162115
Jan. 21, 2016 (EP) .................... 16152320

(51) Int. Cl.
| | |
|---|---|
| *C07K 16/28* | (2006.01) |
| *C07K 16/12* | (2006.01) |
| *C07K 16/24* | (2006.01) |
| *G01N 33/53* | (2006.01) |
| *G01N 33/577* | (2006.01) |
| *A61K 39/00* | (2006.01) |

(52) U.S. Cl.
CPC ........ *C07K 16/1282* (2013.01); *C07K 16/241* (2013.01); *C07K 16/2866* (2013.01); *A61K 2039/542* (2013.01); *C07K 2317/22* (2013.01); *C07K 2317/35* (2013.01); *C07K 2317/54* (2013.01); *C07K 2317/55* (2013.01); *C07K 2317/565* (2013.01); *C07K 2317/567* (2013.01); *C07K 2317/569* (2013.01); *C07K 2317/622* (2013.01); *C07K 2317/92* (2013.01); *C07K 2317/94* (2013.01); *G01N 33/53* (2013.01); *G01N 33/577* (2013.01); *Y02A 50/30* (2018.01)

(58) Field of Classification Search
CPC .............. C07K 16/1282; C07K 16/241; C07K 16/2866; C07K 2317/22; C07K 2317/565; C07K 2317/569; C07K 2317/94; A61K 2039/542
See application file for complete search history.

(56) References Cited

U.S. PATENT DOCUMENTS

| | | |
|---|---|---|
| 3,300,077 A | 1/1967 | David et al. |
| 5,512,459 A | 4/1996 | Wagner et al. |
| 5,780,028 A | 7/1998 | Graham |
| 7,442,159 B1 | 10/2008 | Riechmann et al. |
| 8,399,188 B2 | 3/2013 | Zhao et al. |
| 8,697,654 B2 | 4/2014 | Cheng et al. |
| 9,080,157 B2 | 7/2015 | Convents et al. |
| 9,527,925 B2 | 12/2016 | Gschwind et al. |
| 9,932,412 B2 | 4/2018 | Kim et al. |
| 10,633,438 B2 | 4/2020 | Crowe et al. |
| 10,772,839 B2 | 9/2020 | Crowe et al. |
| 10,980,748 B2 | 4/2021 | Crowe et al. |
| 2004/0041867 A1 | 3/2004 | Lapstun et al. |
| 2005/0147612 A1 | 7/2005 | Yayon et al. |
| 2006/0034833 A1 | 2/2006 | Beirnaert |
| 2006/0034845 A1 | 2/2006 | Silence et al. |
| 2006/0057197 A1 | 3/2006 | Han et al. |
| 2006/0138181 A1 | 6/2006 | Thom et al. |
| 2007/0020267 A1 | 1/2007 | Fuh et al. |
| 2007/0042399 A1 | 2/2007 | Wright et al. |
| 2007/0077249 A1 | 4/2007 | Silence et al. |
| 2007/0178082 A1 | 8/2007 | Silence et al. |
| 2007/0237769 A1 | 10/2007 | Silence et al. |
| 2008/0026820 A1 | 1/2008 | Okada |
| 2008/0031770 A1 | 2/2008 | Heselton et al. |
| 2008/0039761 A1 | 2/2008 | Heaton et al. |
| 2008/0122965 A1 | 5/2008 | Fang |

(Continued)

FOREIGN PATENT DOCUMENTS

| | | |
|---|---|---|
| AU | 2014214850 A1 | 8/2015 |
| CA | 2817265 A1 | 10/2004 |

(Continued)

OTHER PUBLICATIONS

Paul, Fundamental Immunology, 3rd Edition, 1993, pp. 292-295.*

(Continued)

*Primary Examiner* — Hong Sang
(74) *Attorney, Agent, or Firm* — WILSON SONSINI GOODRICH & ROSATI

(57) ABSTRACT

Described herein is a polypeptide comprising an immunoglobulin chain variable domain comprising three complementarity determining regions (CDR1-CDR3) and four framework regions, wherein: (a) at least one lysine residue in CDR1, CDR2 and/or CDR3 has been substituted with at least one histidine residue, and/or (b) at least one arginine residue in CDR1, CDR2 and/or CDR3 has been substituted with at least one histidine residue. The polypeptides of this disclosure possess increased intestinal stability relative to a corresponding polypeptide not having the histidine substitutions.

16 Claims, 18 Drawing Sheets
Specification includes a Sequence Listing.

(56) References Cited

U.S. PATENT DOCUMENTS

| | | |
|---|---|---|
| 2008/0145420 A1 | 6/2008 | Simon |
| 2008/0149143 A1 | 6/2008 | Chou et al. |
| 2008/0260738 A1 | 10/2008 | Moore et al. |
| 2008/0260820 A1 | 10/2008 | Borrelly et al. |
| 2009/0064457 A1 | 3/2009 | Brustle |
| 2009/0064460 A1 | 3/2009 | Tang et al. |
| 2010/0077422 A1 | 3/2010 | Bushinsky |
| 2010/0137213 A1 | 6/2010 | Fernandez et al. |
| 2010/0239682 A1 | 9/2010 | Andremont et al. |
| 2010/0260857 A1 | 10/2010 | Fallon et al. |
| 2011/0028695 A1 | 2/2011 | Revets et al. |
| 2011/0098518 A1 | 4/2011 | Minoux et al. |
| 2011/0109365 A1 | 5/2011 | Mai |
| 2011/0112229 A1 | 5/2011 | Nagaoka et al. |
| 2011/0229476 A1 | 9/2011 | Liu et al. |
| 2012/0130872 A1 | 5/2012 | Baughman et al. |
| 2012/0151199 A1 | 6/2012 | Shriver |
| 2013/0173687 A1 | 7/2013 | Tuchman et al. |
| 2014/0030049 A1 | 1/2014 | Imai et al. |
| 2014/0044730 A1* | 2/2014 | Yancopoulos ............ A61P 3/06 435/7.1 |
| 2014/0141152 A1 | 5/2014 | Sostek et al. |
| 2014/0170212 A1 | 6/2014 | Ortenzi et al. |
| 2014/0186365 A1 | 7/2014 | Robinson et al. |
| 2014/0294826 A1 | 10/2014 | Shoemaker |
| 2014/0377287 A1 | 12/2014 | Govindan et al. |
| 2015/0017183 A1* | 1/2015 | Seidah ............... G01N 33/5735 536/23.53 |
| 2015/0058173 A1 | 2/2015 | Schmeling et al. |
| 2015/0147318 A1* | 5/2015 | Bergeron ............... C07K 16/22 536/23.53 |
| 2015/0176031 A1 | 6/2015 | Streffer |
| 2015/0337035 A1 | 11/2015 | Anderson et al. |
| 2016/0060338 A1 | 3/2016 | Barrett et al. |
| 2016/0156465 A1 | 6/2016 | Vaikuntanathan et al. |
| 2016/0264659 A1 | 9/2016 | Heavner et al. |
| 2017/0002069 A1 | 1/2017 | Crowe et al. |
| 2017/0022271 A1 | 1/2017 | Hoffman et al. |
| 2017/0260266 A1 | 9/2017 | Ahmed et al. |
| 2018/0009881 A1 | 1/2018 | Crowe et al. |
| 2018/0037639 A1 | 2/2018 | Crowe et al. |
| 2018/0100008 A1 | 4/2018 | Crowe et al. |
| 2018/0100009 A1 | 4/2018 | Crowe et al. |
| 2019/0008778 A1 | 1/2019 | Crowe et al. |
| 2019/0040156 A1 | 2/2019 | Demarest et al. |
| 2019/0092855 A1 | 3/2019 | Crowe et al. |
| 2019/0137495 A1 | 5/2019 | Shaked et al. |
| 2019/0307891 A1 | 10/2019 | Crowe et al. |
| 2020/0079844 A1 | 3/2020 | Beirnaert |
| 2020/0317769 A1 | 10/2020 | Crowe et al. |
| 2021/0198345 A1 | 7/2021 | Crowe et al. |
| 2022/0242945 A1 | 8/2022 | Crowe et al. |
| 2022/0332810 A1 | 10/2022 | Crowe et al. |
| 2022/0363769 A1 | 11/2022 | Crowe et al. |
| 2023/0056445 A1 | 2/2023 | Crowe et al. |
| 2023/0143091 A1 | 5/2023 | Crowe et al. |
| 2023/0287098 A1 | 9/2023 | Crowe et al. |

FOREIGN PATENT DOCUMENTS

| | | |
|---|---|---|
| CN | 1809383 A | 7/2006 |
| CN | 101128182 A | 2/2008 |
| CN | 102090373 A | 6/2011 |
| CN | 102388069 A | 3/2012 |
| CN | 102971341 A | 3/2013 |
| CN | 103703129 A | 4/2014 |
| CN | 106715471 A | 5/2017 |
| EP | 2275443 A1 | 1/2011 |
| EP | 2275443 B1 | 12/2015 |
| EP | 2955196 A1 | 12/2015 |
| WO | WO-9102078 A1 | 2/1991 |
| WO | WO-9201047 A1 | 1/1992 |
| WO | WO-9300077 A1 | 1/1993 |
| WO | WO-9404678 A1 | 3/1994 |
| WO | WO-9425591 A1 | 11/1994 |
| WO | WO-9508562 A1 | 3/1995 |
| WO | WO-9634103 A1 | 10/1996 |
| WO | WO-9923221 A2 | 5/1999 |
| WO | WO-0212502 A2 | 2/2002 |
| WO | WO-0248382 A2 | 6/2002 |
| WO | WO-03035694 A2 | 5/2003 |
| WO | WO-2004009776 A2 | 1/2004 |
| WO | WO-2004037205 A2 | 5/2004 |
| WO | WO-2004041862 A2 | 5/2004 |
| WO | WO-2004041863 A2 | 5/2004 |
| WO | WO-2004041865 A2 | 5/2004 |
| WO | WO-2004041867 A2 | 5/2004 |
| WO | WO-2004041862 A3 | 6/2004 |
| WO | WO-2006056306 A2 | 6/2006 |
| WO | WO-2006071877 A2 | 7/2006 |
| WO | WO-2006122786 A2 | 11/2006 |
| WO | WO-2006122787 A1 | 11/2006 |
| WO | WO-2006138181 A2 | 12/2006 |
| WO | WO-2007005955 A2 | 1/2007 |
| WO | WO-2006122786 A3 | 3/2007 |
| WO | WO-2007025977 A2 | 3/2007 |
| WO | WO-2007027714 A2 | 3/2007 |
| WO | WO-2007048022 A2 | 4/2007 |
| WO | WO-2007070948 A1 | 6/2007 |
| WO | WO-2007104529 A2 | 9/2007 |
| WO | WO-2008020079 A1 | 2/2008 |
| WO | WO-2008031770 A2 | 3/2008 |
| WO | WO-2008039761 A2 | 4/2008 |
| WO | WO-2008049897 A1 | 5/2008 |
| WO | WO-2008074840 A2 | 6/2008 |
| WO | WO-2008101985 A2 | 8/2008 |
| WO | WO-2008101985 A3 | 10/2008 |
| WO | WO-2008122965 A2 | 10/2008 |
| WO | WO-2008124170 A2 | 10/2008 |
| WO | WO-2008144753 A2 | 11/2008 |
| WO | WO-2008124170 A3 | 12/2008 |
| WO | WO-2008149143 A2 | 12/2008 |
| WO | WO-2009021754 A2 | 2/2009 |
| WO | WO-2008149143 A3 | 4/2009 |
| WO | WO-2009046168 A1 | 4/2009 |
| WO | WO-2009064457 A2 | 5/2009 |
| WO | WO-2009064460 A2 | 5/2009 |
| WO | WO-2009068627 A2 | 6/2009 |
| WO | WO-2009147248 A2 | 12/2009 |
| WO | WO-2010020811 A1 | 2/2010 |
| WO | WO-2010045506 A2 | 4/2010 |
| WO | WO-2010056550 A1 | 5/2010 |
| WO | WO-2010045506 A3 | 7/2010 |
| WO | WO-2010077422 A2 | 7/2010 |
| WO | WO-2010085643 A1 | 7/2010 |
| WO | WO-2010115998 A2 | 10/2010 |
| WO | WO-2011009365 A1 | 1/2011 |
| WO | WO-2011083175 A1 | 7/2011 |
| WO | WO-2011094259 A2 | 8/2011 |
| WO | WO-2011098518 A2 | 8/2011 |
| WO | WO-2011104687 A1 | 9/2011 |
| WO | WO-2011112229 A2 | 9/2011 |
| WO | WO-2011135026 A1 | 11/2011 |
| WO | WO-2011135040 A1 | 11/2011 |
| WO | WO-2011139269 A1 | 11/2011 |
| WO | WO-2011139629 A2 | 11/2011 |
| WO | WO-2012007880 A2 | 1/2012 |
| WO | WO-2011139629 A3 | 4/2012 |
| WO | WO-2012055030 A1 | 5/2012 |
| WO | WO-2012078878 A2 | 6/2012 |
| WO | WO-2012130872 A2 | 10/2012 |
| WO | WO-2012131053 A1 | 10/2012 |
| WO | WO-2012151199 A1 | 11/2012 |
| WO | WO-2012175741 A2 | 12/2012 |
| WO | WO-2013024059 A2 | 2/2013 |
| WO | WO-2013056984 A1 | 4/2013 |
| WO | WO-2013058833 A1 | 4/2013 |
| WO | WO-2013064701 A2 | 5/2013 |
| WO | WO-2013087857 A2 | 6/2013 |
| WO | WO-2013087874 A1 | 6/2013 |
| WO | WO-2013091103 A1 | 6/2013 |
| WO | WO-2013173687 A1 | 11/2013 |
| WO | WO-2013184871 A1 | 12/2013 |

(56) References Cited

FOREIGN PATENT DOCUMENTS

| | | |
|---|---|---|
| WO | WO-2014030049 A2 | 2/2014 |
| WO | WO-2014058875 A3 | 6/2014 |
| WO | WO-2014141152 A2 | 9/2014 |
| WO | WO-2015009996 A1 | 1/2015 |
| WO | WO-2015058173 A1 | 4/2015 |
| WO | WO-2015065987 A1 | 5/2015 |
| WO | WO-2015100409 A2 | 7/2015 |
| WO | WO-2015144852 A1 | 10/2015 |
| WO | WO-2015176031 A2 | 11/2015 |
| WO | WO-2015189302 A1 | 12/2015 |
| WO | WO-2016065323 A2 | 4/2016 |
| WO | WO-2016103093 A1 | 6/2016 |
| WO | WO-2016156465 A1 | 10/2016 |
| WO | WO-2016156466 A1 | 10/2016 |
| WO | WO-2016162537 A1 | 10/2016 |
| WO | WO-2016202411 A1 | 12/2016 |
| WO | WO-2016202414 A1 | 12/2016 |
| WO | WO-2016202415 A1 | 12/2016 |
| WO | WO-2018060453 A1 | 4/2018 |
| WO | WO-2018104483 A1 | 6/2018 |
| WO | WO-2020254826 A1 | 12/2020 |
| WO | WO-2020254827 A1 | 12/2020 |
| WO | WO-2020254828 A1 | 12/2020 |

OTHER PUBLICATIONS

Rudikoff et al., Proc. Natl. Acad. Sci. USA, 1982, 79(6):1979-1983.*
Colman, Research in Immunology, 145:33-36, 1994.*
Murphy et al., Journal of Immunological Methods, vol. 463, p. 127-133, 2018.*
Muyldermans et al (Annu. Rev. Biochem., 82:775-97, 2013.*
Zabetakis et al., PLOS ONE, 2013, 8(10), 1-7.*
Saerens et al.,J Mol. Biol., 2005, 352: 597-607.*
Vincke et al.,J. Biol. Chem., 2009, 284(5): 3273-3284.*
Julian et al.,Scientific Reports, 2017, 7:45259, pp. 1-13.*
Murtaugh et al.,Protein Science 2011, 20:1619-1631.*
Lu et al.,Frontiers in Immunology, 2018, 9:1012, pp. 1-20.*
Burkovitz et al., FEBS Journal, 2014, 281:306-319.*
Clark et al.,J Immunol, 2006, 177(1):333-340.*
Thomassen et al., Enzyme and Microbial Technology, 30:273-278. (Year: 2002).*
Barata et al. Flip the coin: IL-7 and IL-7R in health and disease. Nat Immunol 20(12):1584-1593 (2019).
Lee et al. Anti-IL-7 receptor-α reverses established type 1 diabetes in nonobese diabetic mice by modulating effector T-cell function. PNAS USA 109(31):12674-12679 (2012).
Marković et al. Modulation of Signaling Mediated by TSLP and IL-7 in Inflammation, Autoimmune Diseases, and Cancer. Front Immunol 11:1557 (2020).
Casset et al. A peptide mimetic of an anti-CD4 monoclonal antibody by rational design. Biochemical and Biophysical Research Communication 307:198-205 (2003).
Chen et al. Enhancement and destruction of antibody function U by somatic mutation: unequal occurrence is controlled by V gene combinatorial associations. The EMBO Journal 14(12):2784-2794 (1995).
MacCallum et al.: Antibody-antigen interactions: contact analysis and binding site topography. J Mol Biol. 262(5):732-745 (1996).
U.S. Appl. No. 16/821,287 Office Action dated Oct. 21, 2022.
U.S. Appl. No. 17/752,710 Office Action dated Nov. 4, 2022.
2005 Drug Bank Data (https://wwwdrugbank.caldrugs/DB00085) for Pancrelipase.
Arbabi-Ghahroudi et al.: Selection and identification of single domain antibody fragments from camel heavy-chain antibodies. FEBS Letters 414(3):521-526 (1997).
Baumgart et al.: Crohn's disease. Lancet 380(9853):1590-1605 (2012).
Biancheri et al. Differential Cleavage of Anti-Tumor Necrosis Factor-Alpha Agents By Matrix Metalloproteinase (MMP)-10 and MMP-12 In Inflammatory Bowel Disease. ECCO, Abstract, 1 page, Dublin (2011).

Bjerkan et al. Multiple Functions of the New Cytokine-Based Antimicrobial Peptide Thymic Stromal Lymphopoietin (TSLP). Pharmaceuticals (Basel) 9(3):E41 (2016).
Blattler et al. New heterobifunctional protein crosslinking reagent that forms an acid-labile link. Biochemistry 24(6):1517-1524 (1985).
Bruno, et al. Basics and recent advances in peptide and protein drug delivery. Ther Deliv. Nov. 2013;4(11):1443-67.
Caldas et al. Humanization of the anti-CD18 antibody 6.7: an unexpected effect of a framework residue in binding to antigen. Mol Immunol. 39(15):941-952 (2003).
Chen et al. Fusion Protein Linkers: Property, Design and Functionality. Adv Drug Deliv Rev 65:1357-1369 (2013). Available online Sep. 29, 2012.
Chomczynski, et al. Single-step method of RNA isolation by acid guanidinium thiocyanate-phenol-chloroform extraction. Anal Biochem. Apr. 1987; 162(1):156-9.
Cianferoni et al. Eosinophilic Esophagitis and Gastroenteritis. Curr Allergy Asthma Rep. 15(9):58 (2015).
Colombel et al. Adalimumab for maintenance of clinical response and remission in patients with Crohn's disease: the CHARM trial. Gastroenterology 132:52-65 (2007).
Coppieters et al.: Formatted anti-tumor necrosis factor alpha VHH proteins derived from camelids show superior potency and targeting to inflamed joints in a murine model of collagen-induced arthritis. Arthritis Rheum 54(6):1856-1866 (2006).
Corren et al. Tezepelumab in Adults with Uncontrolled Asthma. N Engl J Med. 377(10):936-946 (2017).
Crawley et al. Soluble IL-7R alpha (sCD127) inhibits IL-7 activity and is increased in HIV infection. J Immunol. 184(9):4679-4687 (2010).
Croxford et al. IL-23: one cytokine in control of autoimmunity. Eur J Immunol. 42:2263-2273 (2012).
Danese: New therapies for inflammatory bowel disease: from the bench to the bedside. Gut 61(6):918-932 (2012).
Desmet et al. Structural basis of IL-23 antagonism by an Alphabody protein scaffold. Nature Communications 5:5237 (2014).
Desmyter et al.: Neutralization of Human Interleukin 23 by Multivalent Nanobodies Explained by the Structure of Cytokine-Nanobody Complex. Front Immunol. 8:884 (2017).
Dooms. Interleukin-7: Fuel for the autoimmune attack. J Autoimmun. 45:40-48 (2013).
Ebersbach et al.: Affilin-novel binding molecules based on human gamma-B-crystallin, an all beta-sheet protein. J. Molecular Biology 372(1):172-185 (2007).
Eken et al. Interleukin 23 in Crohn's disease. Inflamm Bowel Dis. 20:587-595 (2014).
Ellis et al. Anti-IL-7 receptor α monoclonal antibody (GSK2618960) in healthy subjects—a randomized, double-blind, placebo-controlled study. Br J Clin Pharmacol. 85(2):304-315 (2019).
Fadda et al.: Physiological bicarbonate buffers: stabilisation and use as dissolution media for modified release systems. Int. J. Pharm. 382(1-2):56-60 (2009).
Faisst et al.: Isolation of a fully infectious variant of parvovirus H-1 supplanting the standard strain in human cells. Journal of Virology 69(7):4538-4543 (1995).
Fornasa et al. Dichotomy of short and long thymic stromal lymphopoietin isoforms in inflammatory disorders of the bowel and skin. J Allergy Clin Immunol. 136(2):413-422 (2015).
Fry et al. Interleukin-7: from bench to clinic. Blood 99(11):3892-3904 (2002).
Fry et al. The many faces of IL-7: from lymphopoiesis to peripheral T cell maintenance. J Immunol. 174(11):6571-6576 (2005).
Furfaro et al. IL-23 Blockade for Crohn's disease: next generation of anti-cytokine therapy. Expert Rev Clin Immunol. 13:457-467 (2017).
Garbacz et al.: A dynamic system for the simulation of fasting luminal pH-gradients using hydrogen carbonate buffers for dissolution testing of ionisable compounds. Eur J Pharm Sci. 51:224-231 (2014).
Goldberg et al.: Engineering a targeted delivery platform using Centyrins. Protein Eng Des Sel. 29(12):563-572 (2016).

(56) References Cited

OTHER PUBLICATIONS

Goldberg et al. The unusual suspects—innate lymphoid cells as novel therapeutic targets in IBD. Nat Rev Gastroenterol Hepatol (5):271-283 (2015).
Gomes et al., Comparison of yeasts as hosts for recombinant protein production. Microorganisms 6(2):38 [1-23] (2018).
Goyanes et al.: Gastrointestinal release behaviour of modified-release drug products: dynamic dissolution testing of mesalazine formulations. Int. J. Pharm. 484(1-2):103-108 (2015).
Grabulovski et al. A novel, non-immunogenic Fyn SH3-derived binding protein with tumor vascular targeting properties. J Biol Chem. 282(5):3196-3204 (2007).
Guerra et al.: Management of inflammatory bowel disease in poor responders to infliximab. Clin Exp Gastroenterol 7:359-367 (2014).
Hafler et al. Risk alleles for multiple sclerosis identified by a genomewide study. N Engl J Med. 357(9):851-862 (2007).
Hanauer et al. Human anti-tumor necrosis factor monoclonal antibody (adalimumab) in Crohn's disease: the CLASSIC-I trial. Gastroenterology 130:323-333 (2006).
Hanauer et al, Maintenance infliximab for Crohn's disease: the ACCENT I randomized trial. Lancet 359:1541-1549 (2002).
Harmsen et al.: Effect of a pmr 1 disruption and different signal sequences on the intracellular processing and secretion of Cyamopsis tetragonoloba alpha-galactosidase by *Saccharomyces cerevisiae*. Gene 125(2):115-123 (1993).
Harmsen et al. Properties, production, and applications of camelid single-domain antibody fragments. Appl. Microbiol. Biotechnol. 77:13-22 (2007).
Hashimoto et al.: Effects of signal sequences on the secretion of hen lysozyme by yeast: construction of four secretion cassette vectors. Protein Engineering 11(2):75-77 (1998).
Henikoff et al. Amino acid substitution matrices from protein blocks. PNAS USA 89(22):10915-10919 (1992).
Heninger et al. IL-7 abrogates suppressive activity of human CD4+CD25+FOXP3+ regulatory T cells and allows expansion of alloreactive and autoreactive T cells. J Immunol. 189(12):5649-5658 (2012).
Hoogenboom et al. Multi-subunit proteins on the surface of filamentous phage: methodologies for displaying antibody (Fab) heavy and light chains. Nucleic Acids Res. 19(15):4133-4137 (1991).
Hu et al., A phylogenomic approach to reconstructing the diversification of serine proteases in fungi. J Evol Biol. 17(6):1204-1214 (2004).
Humphreys et al.: Modes of L929 cell death induced by TNF-alpha and other cytotoxic agents. Cytokine 11(10):773-782 (1999).
Huse et al. Generation of a large combinatorial library of the immunoglobulin repertoire in phage lambda. Science 246(4935):1275-1281 (1989).
Hussan et al. A review on recent advances of enteric coating. IOSR J Pharm 2(6):5-11 (2012).
Johnson et al.: Sensitive affimer and antibody based impedimetric label-free assays for c-reactive protein. Analytical Chemistry 84(15):6553-6560 (2012).
Karlin, et al. Applications and statistics for multiple high-scoring segments in molecular sequences. PNAS USA 90:5873-5877 (1993).
Knezevic et al. Quantitation of affinity, avidity, and binding kinetics of protein analytes with a dynamically switchable biosurface. J Am Chem Soc 134(37):15225-15228 (2012).
Kohler et al. Continuous cultures of fused cells secreting antibody of predefined specificity. Nature 256(5517):495-497 (1975).
Koide et al. Monobodies: antibody mimics based on the scaffold of the fibronectin type III domain. Methods in Molecular Biology 352:95-111 (2007).
Krehenbrink et al.: Artificial binding proteins (Affitins) as probes for conformational changes in secretin PulD. J Mol Biol. 383(5):1058-1068 (2008).
Lipovsek: Adnectins: engineered target-binding protein therapeutics. Protein Engineering, Design & Selection 24(1-2):3-9 (2011).
Liu et al. Crucial role of interleukin-7 in T helper type 17 survival and expansion in autoimmune disease. Nat Med. 16(2):191-197 (2010) (retraction in: Nat Med. 2013 19(12):1673).
Liu. Thymic stromal lymphopoietin: master switch for allergic inflammation. J Exp Med 203(2):269-273 (2006).
Lopes et al.: Mechanism of high-copy-number integration of pMIRY-type vectors into the ribosomal DNA of *Saccharomyces cerevisiae*. Gene. 105(1):83-90 (1991).
McGovern et al. The IL23 axis plays a key role in the pathogenesis of IBD. Gut 56:1333-1336 (2007).
Merchant et al.: Predicting the gastrointestinal behaviour of modified-release products: utility of a novel dynamic dissolution test apparatus involving the use of bicarbonate buffers. Int. J. Pharm. 475(1-2):585-591 (2014).
Merchlinksy et al.: Construction of an infectious molecular clone of the autonomous parvovirus minute virus of mice. Journal of Virology 47(1):227-232 (1983).
Michael. The role of digestive enzymes in orally induced immune tolerance. Immunol Invest. 18(9-10):1049-1054 (1989) (Abstract).
Miethe et al.: Production of Single Chain Fragment Variable (scFv) Antibodies in *Escherichia coli* Using the LEX TM Bioreactor. Journal of Biotechnology 163(2):105-111 (2012).
Muszewska et al., Fungal lifestyle reflected in serine protease repertoire. Sci Rep. 7(1):9147 [1-12] (2017).
Nelson et al.: Nonoclonal antibodies. Molecular Pathology 53(3):111-117 (2000).
Nguyen et al. Functional heavy-chain antibodies in Camelidae. Adv Immunol 79:261-296 (2001).
Nixon et al. Engineered protein inhibitors of proteases. Curr Opin Drug Discov Devel. 9(2):261-268 (2006).
Nogi et al.: Nucleotide sequence of the transcriptional initiation region of the yeast GAL7 gene. Nucleic Acid Research 11(24):8555-8568 (1983).
Noti et al. Thymic stromal lymphopoietin-elicited basophil responses promote eosinophilic esophagitis. Nat Med. 19(8):1005-1013 (2013).
Nygren. Alternative binding proteins: affibody binding proteins developed from a small three-helix bundle scaffold. FEBS J. 275(11):2668-2676 (2008).
Ordas et al.: Anti-TNF monoclonal antibodies in inflammatory bowel disease: pharmacokinetics-based dosing paradigms. Clin Pharmacol Ther. 91(4):635-646 (2012).
Ortonne. Recent developments in the understanding of the pathogenesis of psoriasis. British Journal of Dermatology 140(Suppl 54):1-7 (1999).
Patnaik et al. Penicillin fermentation: mechanisms and models for industrial-scale bioreactors. Crit Rev Biotechnol 20:1-15 (2015).
PCT/EP2016/057021 International Search Report and Written Opinion dated Aug. 8, 2016.
PCT/EP2016/057022 International Search Report and Written Opinion dated Jun. 14, 2016.
PCT/EP2016/057032 International Search Report and Written Opinion dated Aug. 4, 2016.
PCT/EP2016/057034 International Search Report and Written Opinion dated Aug. 3, 2016.
PCT/EP2017/057775 International Search Report and Written Opinion dated Jul. 7, 2017.
PCT/GB2020/051495 International Search Report and Written Opinion dated Sep. 30, 2020.
PCT/GB2020/051496 International Search Report and Written Opinion dated Oct. 20, 2020.
PCT/GB2020/051497 International Search Report and Written Opinion dated Sep. 17, 2020.
PCT/MT2017/000001 International Search Report and Written Opinion dated Oct. 20, 2017.
Peters et al. Innate lymphoid cells in inflammatory bowel diseases. Immunol Lett. 172:124-131 (2015).
Rimoldi et al. Intestinal immune homeostasis is regulated by the crosstalk between epithelial cells and dendritic cells. Nat Immunol. 6(5):507-514 (2005).
Rose et al. Identification and biochemical characterization of human plasma soluble IL-7R: lower concentrations in HIV-1-infected patients. J Immunol. 182(12):7389-7397 (2009).

(56) References Cited

OTHER PUBLICATIONS

Sandborn et al. Certolizumab pegol for the treatment of Crohn's disease. N Engl J Med. 357:228-238 (2007).
Schreiber et al. Maintenance therapy with certolizumab pegol for Crohn's disease. N Engl J Med. 357:239-250 (2007).
Shealy et al.: Characterization of golimumab, a human monoclonal antibody specific for human tumor necrosis factor a. MAbs 2(4):428-439 (2010).
Silverman et al., Multivalent avimer proteins evolved by exon shuffling of a family of human receptor domains. Nat. Biotechnol. 23 (12):1556-1561 (2005).
Skerra: Alternative binding proteins: anticalins—harnessing the structural plasticity of the lipocalin ligand pocket to engineer novel binding activities. FEBS J. 275(11):2677-2683 (2008).
Skerra et al. Assembly of a functional Immunoglobulin Fv fragment in *Escherichia coli*. Science 240(4855):1038-1041 (1988).
STIC report (2019).
Suderman et al.: Development of polyol-responsive antibody mimetics for single-step protein purification. Protein Expr Purif. 134:114-124 (2017).
Tal et al.: Interleukin 7 and thymic stromal lymphopoietin: from immunity to leukemia. Cell Mol Life Sci. 71(3):365-378 (2014).
Tanha et al.: Selection by phage display of llama conventional V(H) fragments with heavy chain antibody V(H)H properties. Journal of Immunological Methods 263(1-2):97-109 (2002).
Teng et al. IL-12 and IL-23 cytokines: from discovery to targeted therapies for immune-mediated inflammatory diseases. Nat Med. 21:719-729 (2015).
Teutsch et al. Identification of 11 novel and common single nucleotide polymorphisms in the interleukin-7 receptor-alpha gene and their associations with multiple sclerosis. Eur J Hum Genet. 11(7):509-515 (2003).
Thomassen et al.: Large-scale production of VHH antibody fragments by *Saccharomyces cerevisiae*. Enzyme and Microbial Technology 30(3):273-278 (2002).
Tsilingiri et al. Thymic Stromal Lymphopoietin: To Cut a Long Story Short. Cell Mol Gastroenterol Hepatol. 3(2):174-182 (2017).
Ungar et al.: Optimizing Anti-TNF-a Therapy: Serum Levels of Infliximab and Adalimumab Are Associated With Mucosal Healing in Patients With Inflammatory Bowel Diseases. Clin Gastroenterol Hepatol. 14(4):550-557 (2016).
UniProt Database: Uncharacterized protein. Accession No. B5H131, 2 pages (2008) http://www.uniprot.org/uniprot/B5H131.
U.S. Appl. No. 15/273,353 Office Action dated Aug. 16, 2018.
U.S. Appl. No. 15/273,353 Office Action dated Jan. 23, 2018.
U.S. Appl. No. 15/273,353 Office Action dated Jun. 4, 2019.
U.S. Appl. No. 15/717,174 Office Action dated Apr. 22, 2020.
U.S. Appl. No. 15/717,174 Office Action dated Aug. 8, 2019.
U.S. Appl. No. 15/717,174 Office Action dated Mar. 6, 2019.
U.S. Appl. No. 15/717,174 Office Action dated Sep. 16, 2020.
U.S. Appl. No. 16/140,843 Office Action dated Nov. 26, 2019.
U.S. Appl. No. 16/988,506 Office Action dated Oct. 6, 2020.
Van Schie et al.: The antibody response against human and chimeric anti-TNF therapeutic antibodies primarily targets the TNF binding region. Ann Rheum Dis. 74(1):311-314 (2015).
Vandenbroucke et al. Orally administered L. lactis secreting an anti-TNF nanobody demonstrate efficacy in chronic colitis. Mucosal Immunology 3(1):49-56 (2010).
Vandeventer: Anti-TNF antibody treatment of Crohn's disease. Ann Rheum Dis. 58(Suppl I):1114-1120 (1999).
Verstraete et al. Structure and antagonism of the receptor complex mediated by human TSLP in allergy and asthma. Nat Commun. 8:14937 (2017).
Vetter et al. Emerging oral targeted therapies in inflammatory bowel diseases: opportunities and challenges. Therap Adv Gastroenterol. 10(10):773-790 (2017).
Volkel et al.: Optimized linker sequences for the expression of monomeric and dimeric bispecific single-chain diabodies. Protein Eng. 14(10):815-823 (2001).
Vossenkamper et al.: A CD3-specific antibody reduces cytokine production and alters phosphoprotein profiles in intestinal tissues from patients with inflammatory bowel disease. Gastroenterology 147(1):172-183 (2014).
Walsh. Structural insights into the common y-chain family of cytokines and receptors from the interleukin-7 pathway. Immunol Rev. 250(1):303-316 (2012).
Winkler et al. Changing the antigen binding specificity by single point mutations of an anti-p24 (HIV-1) antibody. J Immunol. 165(8):4505-4514 (2000).
Bendig. Humanization of Rodent Monoclonal Antibodies by CDR Grafting. Methods A Companion To Methods In Enzymology 8:83-93 (1995).
Biancheri et al.: Proteolytic cleavage and loss of function of biologic agents that neutralize tumor necrosis factor in the mucosa of patients with inflammatory bowel disease. Gastroenterology 149(6):1564-1574 (2015).
Binz et al.: Designing repeat proteins: well-expressed, soluble and stable proteins from combinatorial libraries of consensus ankyrin repeat proteins. J. Mol. Biology 332(2):489-503 (2003).
Bruno et al.: Basics and recent advances in peptide and protein drug delivery. Ther Deliv. 4(11):1443-1467 (2013).
Colman et al., Effects of amino acid sequence changes on antibody-antigen interactions, Research in Immunology, 1994; 145(1):33-36.
Crowe et al.: Gastrointestinal Stability and Tissue Penetration of V565: a Novel Orally Administered Anti-TNFa VorabodyTM. Poster from 10th Annual Proteins and Antibodies Congress [1] (2017).
Crowe et al.: Gastrointestinal Stability and Tissue Penetration of V565: A Novel Orally Administered Anti-TNFa VorabodyTm. Vhsquared, Poster from PEGS Europe Protein and Antibody Engineering Summit, Lisbon, Portugal [1] (2017).
Crowe et al.: Oral Delivery of a Novel Engineered Anti TNFa Domain Antibody (VorabodyTM) for the Treatment of Intestinal Bowel Disease. PEGS Europe Protein & Antibody Engineering Summit [1] (2017).
Crowe et al.: Preclinical Assessment of a Novel Anti-TNFa VorabodyTM as an Oral Therapy for Crohn's Disease. 18th International Congress of Mucosal Immunology, Washington D.C. [1] (2017).
Crowe et al.: Preclinical Development of a Novel, Orally-Administered Anti-Tumour Necrosis Factor Domain Antibody for the Treatment of Inflammatory Bowel Disease. Scientific Reports 8:4941 [1-13] (2018).
Deschacht et al.: A novel promiscuous class of camelid single-domain antibody contributes to the antigen-binding repertoire. J. Immmunol 184(10):5696-5704 (2010).
Fields et al. Dual-attribute continuous monitoring of cell proliferation/cytotoxicity. Am Biotechnol Lab 11(4):48-50 (1993).
Frenken et al. Isolation of antigen specific llama VHH antibody fragments and their high level secretion by *Saccharomyces cerevisiae*. J Biotechnol 78(1):11-21 (2000).
Giusti et al. Somatic diversification of S107 from an antiphosphocholine to an anti-DNA autoantibody is due to a single base change in its heavy chain variable region. PNAS USA 84(9):2926-30 (1987).
Griffiths et al.: Shark Variable New Antigen Receptor (VNAR) Single Domain Antibody Fragments: Stability and Diagnostic Applications. Antibodies 2(1):66-81 (2013).
Grundstrom et al.: Oligonucleotide-directed mutagenesis by microscale 'shot-gun' gene synthesis. Nucleic Acids Research 13(9):3305-3316 (1985).
Hamers-Casterman et al. Naturally occurring antibodies devoid of light chains. Nature 363(6428):446-8 (1993).
Harmsen et al.: Selection and Optimization of Proteolytically Stable Llama Single-Domain Antibody Fragments for Oral Immunotherapy. Applied Microbiology and Biotechnology 72(3):544-551 (2006).
Hendrickson et al.: Clinical aspects and pathophysiology of inflammatory bowel disease. Clinical Microbiology Reviews 15(1):79-94 (2002).
Hoefman et al.: Pre-Clinical Intravenous Serum Pharmacokinetics of Albumin Binding and Non-Half-Life Extended Nanobodies(R). Antibodies 4(3):141-156 (2015).
Horwitz et al.: Secretion of functional antibody and Fab fragment from yeast cells. Proc. Natl. Acad. Sci. U.S.A. 85(22):8678-8682 (1988).

(56) References Cited

OTHER PUBLICATIONS

Hussack et al: A V(L) single-domain antibody library shows a high-propensity to yield non-aggregating binders. Protein Eng Des Sel. 25(6):313-318 (2012).
Hussack et al. Chapter 14: Isolation and characterization of Clostridium difficile toxin-specific single-domain antibodies. Methods Mol Biol. 911:211-239 (2012).
Hussack et al. Engineered Single-Domain Antibodies with High Protease Resistance and Thermal Stability. PLOS One. 6(11):e28218 (2011).
Hussack et al.: Neutralization of Clostridium difficile toxin A with single-domain antibodies targeting the cell receptor binding domain. J. Biol. Chem. 286(11):8961-8976 (2011).
Hussack et al.: Protease-resistant single-domain antibodies inhibit Campylobacter jejuni motility. Protein Eng Des Sel. 27(6):191-198 (2014).
Hussack et al.: Single-domain Antibody Inhibitors of Clostridium difficile Toxins. Thesis submitted to the Faculty of Graduate and Postdoctoral Studies, Dept. of Biochemistry, Microbiology and Immunology [1-227] (2011).
Hussack: Single-domain Antibody Inhibitors of Clostridium difficile Toxins. Universite d'Ottawa website [1-3] https://ruor.uottawa.ca/handle/10393/20362 (2013).
Jones et al.: Targeted localized use of therapeutic antibodies: a review of non-systemic, topical and oral applications. Crit Rev Biotechnol 36(3):506-520 (2015).
Kabat et al. Sequences of proteins of immunological interest. NIH Publ. No. 91-3242 1:647-669 (1991).
Kamm et al.: Practical application of anti-TNF therapy for luminal Crohn's disease. Inflammatory Bowel Diseases. 17(11):2366-2391 (2011).
Khantasup, et al. Design and Generation of Humanized Single-chain Fv Derived from Mouse Hybridoma for Potential Targeting Application. Monoclon Antib Immunodiagn Immunother. Dec. 2015;34(6):404-17.
Kim et al.: A Dual Target-directed Agent against Interleukin-6 Receptor and Tumor Necrosis Factor α ameliorates experimental arthritis. Scientific Reports 6:20150 doi: 10.1038/srep20150 [1-12] (2015).
Kim et al.: Antibody light chain variable domains and their biophysically improved versions for human immunotherapy. Mabs. 6(1):219-235 (2014).
Ling et al.: Approaches to DNA Mutagenesis: An Overview. Analytical Biochemistry 254(2):157-178 (1997).
Liu et al.: Targeting TNF-alpha with a tetravalent mini-antibody TNF-TeAb. Biochemical Journal 406(2):237-246 (2007).
McCoy et al.: Neutralisation of HIV-1 cell-cell spread by human and llama antibodies. Retrovirology 11:83 doi:10.1186/s12977-014-0083-y [1-15] (2014).
Molhoj et al. CD19-/CD3-bispecific antibody of the BiTE class is far superior to tandem diabody with respect to redirected tumor cell lysis. Mol Immunol. 44(8):1935-43 (2007).
Muyldermans. Nanobodies: natural single-domain antibodies. Annu Rev Biochem 82:775-797 (2013).
Muyldermans et al. Sequence and structure of VH domain from naturally occurring camel heavy chain immunoglobulins lacking light chains. Protein Engineering 7(9):1129-1133 (1994).
Nambiar, et al. Total synthesis and cloning of a gene coding for the ribonuclease S protein. Science 223(4642):1299-301 (1984).
Nurbhai et al.: Measured and Modelled Data Suggest That Oral Administration of V565, A Novel Domain Antibody to TNF-alpha, Could Be Beneficial in the Treatment of IBD. 13th Congress of ECCO, Vienna, Austria, 1 page (2018).
Nurbhai et al.: Oral Anti-Tumour Necrosis Factor Domain Antibody V565 Provides High Intestinal Concentrations, and Reduces Markers of Inflammation in Ulcerative Colitis Patients. Sci Rep. 9(1):14042 (2019).
Padlan. Anatomy of the Antibody Molecule. Mol Immunol 31(3):169-217 (1994).
Paul. Fundamental Immunology. 3rd Edition, pp. 292-295, Raven Press (1993).
PCT/EP2016/057024 International Search Report and Written Opinion dated Jun. 16, 2016.
Robinson et al.: A Protease-Resistant Oral Domain Antibody to TNFa Delivers High Concentrations of Active Compound in Ileal Fluid of Subjects with an Ileostomy. 25th United European Gastroenterology Week, Barcelona, Spain [1] (2017).
Rose-John: IL-6 trans-signaling via the soluble IL-6 receptor: importance for the pro-inflammatory activities of IL-6. Int. J. Biol. Sci. 8(9):1237-1247 (2012).
Roux et al.: Structural analysis of the nurse shark (new) antigen receptor (NAR): molecular convergence of NAR and unusual mammalian immunoglobulins. PNAS USA 95(20):11804-11809 (1998).
Rudikoff et al. Single amino acid substitution altering antigen-binding Specificity. PNAS USA 79:1979-1983 (1982).
Saerens et al. Identification of a universal VHH framework to graft non-canonical antigen-binding loops of camel single-domain antibodies. J Mol Biol. 352(3):597-607 (2005).
Sakmar et al.: Total synthesis and expression of a gene for the alpha-subunit of bovine rod outer segment guanine nucleotide-binding protein (transducin). Nucleic Acids Research 16(14A):6361-6372 (1988).
Shaji, et al. Protein and Peptide drug delivery: oral approaches. Indian J Pharm Sci. May-Jun. 2008;70(3):269-77.
Siontorou: Nanobodies as novel agents for disease diagnosis and therapy. Int J Nanomedicine 8:4215-4227 (2013).
Unger et al.: Selection of nanobodies that block the enzymatic and cytotoxic activities of the binary Clostridium difficile toxin CDT. Scientific Reports 5:7850 [1-10] (2015).
U.S. Appl. No. 15/717,230 Office Action dated Jan. 21, 2020.
U.S. Appl. No. 15/717,230 Office Action dated May 18, 2020.
U.S. Appl. No. 15/717,230 Office Action dated Sep. 3, 2019.
Verma et al. Modified oligonucleotides: synthesis and strategy for users. Annu Rev Biochem 67:99-134 (1998).
Vincke et al. General strategy to humanize a camelid single-domain antibody and identification of a universal humanized nanobody scaffold. J. Biol. Chem. 284(5):3273-3284 (2009).
Vu et al.: Comparison of llama VH sequences from conventional and heavy chain antibodies. Molecular Immunology 34(16-17):1121-1131 (1997).
Wahlich et al.: Oral Delivery of a Novel Domain Antibody (VorabodyTM) for the Treatment of Chron's Disease. PEGS Europe Protein & Antibody Engineering Summit, Lisbon, Portugal, 1 page (2017).
Ward et al. Binding activities of a repertoire of single immunoglobulin variable domains secreted from *Escherichia coli*. Nature 341(6242):544-546 (1989).
Wells et al. Cassette mutagenesis: an efficient method for generation of multiple mutations at defined sites. Gene 34:315-323 (1985).
West et al.: Predicting intestinal tract luminal concentrations after oral dosing of an anti-TNFa domain antibody engineered for intestinal protease resistance. VHsquared Antibody Engineering & Therapeutics Meeting, San Diego, USA, 1 page (2017).
Yan et al. Construction of a synthetic phage-displayed Nanobody library with CDR3 regions randomized by trinucleotide cassettes for diagnostic applications. Journal of Translational Medicine 12:343 (2014).
Yu et al., Interaction between Bevacizumab and Murine VEGF-A: A Reassessment, Investigative Ophthalmology & Visual Science, 2008, vol. 49 (2), pp. 522-527.
Zabetakis et al. Contributions of the complementarity determining regions to the thermal stability of a single-domain antibody. PLoS One 8(10):e77678 (2013).
U.S. Appl. No. 17/196,498 Office Action dated Dec. 14, 2023.
U.S. Appl. No. 17/196,498 Office Action dated Jul. 19, 2023.
Wallace et al. Immunopathology of inflammatory bowel disease. World J Gastroenterol 20(1):6-21 (2014).
Yusakul et al. Effect of linker length between variable domains of single chain variable fragment antibody against daidzin on its reactivity. Biosci Biotechnol Biochem 80(7):1306-1312 (2016).

(56) References Cited

OTHER PUBLICATIONS

Gustot et al. Profile of soluble cytokine receptors in Crohn's disease. Gut. 54(4):488-495 (2005).

Hosokawa et al. Interleukin-6 and soluble interleukin-6 receptor in the colonic mucosa of inflammatory bowel disease. Journal of Gastroenterology and Hepatology 14(10):987-996 (1999).

Ito et al. A pilot randomized trial of a human anti-interleukin-6 receptor monoclonal antibody in active Crohn's disease. Gastroenterology 126(4):989-996 (2004).

Katoh et al. MAFFT multiple sequence alignment software version 7: improvements in performance and usability. Mol Biol Evol. 30(4):772-780 (2013).

Koh et al. Generation of a family-specific phage library of llama single chain antibody fragments that neutralize HIV-1. Journal of Biological Chemistry 285(25):19116-19124 (2010).

Kusugami et al. Elevation of interleukin-6 in inflammatory bowel disease is macrophage-and epithelial cell-dependent. Dig Dis Sci. 40(5):949-959 (1995).

Merchlinsky et al. Construction of an infectious molecular clone of the autonomous parvovirus minute virus of mice. Journal of Virology 47(1):227-232 (1983).

Mitsuyama et al. Therapeutic strategies for targeting the IL-6/STAT3 cytokine signaling pathway in inflammatory bowel disease. Anticancer Research 27(6A):3749-3756 (2007).

Nelson et al. Monoclonal antibodies. Mol Pathol. 53(3):111-117 (2000).

Reimund et al. Increased production of tumour necrosis factor-alpha interleukin-1 beta, and interleukin-6 by morphologically normal intestinal biopsies from patients with Crohn's disease. Gut 39(5):684-689 (1996).

Reimund et al. Mucosal inflammatory cytokine production by intestinal biopsies in patients with ulcerative colitis and Crohn's disease. Journal of Clinical Immunology 16(3):144-150 (1996).

Reinecker et al., Enhanced secretion of tumor necrosis factor-alpha, IL-6 and IL-1 beta by isolated lamina propia mononuclear cells from patients with ulcerative colitis and Crohn's disease Clin Exp Immunol 94:174-181 (1993).

U.S. Appl. No. 17/196,498 Office Action dated Jun. 7, 2024.

Waetzig et al. Hitting a complex target: an update on interleukin-6 trans-signalling. Expert Opin Ther Targets. 16(2):225-236 (2012).

* cited by examiner

Figure 1

Reduction in vero cell viability in the presence of *C. difficile* toxin

● Toxin
▼ No toxin, medium only

Stability of anti-TNF ICVDs in Mouse small intestinal supernatant after 6 hours incubation

Stability of anti-TNF ICVDs in human faecal and mouse small intestinal supernatant after 16 hour incubation

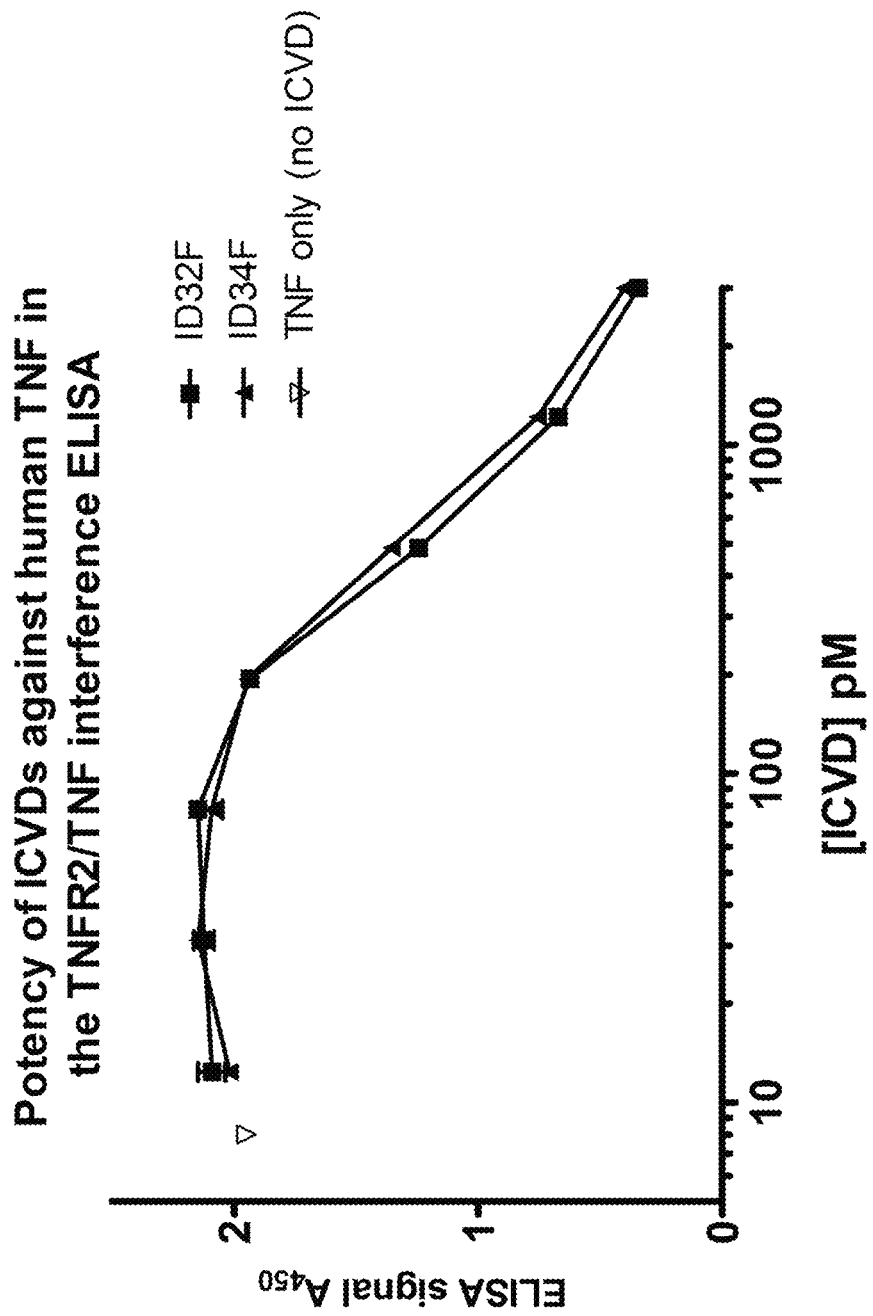

Stability of anti-TNF ICVDs in mouse small intestinal supernatant after 16 hours incubation

Stability of anti-TNF ICVDs in Human faecal supernatant pool 4 after 16 hours incubation

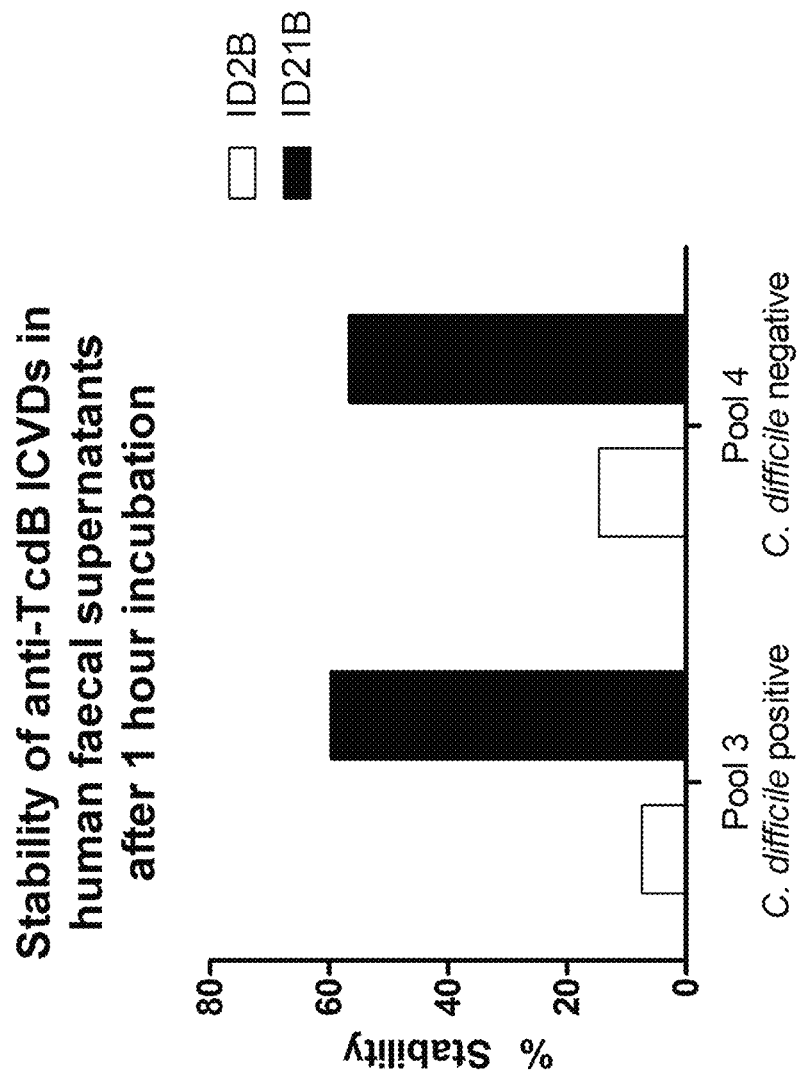

Stability of anti-TcdB bihead ICVDs in *C. difficile* negative human faecal supernatant pool 2 after 4 hour incubation

Figure 12C

**Stability of anti-TcdB bihead ICVDs in *C. difficile* positive human faecal supernatant p 10463 (087) TcdA

Stability of anti-TcdA bihead ICVDs in human faecal supernatants after 1 hour incubation

POLYPEPTIDES

CROSS-REFERENCE TO RELATED APPLICATION(S)

This patent application is a continuation of, and therefore claims priority from, U.S. patent application Ser. No. 15/717,230 entitled POLYPEPTIDES filed Sep. 27, 2017, which is a continuation of, and therefore claims priority from, International Application No. PCT/EP2016/057024 entitled POLYPEPTIDES filed Mar. 31, 2016, which claims priority from EP 15162115.8 filed Mar. 31, 2015 and EP 16152320.4 filed Jan. 21, 2016, the contents each of which are hereby incorporated herein by reference in their entireties.

SEQUENCE LISTING

The instant application contains a Sequence Listing which has been submitting electronically in text file format and is hereby incorporated by reference in its entirety. Said copy, created Jun. 28, 2021, is named "40450-10502_SL.txt" and is 40,319 bytes in size.

FIELD OF THE INVENTION

The present invention relates to polypeptides comprising a region which is capable of binding a target with high affinity, especially those comprising immunoglobulin chain variable domains (ICVD) as well as to constructs comprising said polypeptides and pharmaceutical compositions comprising such polypeptides and constructs. The polypeptides, constructs and pharmaceutical compositions of the invention are all suitable for oral administration. The present invention also relates to methods of increasing the intestinal stability of a polypeptide comprising an immunoglobulin chain variable domain, methods of making a polypeptide comprising an immunoglobulin chain variable domain, and methods which utilise such polypeptides, constructs comprising such polypeptides, nucleic acids encoding such polypeptides, cDNA and vectors comprising nucleic acids encoding such polypeptides, host cells expressing or capable of expressing such polypeptides, pharmaceutical compositions comprising such polypeptides and to uses of such polypeptides.

BACKGROUND OF THE INVENTION

Pharmaceutical research and development is becoming increasingly focussed on biopharmaceuticals such as therapeutic polypeptides, including antibodies. Typically, therapeutic polypeptides are administered either directly or indirectly into the circulation, via a systemic route. However, many therapeutic polypeptides would ideally be delivered via the oral route. Delivering therapeutic polypeptides orally could provide the following advantages: (a) direct targeting to the gastrointestinal tract (GIT) for localised treatment of gastrointestinal diseases (Jones and Martino 2015 *Crit Rev Biotechnol* 20:1-15), (b) the risk of adverse immune reactions could be reduced due to the naturally immuno-tolerant nature of the GIT, ensuring the long-term safety of repeatedly ingesting therapeutic polypeptide materials, (c) without the stringent regulatory requirements of manufacturing injectable therapeutic polypeptides, production costs could be reduced and (d) higher levels of patient acceptance and long term compliance could be achieved (Shaji and Patole *Indian J Pharm Sci* 2008 70(3):269-277).

Many therapeutic polypeptides are, however, unstable in the intestinal tract and therefore the beneficial effect obtained from oral administration is generally limited (Bruno et al 2013 *Ther Deliv* 4(11):1443-1467). Consequently, oral dosage forms used for conventional small molecule drugs have been employed for oral polypeptide delivery. Various strategies currently under investigation include formulation vehicles, use of enzyme inhibitors, absorption enhancers and mucoadhesive polymers (Shaji and Patole, ibid).

Alternative strategies involving modifications to the therapeutic polypeptides themselves have also been employed, such as the introduction of (additional) cysteine bridges. Hussack et al 2011 *PLoS ONE* 6(11):e28218 describe the introduction of additional cysteine bridges into anti-TcdA VHHs. The effectiveness of these additional cysteine bridges on increasing proteolytic stability was highly dependent on the specific protease concerned and in some circumstances these additional cysteine bridges were detrimental to recombinant production levels. Similarly, Kim et al 2014 *mAbs* 6:1 219-235 engineered human VL domains with disulphide bridges, with mixed results.

In theory, one could consider substituting specific amino acids in a therapeutic polypeptide which are believed to be responsible for low intestinal stability of the therapeutic polypeptide, in order to enhance stability in the intestinal tract. However, in the context of immunoglobulin chain variable domains, single substitutions in amino acid sequence may detrimentally impact binding capability. This is particularly relevant to the complementarity determining regions (CDRs) of an immunoglobulin chain variable domain, which are responsible for binding target antigen. For example, regarding in particular CDR3 of a VHH, it is known that " . . . inasmuch as the CDR3 amino acids either are in direct contact with the antigen or maintain and influence the conformation of the CDR3 amino acids that directly contact the antigen, the CDR3 amino acids responsible for reduced stability cannot be replaced without serious loss of affinity." (Muyldermans *Annu Rev Biochem* 2013 82:775-797). This view is reinforced by, for example, the finding that substitutions to a VHH targeting *C. jejuni* flagella, including in particular an R to G substitution in CDR2, caused a large decrease in binding capability of the VHH (approaching control) (Hussack et al 2014 *Protein Engineering, Design & Selection* 27(6):191-198).

There is a long-felt need therefore for polypeptides which have increased intestinal stability, and for methods to increase the intestinal stability of such polypeptides.

Polypeptides of the present invention may, in at least some embodiments, have one or more of the following advantages compared to substances of the prior art:
(i) increased suitability for oral administration;
(ii) increased suitability for local delivery to the intestinal tract following oral administration;
(iii) increased intestinal stability whilst substantially maintaining binding affinity and/or potency;
(iv) increased stability in a model of the intestinal tract such as the Standard Trypsin Intestinal Tract Model, the Standard Mouse Small Intestinal Supernatant Intestinal Tract Model or the Standard Human Faecal Supernatant Intestinal Tract Model, whilst maintaining binding affinity and/or potency;
(v) increased stability in the presence of proteases, for example (a) in the presence of proteases found in the small and/or large intestine and/or IBD inflammatory proteases, for example trypsin, chymotrypsin, MMPs, cathepsin, enteropeptidase, host inflammatory proteases and/or (b) in the presence of proteases from gut commensal microflora and/or pathogenic bacteria, actively secreted and/or released by lysis of microbial cells found in the small and/or large intestine;

(vi) increased stability when expressed in a heterologous host such as a yeast such as a yeast belonging to the genera *Aspergillus, Saccharomyces, Kluyveromyces, Hansenula* or *Pichia* (by virtue of increased resistance to yeast proteases);

(vii) reduced risk of adverse immune reactions;

(viii) reduced production costs;

(ix) improved treatment and/or prevention of intestinal infection or autoimmune and/or inflammatory diseases;

(x) improved patient acceptance and long term compliance;

(xi) improved yield during recombinant production;

(xii) improved bioactivity and/or biodistribution;

(xiii) reduced required dosage;

(xiv) suitability for, and improved properties for, use in a pharmaceutical;

(xv) suitability for, and improved properties for, use in a functional food.

SUMMARY OF THE INVENTION

The present inventors have produced surprisingly advantageous polypeptides comprising immunoglobulin chain variable domains, suitable for oral administration. These polypeptides are particularly advantageous due to their increased intestinal stability (i.e. increased stability in the intestinal tract). It may be expected that these polypeptides have particular utility in the prevention or treatment of diseases of the gastrointestinal tract such as autoimmune and/or inflammatory disease such as inflammatory bowel disease, or in the prevention or treatment of infection from intestinal tract resident pathogenic microbe. Also provided are methods of increasing the intestinal stability of a polypeptide comprising an immunoglobulin chain variable domain and methods of making a polypeptide comprising an immunoglobulin chain variable domain having increased stability.

Accordingly, the present invention provides a polypeptide comprising an immunoglobulin chain variable domain comprising three complementarity determining regions (CDR1-CDR3) and four framework regions, wherein: (a) at least one lysine residue in CDR1, CDR2 and/or CDR3 has been substituted with at least one histidine residue, and/or (b) at least one arginine residue in CDR1, CDR2 and/or CDR3 has been substituted with at least one histidine residue; wherein the polypeptide has increased intestinal stability relative to a corresponding polypeptide not having said histidine substitutions.

Also provided is a method of increasing the intestinal stability of a polypeptide comprising an immunoglobulin chain variable domain, wherein the immunoglobulin chain variable domain comprises three complementarity determining regions (CDR1-CDR3) and four framework regions, wherein the method comprises the step of substituting: (a) at least one lysine residue in CDR1, CDR2 and/or CDR3 with at least one histidine residue, and/or (b) at least one arginine residue in CDR1, CDR2 and/or CDR3 with at least one histidine residue.

Also provided is a method of making a polypeptide comprising an immunoglobulin chain variable domain, wherein the immunoglobulin chain variable domain comprises three complementarity determining regions (CDR1-CDR3) and four framework regions, wherein the method comprises the step of substituting: (a) at least one lysine residue in CDR1, CDR2 and/or CDR3 with at least one histidine residue, and/or (b) at least one arginine residue in CDR1, CDR2 and/or CDR3 with at least one histidine residue wherein the polypeptide has increased intestinal stability relative to a corresponding polypeptide not having said histidine substitutions.

Also provided is a polypeptide comprising a region which is capable of binding a target with high affinity wherein: (a) at least one lysine residue in the region has been substituted with at least one histidine residue, and/or (b) at least one arginine residue in the region has been substituted with at least one histidine residue; wherein the polypeptide has increased intestinal stability relative to a corresponding polypeptide not having said histidine substitutions.

DESCRIPTION OF THE FIGURES

FIG. 1—Example TcdA dose-response curve on Vero cells

DESCRIPTION OF THE SEQUENCES

Figure 2A:
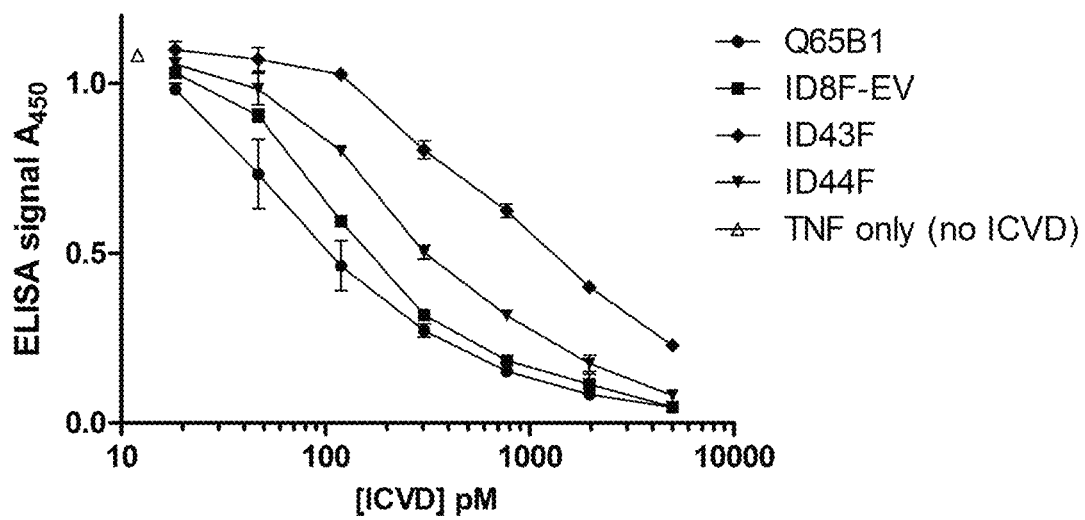
FIG. 2A—Potency of anti-TNF ICVDs Q65B1, ID8F-EV, ID43F and ID44F (Experiment 1) against human TNF in the TNFR2/TNF interference ELISA FIG. 2B—Potency of anti-TNF ICVDs Q65B1 and ID8F-EV (Experiment 2) against human TNF in the TNFR2/TNF interference ELISA FIG. 3A—Stability of anti-TNF ICVDs Q65B1, ID8F-EV, ID43F and ID44F in mouse small intestinal supernatant after 6 hours incubation FIG. 3B—Stability of anti-TNF ICVDs Q65B1 and ID8F-EV in human faecal and mouse small intestinal supernatant after 16 hour incubation FIG. 4—Potency of ICVDs ID32F and ID34F against human TNF in the TNFR2/TNF interference ELISA FIG. 5A—Stability of anti-TNF ICVDs ID32F and ID34F in mouse small intestinal supernatant after 16 hours incubation FIG. 5B—Stability of anti-TNF ICVDs ID32F and ID34F in human faecal supernatant pool 4 after 16 hours incubation FIG. 6A—TcdB 027 neutralisation by ID45B-ID50B in the Vero cell cytotoxicity assay FIG. 6B—Stability of anti-TcdB ICVDs ID45B-ID50B in human faecal supernatant pool 4 after 30 minutes incubation, analysed by western blot FIG. 7—TcdB 027 neutralisation by ID2B, ID20B, ID21B and ID22B in the Vero cell cytotoxicity assay FIG. 8A—ID2B trypsin assay—stained polyacrylamide gel FIG. 8B—ID20B and ID21B trypsin assays—stained polyacrylamide gels FIG. 8C—ID22B trypsin assay—stained polyacrylamide gel FIG. 9—Stability of anti-TcdB ICVDs ID2B and ID21B in human faecal supernatants after 1 hour incubation FIG. 10A—TcdB 027 neutralisation by ID1B, ID24B, ID25B and ID27B in the Vero cell cytotoxicity assay FIG. 10B—Stability of anti-TcdB ICVDs ID1B, ID24B, ID25B and ID27B in human faecal supernatant pool 2 after 1 hour incubation FIG. 11A—ID1B trypsin assay—stained polyacrylamide gel FIG. 11B—ID24B and 25B trypsin assays—stained polyacrylamide gels FIG. 11C—ID27B trypsin assay—stained polyacrylamide gel FIG. 12A—TcdB 017 neutralisation by bihead constructs ID41B and ID43B in the Vero cell cytotoxicity assay FIG. 12B—Stability of anti-TcdB bihead constructs ID41B and ID43B in *C. difficile* negative human faecal supernatant pool 2 after 4 hour incubation (three repeat ELISAs)

SEQ ID NO: 1—Polypeptide sequence of anti-TNF-alpha ICVD Q65B1
SEQ ID NO: 2—Polypeptide sequence of anti-TNF-alpha ICVD ID8F-EV (ID32F)
SEQ ID NO: 3—Polypeptide sequence of anti-TNF-alpha ICVD ID43F
SEQ ID NO: 4—Polypeptide sequence of anti-TNF-alpha ICVD ID44F
SEQ ID NO: 5—Polypeptide sequence of anti-TNF-alpha ICVD ID34F
SEQ ID NO: 6—Polypeptide sequence of anti-TcdB ICVD B10F1
SEQ ID NO: 7—Polypeptide sequence of anti-TcdB ICVD Q31B1
SEQ ID NO: 8—Polypeptide sequence of anti-TcdB ICVD ID1B
SEQ ID NO: 9—Polypeptide sequence of anti-TcdB ICVD ID2B
SEQ ID NO: 10—Polypeptide sequence of anti-TcdB ICVD ID20B
SEQ ID NO: 11—Polypeptide sequence of anti-TcdB ICVD ID21B
SEQ ID NO: 12—Polypeptide sequence of anti-TcdB ICVD ID22B
SEQ ID NO: 13—Polypeptide sequence of anti-TcdB ICVD ID24B
SEQ ID NO: 14—Polypeptide sequence of anti-TcdB ICVD ID25B
SEQ ID NO: 15—Polypeptide sequence of anti-TcdB ICVD ID27B
SEQ ID NO: 16—Polypeptide sequence of anti-TcdB construct ID41B
SEQ ID NO: 17—Polypeptide sequence of anti-TcdB construct ID43B
SEQ ID NO: 18—Polypeptide sequence of anti-TcdB ICVD ID45B
SEQ ID NO: 19—Polypeptide sequence of anti-TcdB ICVD ID46B
SEQ ID NO: 20—Polypeptide sequence of anti-TcdB ICVD ID47B
SEQ ID NO: 21—Polypeptide sequence of anti-TcdB ICVD ID48B
SEQ ID NO: 22—Polypeptide sequence of anti-TcdB ICVD ID49B
SEQ ID NO: 23—Polypeptide sequence of anti-TcdB ICVD ID50B
SEQ ID NO: 24—Polypeptide sequence of anti-TcdA construct ID17A
SEQ ID NO: 25—Polypeptide sequence of anti-TcdA construct ID29A
SEQ ID NO: 26—Example CDR A
SEQ ID NO: 27—First third of Example CDR A
SEQ ID NO: 28—Second third of Example CDR A
SEQ ID NO: 29—Third third of Example CDR A
SEQ ID NO: 30—Example CDR B
SEQ ID NO: 31—Second third of Example CDR B
SEQ ID NO: 32—Polypeptide sequence of anti-IL-6R ICVD 7F6
SEQ ID NO: 33—Polypeptide sequence of anti-IL-6R ICVD ID-3V
SEQ ID NO: 34—Polypeptide sequence of anti-IL-6R ICVD 5G9
SEQ ID NO: 35—Polypeptide sequence of anti-IL-6R ICVD ID-54V

DETAILED DESCRIPTION OF THE INVENTION

Polypeptides, Antigen-Binding Polypeptides, Antibodies and Antibody Fragments Including Immunoglobulin Chain Variable Domains (ICVD) Such as the VH and VHH Polypeptides are organic polymers consisting of a number of amino acid residues bonded together in a chain. As used herein, 'polypeptide' is used interchangeably with 'protein' and 'peptide'. Polypeptides are said to be antigen-binding when they contain one or more stretches of amino acid residues which form an antigen-binding site, capable of binding to an epitope on a target antigen with an affinity (suitably expressed as a Kd value, a Ka value, a kon-rate and/or a koff-rate, as further described herein). Antigen-binding polypeptides include polypeptides such as antibodies, antibodies modified to comprise additional binding regions, and antigen-binding fragments.

A polypeptide may comprise a region which is capable of binding a target with high affinity (suitably expressed as a Kd value, a Ka value, a $k_{on}$-rate and/or a $K_{off}$-rate, as further described herein). Such polypeptides include DARPins (Binz et al. Journal of Molecular Biology 332(2):489-503), Affimers™, Fynomers™, Centyrins, Nanofitins® and cyclic peptides.

A conventional antibody or immunoglobulin (Ig) is a protein comprising four polypeptide chains: two heavy (H) chains and two light (L) chains. Each chain is divided into a constant region and a variable domain. The heavy chain variable domains are abbreviated herein as VHC, and the light (L) chain variable domains are abbreviated herein as VLC. These domains, domains related thereto and domains derived therefrom, are referred to herein as immunoglobulin chain variable domains. The VHC and VLC domains can be further subdivided into regions of hypervariability, termed "complementarity determining regions" ("CDRs"), interspersed with regions that are more conserved, termed "framework regions" ("FRs"). The framework and complementarity determining regions have been precisely defined (Kabat et al 1991 Sequences of Proteins of Immunological Interest, *Fifth Edition U.S. Department of Health and Human Services*, NIH Publication Number 91-3242, herein incorporated by reference in its entirety). In a conventional antibody, each VHC and VLC is composed of three CDRs and four FRs, arranged from amino-terminus to carboxy-terminus in the following order: FR1, CDR1, FR2, CDR2, FR3, CDR3, FR4. The conventional antibody tetramer of two heavy immunoglobulin chains and two light immunoglobulin chains is formed with the heavy and the light immunoglobulin chains inter-connected by e.g. disulfide bonds, and the heavy chains similarity connected. The heavy chain constant region includes three domains, CH1, CH2 and CH3. The light chain constant region is comprised of one domain, CL. The variable domain of the heavy chains and the variable domain of the light chains are binding domains that interact with an antigen. The constant regions of the antibodies typically mediate the binding of the antibody to host tissues or factors, including various cells of the immune system (e.g. effector cells) and the first component (C1q) of the classical complement system. The term antibody includes immunoglobulins of types IgA, IgG, IgE, IgD, IgM (as well as subtypes thereof), wherein the light chains of the immunoglobulin may be kappa or lambda types. The overall structure of immunoglobulin-gamma (IgG) antibodies assembled from two identical heavy (H)-chain and two identical light (L)-chain polypeptides is well established and highly conserved in mammals (Padlan 1994 *Mol Immunol* 31:169-217).

An exception to conventional antibody structure is found in sera of Camelidae. In addition to conventional antibodies, these sera possess special IgG antibodies. These IgG antibodies, known as heavy-chain antibodies (HCAbs), are devoid of the L chain polypeptide and lack the first constant domain (CH1). At its N-terminal region, the H chain of the homodimeric protein contains a dedicated immunoglobulin chain variable domain, referred to as the VHH, which serves to associate with its cognate antigen (Muyldermans 2013 *Annu Rev Biochem* 82:775-797, Hamers-Casterman et al 1993 *Nature* 363(6428):446-448, Muyldermans et al 1994 *Protein Eng* 7(9):1129-1135, herein incorporated by reference in their entirety).

The total number of amino acid residues in a VHH or VH may be in the region of 105-140, is suitably 108-130, and is most suitably 110-125.

An antigen-binding fragment (or "antibody fragment", "immunoglobulin fragment" or "antigen-binding polypeptide") as used herein refers to a portion of an antibody that specifically binds to a target (e.g. a molecule in which one or more immunoglobulin chains is not full length, but which specifically binds to a target). An antigen-binding fragment comprises an immunoglobulin chain variable domain. Examples of binding fragments encompassed within the term antigen-binding fragment include:
  (i) a Fab fragment (a monovalent fragment consisting of the VLC, VHC, CL and CH1 domains);
  (ii) a F(ab')2 fragment (a bivalent fragment comprising two Fab fragments linked by a disulfide bridge at the hinge region);
  (iii) a Fd fragment (consisting of the VHC and CH1 domains);
  (iv) a Fv fragment (consisting of the VLC and VHC domains of a single arm of an antibody);
  (v) an scFv fragment (consisting of VLC and VHC domains joined, using recombinant methods, by a synthetic linker that enables them to be made as a single protein chain in which the VLC and VHC regions pair to form monovalent molecules);
  (vi) a VH (an immunoglobulin chain variable domain consisting of a VHC domain (Ward et al *Nature* 1989 341:544-546);
  (vii) a VL (an immunoglobulin chain variable domain consisting of a VLC domain);
  (viii) a V-NAR (an immunoglobulin chain variable domain consisting of a VHC domain from chondrichthyes IgNAR (Roux et al 1998 *Proc Natl Acad Sci USA* 95:11804-11809 and Griffiths et al 2013 *Antibodies* 2:66-81, herein incorporated by reference in their entirety)
  (ix) a VHH.

Suitably the polypeptide of the invention consists of an immunoglobulin chain variable domain. Suitably the polypeptide of the invention is an antibody, a modified antibody containing additional antibody binding regions or an antibody fragment such as a VHH, a VH, a VL, a V-NAR, scFv, a Fab fragment or a F(ab')2 fragment Polypeptides of the invention may for example be obtained by preparing a nucleic acid encoding the polypeptide using techniques for nucleic acid synthesis, followed by expression of the nucleic acid thus obtained (as detailed further herein).

The examples provided herein relate to immunoglobulin chain variable domains per se. The principles of the invention disclosed herein are, however, equally applicable to at least any polypeptide comprising an immunoglobulin chain variable domain, such as antibodies and antibody fragments. For example, the immunoglobulin chain variable domains disclosed herein may be incorporated into a polypeptide such as a full length antibody. Such an approach is demonstrated by McCoy et al *Retrovirology* 2014 11:83, who provide an anti-HIV VHH engineered as a fusion with a human Fc region (including hinge, CH2 and CH3 domains), expressed as a dimer construct.

Polypeptide and Polynucleotide Sequences

As used herein, numbering of polypeptide sequences and definitions of CDRs and FRs are as defined according to the Kabat system (Kabat et al, ibid). A "corresponding" amino acid residue between a first and second polypeptide sequence is an amino acid residue in a first sequence which shares the same position according to the Kabat system with an amino acid residue in a second sequence, whilst the amino acid residue in the second sequence may differ in identity from the first. Suitably corresponding residues will share the same number (and letter) if the framework and CDRs are the same length according to Kabat definition. Alignment can be achieved manually or by using, for example, a known computer algorithm for sequence alignment such as NCBI BLAST v2.0 (BLASTP or BLASTN) using standard settings. Two or more polypeptides are 'corresponding' if they share the same sequence but for any changes specified.

The Kabat Numbering System Applied to ICVD Q65B1

| Residue # | Q65B1 | Kabat numbering | Region |
|---|---|---|---|
| 1 | E | H1 | FR1 |
| 2 | V | H2 | FR1 |
| 3 | Q | H3 | FR1 |
| 4 | L | H4 | FR1 |
| 5 | V | H5 | FR1 |
| 6 | E | H6 | FR1 |
| 7 | S | H7 | FR1 |
| 8 | G | H8 | FR1 |
| 9 | G | H9 | FR1 |
| 10 | G | H10 | FR1 |
| 11 | L | H11 | FR1 |
| 12 | V | H12 | FR1 |
| 13 | Q | H13 | FR1 |
| 14 | P | H14 | FR1 |
| 15 | G | H15 | FR1 |
| 16 | G | H16 | FR1 |
| 17 | S | H17 | FR1 |
| 18 | L | H18 | FR1 |
| 19 | K | H19 | FR1 |
| 20 | L | H20 | FR1 |
| 21 | S | H21 | FR1 |
| 22 | C | H22 | FR1 |
| 23 | A | H23 | FR1 |
| 24 | A | H24 | FR1 |
| 25 | S | H25 | FR1 |
| 26 | G | H26 | CDR1 |
| 27 | F | H27 | CDR1 |
| 28 | D | H28 | CDR1 |
| 29 | F | H29 | CDR1 |
| 30 | S | H30 | CDR1 |
| 31 | S | H31 | CDR1 |
| 32 | H | H32 | CDR1 |
| 33 | W | H33 | CDR1 |
| 34 | M | H34 | CDR1 |
| 35 | Y | H35 | CDR1 |
| 36 | W | H36 | FR2 |
| 37 | V | H37 | FR2 |
| 38 | R | H38 | FR2 |
| 39 | Q | H39 | FR2 |
| 40 | A | H40 | FR2 |
| 41 | P | H41 | FR2 |
| 42 | G | H42 | FR2 |
| 43 | K | H43 | FR2 |
| 44 | E | H44 | FR2 |
| 45 | L | H45 | FR2 |
| 46 | E | H46 | FR2 |
| 47 | W | H47 | FR2 |
| 48 | L | H48 | FR2 |
| 49 | S | H49 | CDR2 |
| 50 | E | H50 | CDR2 |
| 51 | I | H51 | CDR2 |
| 52 | N | H52 | CDR2 |
| 53 | T | H52A | CDR2 |
| 54 | N | H53 | CDR2 |
| 55 | G | H54 | CDR2 |
| 56 | L | H55 | CDR2 |
| 57 | I | H56 | CDR2 |
| 58 | T | H57 | CDR2 |
| 59 | K | H58 | CDR2 |
| 60 | Y | H59 | CDR2 |
| 61 | G | H60 | CDR2 |
| 62 | D | H61 | CDR2 |
| 63 | S | H62 | CDR2 |
| 64 | V | H63 | CDR2 |
| 65 | K | H64 | CDR2 |
| 66 | G | H65 | FR3 |
| 67 | R | H66 | FR3 |
| 68 | F | H67 | FR3 |
| 69 | T | H68 | FR3 |
| 70 | V | H69 | FR3 |
| 71 | S | H70 | FR3 |
| 72 | R | H71 | FR3 |
| 73 | N | H72 | FR3 |
| 74 | N | H73 | FR3 |
| 75 | A | H74 | FR3 |
| 76 | A | H75 | FR3 |
| 77 | N | H76 | FR3 |
| 78 | K | H77 | FR3 |
| 79 | M | H78 | FR3 |
| 80 | Y | H79 | FR3 |
| 81 | L | H80 | FR3 |
| 82 | E | H81 | FR3 |
| 83 | L | H82 | FR3 |
| 84 | T | H82A | FR3 |
| 85 | R | H82B | FR3 |
| 86 | L | H82C | FR3 |
| 87 | E | H83 | FR3 |
| 88 | P | H84 | FR3 |
| 89 | E | H85 | FR3 |
| 90 | D | H86 | FR3 |
| 91 | T | H87 | FR3 |
| 92 | A | H88 | FR3 |
| 93 | L | H89 | FR3 |
| 94 | Y | H90 | FR3 |
| 95 | Y | H91 | FR3 |
| 96 | C | H92 | FR3 |
| 97 | A | H93 | FR3 |
| 98 | R | H94 | FR3 |
| 99 | N | H95 | CDR3 |
| 100 | Q | H96 | CDR3 |
| 101 | K | H97 | CDR3 |
| 102 | G | H98 | CDR3 |
| 103 | L | H101 | CDR3 |
| 104 | N | H102 | CDR3 |
| 105 | K | H103 | FR4 |
| 106 | G | H104 | FR4 |
| 107 | Q | H105 | FR4 |
| 108 | G | H106 | FR4 |
| 109 | T | H107 | FR4 |
| 110 | Q | H108 | FR4 |
| 111 | V | H109 | FR4 |
| 112 | T | H110 | FR4 |
| 113 | V | H111 | FR4 |
| 114 | S | H112 | FR4 |
| 115 | S | H113 | FR4 |

The Kabat Characterisation System Applied to ICVD and
ICVD Construct Sequences

CDRs 1, 2 and 3 are the first, second and third underlined portions of each ICVD or construct. FRs 1, 2, 3 and 4 are the first, second, third and fourth portions joining the CDRs of each ICVD. The linker is also shown in the case of biheads. Substitutions relative to unmodified comparators are shown italicised and emboldened. Substitution descriptions in brackets are referred-to by N-to-C-terminal numbering (as opposed to Kabat numbering).

Anti-TNF-alpha (SEQ ID NO: 1)
Q65B1
EVQLVESGGGLVQPGGSLKLSCAASGFDFS SHWMY WVRQAPGKELEWLS EINTNGLITKYGDSVKG RFTVSRNNAANKMYLELTRLEPEDTALYYCAR NQKGLN KGQGTQVTVSS (SEQ ID NO: 2)
ID32F/ID8F-EV
EVQLVESGGGLVQPGGSLKLSCAASGFDFS SHWMY WVRQAPGKELEWLS EINTNGLITHYGDSVKG RFTVSRNNAANKMYLELTRLEPEDTALYYCAR NQKGLN KGQGTQVTVSS (SEQ ID NO: 3)
ID43F
EVQLVESGGGLVQPGGSLKLSCAASGFDFS SHWMY WVRQAPGKELEWLS EINTNGLITAYGDSVKG RFTVSRNNAANKMYLELTRLEPEDTALYYCAR NQKGLN KGQGTQVTVSS (SEQ ID NO: 4)
ID44F
EVQLVESGGGLVQPGGSLKLSCAASGFDFS SHWMY WVRQAPGKELEWLS EINTNGLITQYGDSVKG RFTVSRNNAANKMYLELTRLEPEDTALYYCAR NQKGLN KGQGTQVTVSS (SEQ ID NO: 5)
ID34F
EVQLVESGGGLVQPGGSLKLSCAASGFDFS SHWMY WVRQAPGKELEWLS EINTNGLITHYGDSVKG RFTVSRNNAANKMYLELTRLEPEDTALYYCAR NQHGLN KGQGTQVTVSS

Anti-TcdB

B10F1 (unmodified) (SEQ ID NO: 6)
QVQLQESGGGLVQAGGSLRLSCAASGRTFS SYTMG WFRQAPGKEREFVA AINGSGGNRISADSVKG RFTISRDNAKNTVVLQLNSLKPEDTAVYYCAA SLTYYGRSARYDY WGQGTQVTVSS Q31B1 (unmodified) (SEQ ID NO: 7)
EVQLVESGGGLVQAGDSLRLSCAASGRTLS SYTMG WFRQAPEKEREFVA GSSRDGRTNYYANSVKG RFTISRDNAKNTVVLQMNSLKPEDTAVYYCAA HTTSGVPVRERSYAY WGQGTQVTVSS ID1B (B10F1 with Q1D and R27A) (SEQ ID NO: 8)
*D*VQLQESGGGLVQAGGSLRLSCAASGATFS SYMG WFRQAPGKEREFVA AINGSGGNRISADSVKG RFTISRDNAKNTVVLQLNSLKPEDTAVYYCAA SLTYYGRSARYDY WGQGTQVTVSS ID2B (Q31B1 with E1D, V5Q and R27A) (SEQ ID NO: 9)
*D*VQL*Q*ESGGGLVQAGDSLRLSCAASGATLS SYTMG WFRQAPEKEREFVA GSSRDGRTNYYANSVKG RFTISRDNAKNTVVLQMNSLKPEDTAVYYCAA HTTSGVPVRERSYAY WGQGTQVTVSS ID20B (ID2B with M34I, R53H, R56H) (SEQ ID NO: 10)
DVQLQESGGGLVQAGDSLRLSCAASGATLS SYT*I*G WFRQAPEKEREFVA GSS*H*DGRTNYYANSVKG RFTISRDNAKNTVVLQMNSLKPEDTAVYYCAA HTTSGVPVRERSYAY WGQGTQVTVSS ID21B (ID2B with M34I, R107H) (SEQ ID NO: 11)
DVQLQESGGGLVQAGDSLRLSCAASGATLS SYT*I*G WFRQAPEKEREFVA GSSRDGRTNYYANSVKG RFTISRDNAKNTVVLQMNSLKPEDTAVYYCAA HTTSGVPV*H*ERSYAY WGQGTQVTVSS ID22B (ID2B with M34I, R109H) (SEQ ID NO: 12)
DVQLQESGGGLVQAGDSLRLSCAASGATLS SYT*I*G WFRQAPEKEREFVA GSSRDGRTNYYANSVKG RFTISRDNAKNTVVLQMNSLKPEDTAVYYCAA HTTSGVPVR*E*RSYAY WGQGTQVTVSS -continued CDRs 1, 2 and 3 are the first, second and third underlined portions of each ICVD or construct. FRs 1, 2, 3 and 4 are the first, second, third and fourth portions joining the CDRs of each ICVD. The linker is also shown in the case of biheads. Substitutions relative to unmodified comparators are shown italicised and emboldened. Substitution descriptions in brackets are referred-to by N-to-C-terminal numbering (as opposed to Kabat numbering).

ID24B (ID1B with M34I, R58H) (SEQ ID NO: 13)
DVQLQESGGGLVQAGGSLRLSCAASGATFS SYYIG WFRQAPGKEREFVA AINGSGGNHISADSVKG RFTISRDNAKNTVVLQLNSLKPEDTAVYYCAA SLTYYGRSARYDY
WGQGTQVTVSS ID25B (ID1B with M34I, R108H) (SEQ ID NO: 14)
DVQLQESGGGLVQAGGSLRLSCAASGATFS SYYIG WFRQAPGKEREFVA AINGSGGNRISADSVKG RFTISRDNAKNTVVLQLNSLKPEDTAVYYCAA SLTYYGRSAHYDY
WGQGTQVTVSS ID27B (ID1B with M34I, R105H) (SEQ ID NO: 15)
DVQLQESGGGLVQAGGSLRLSCAASGATFS SYYIG WFRQAPGKEREFVA AINGSGGNRISADSVKG RFTISRDNAKNTVVLQLNSLKPEDTAVYYCAA SLTYYGHSARYDY
WGQGTQVTVSS ID41B ((ID2B with R107H) x (ID1B with R105H), with [G4S]4 linker) (SEQ ID NO: 16)
DVQLQESGGGLVQAGDSLRLSCAASGATLS SYTMG WFRQAPEKEREFVA GSSRDGRTNYYANSVKG RFTISRDNAKNTVVLQMNSLKPEDTAVYYCAA HTTSGVPVHERSYAY
WGQGTQVTVSS GGGGSGGGGSGGGGSGGGGS
DVQLQESGGGLVQAGGSLRLSCAASGATFS SYYIG WFRQAPGKEREFVA AINGSGGNRISADSVKG RFTISRDNAKNTVVLQLNSLKPEDTAVYYCAA SLTYYGHSARYDY
WGQGTQVTVSS ID43B ((ID2B with R108H) x (ID1B with R105H), with [G4S]4 linker) (SEQ ID NO: 17)
DVQLQESGGGLVQAGDSLRLSCAASGATLS SYTMG WFRQAPEKEREFVA GSSRDGRTNYYANSVKG RFTISRDNAKNTVVLQMNSLKPEDTAVYYCAA HTTSGVPVHERSYAY
WGQGTQVTVSS GGGGSGGGGSGGGGSGGGGS
DVQLQESGGGLVQAGGSLRLSCAASGATFS SYYIG WFRQAPGKEREFVA AINGSGGNRISADSVKG RFTISRDNAKNTVVLQLNSLKPEDTAVYYCAA SLTYYGHSAHYDY
WGQGTQVTVSS ID45B (ID2B with D1E and Q5V, wild type R107) (SEQ ID NO: 18)
EVQLVESGGGLVQAGDSLRLSCAASGATLS SYTMG WFRQAPEKEREFVA GSSRDGRTNYYANSVKG RFTISRDNAKNTVVLQMNSLKPEDTAVYYCAA HTTSGVPVRERSYAY
WGQGTQVTVSS ID46B (ID45B with R107H) (SEQ ID NO: 19)
EVQLVESGGGLVQAGDSLRLSCAASGATLS SYTMG WFRQAPEKEREFVA GSSRDGRTNYYANSVKG RFTISRDNAKNTVVLQMNSLKPEDTAVYYCAA HTTSGVPVHERSYAY
WGQGTQVTVSS ID47B (ID45B with R107A) (SEQ ID NO: 20)
EVQLVESGGGLVQAGDSLRLSCAASGATLS SYTMG WFRQAPEKEREFVA GSSRDGRTNYYANSVKG RFTISRDNAKNTVVLQMNSLKPEDTAVYYCAA HTTSGVPVAERSYAY
WGQGTQVTVSS ID48B (ID45B with R107Q) (SEQ ID NO: 21)
EVQLVESGGGLVQAGDSLRLSCAASGATLS SYTMG WFRQAPEKEREFVA GSSRDGRTNYYANSVKG RFTISRDNAKNTVVLQMNSLKPEDTAVYYCAA HTTSGVPVQERSYAY
WGQGTQVTVSS ID49B (ID45B with R107F) (SEQ ID NO: 22)
EVQLVESGGGLVQAGDSLRLSCAASGATLS SYTMG WFRQAPEKEREFVA GSSRDGRTNYYANSVKG RFTISRDNAKNTVVLQMNSLKPEDTAVYYCAA HTTSGVPVFERSYAY
WGQGTQVTVSS -continued CDRs 1, 2 and 3 are the first, second and third underlined portions of each ICVD or construct.
FRs 1, 2, 3 and 4 are the first, second, third and fourth portions joining the CDRs of each
ICVD. The linker is also shown in the case of biheads. Substitutions relative to unmodified
comparators are shown italicised and emboldened. Substitution descriptions in brackets are
referred-to by N-to-C-terminal numbering (as opposed to Kabat numbering).

ID50B (ID45B with R107W) (SEQ ID NO: 23)
EVQLVESGGGLVQAGDSLRLSCAASGATLS SYTMG WFRQAPEKEREFVA GSSRDGRTNYYANSVKG RFTISRDNAKNTVVLQMNSLKPEDTAVYYCAA HTTSGVPVWERSYAY
WGQGTQVTVSS Anti-TcdA ID17A (SEQ ID NO: 24)
DVQLQESGGGLVQAGGSLRLSCAASGATSD VYAMG WFRQVPGKEREFVA TINRSGSDSYYADSVKG RFTISRDNAKNTVLQMNSLKPEETAVYYCAA SRSDCIGYGCRRVSQDY
WGQGTQVTVSS
GGGSGGGGSGGGGSGGGGS
DVQLQESGGGLVQAGGSLRLSCVISGMDFS HKPAG WFRQAPGKEREFVA SITTRASTHYADSVKG RFTISRDNAKNTVYLEMNSLKPEDTAVYYCNS EYY WGQGTQVTVSS ID29A (ID17A with R109H) (SEQ ID NO: 25)
DVQLQESGGGLVQAGGSLRLSCAASGATSD VYAMG WFRQVPGKEREFVA TINRSGSDSYYADSVKG RFTISRDNAKNTVLQMNSLKPEETAVYYCAA SRSDCIGYGCHRVSQDY
WGQGTQVTVSS
GGGSGGGGSGGGGSGGGGS
DVQLQESGGGLVQAGGSLRLSCVISG MDFS HKPAG WFRQAPGKEREFVA SITTRASTHYADSVKG RFTISRDNAKNTVYLEMNSLKPEDTAVYYCNS EYY WGQGTQVTVSS Anti-IL-6R 7F6 (SEQ ID NO: 32)
EVQLVESGGGLVQAGGSTRLTCLASGSSISS INVIG WYRQAPGKQRELVA IIGKGGGTNYADFVKG RFTISRDNSKNTVLQMNSLKPEDTAVYYCYA DYEDRDSPFNGS
WGQGTQVTVSS ID-3V (7F6 with R102H) (SEQ ID NO: 33)
EVQLVESGGGLVQAGGSTRLTCLASGSSISS INVIG WYRQAPGKQRELVA IIGKGGGTNYADFVKG RFTISRDNSKNTVLQMNSLKPEDTAVYYCYA DYEDHDSPFNGS
WGQGTQVTVSS 5G9 (SEQ ID NO: 34)
EVQLVESGGGLVQAGGSTRLTCKASGSIFNINS INVMA WYRQAPGKQRELVA IIGKGGGTNYADFVKG RFTISRDAAKNTVNLQMNSLKPEDTAVYYCYA DYEDRDSPFNAS
WGQGTQVTVSS ID-54V (5G9 with R105H) (SEQ ID NO: 35)
EVQLVESGGGLVQAGGSTRLTCKASGSIFNINS INVMA WYRQAPGKQRELVA IIGKGGGTNYADFVKG RFTISRDAAKNTVNLQMNSLKPEDTAVYYCYA DYEDHDSPFNAS
WGQGTQVTVSS Suitably at least one, such as two, such as three arginine and/or lysine residues in the CDRs of a polypeptide of the invention are substituted with a histidine residue. Suitably one arginine and/or lysine residue is substituted. Suitably the substitutions are made in at least one, such as at least two, such as three CDRs. Suitably 1 to 3, such as 1 to 2, such as 1 substitution(s) are made in all three, two or one CDR(s) of a polypeptide of the invention. Suitably no more than three, such as no more than 2 lysine and/or arginine residues are substituted.

Suitably each lysine and/or arginine residue in CDR1, CDR2 and/or CDR3 of a polypeptide of the invention has been substituted with at least one, more suitably one, histidine residue each.

Suitably each CDR of a polypeptide of the invention which includes a substitution is no shorter than 3, more suitably no shorter than 4, more suitably no shorter than 5, more suitably no shorter than 6, more suitably no shorter than 7, more suitably no shorter than 8, more suitably no shorter than 9, more suitably no shorter than 10, more suitably no shorter than 11, more suitably no shorter than 12, more suitably no shorter than 13 amino acids.

Suitably each CDR of a polypeptide of the invention which includes a substitution is no longer than 35, more suitably no longer than 30, more suitably no longer than 25, more suitably no longer than 23, more suitably no longer than 21, more suitably no longer than 20, more suitably no longer than 19, more suitably no longer than 18, more suitably no longer than 17 amino acids.

Suitably the polypeptide of the invention is no longer than 2000, more suitably no longer than 1500, more suitably no longer than 1200, more suitably no longer than 900, more suitably no longer than 700, more suitably no longer than 600, more suitably no longer than 500, more suitably no longer than 400, more suitably no longer than 300, more suitably no longer than 250, more suitably no longer than 200, more suitably no longer than 150 amino acids.

Windows Defined within CDRs

The residues within a CDR may be considered to belong to a particular fraction of that CDR. For example, a CDR consisting of fifteen amino acids (ARNECDQGHILKMFP, SEQ ID NO: 26) can be considered to consist of three thirds: a first third (a window consisting of ARNEC, SEQ ID NO: 27), a second third (a window consisting of DQGHI, SEQ ID NO: 28) and a third third (a window consisting of LKMFP, SEQ ID NO: 29). Similarly, this CDR can be considered to consist of five fifths: a first fifth (a window consisting of ARN), a second fifth (a window consisting of ECD), a third fifth (a window consisting of QGH), a fourth fifth (a window consisting of ILK) and a fifth fifth (a window consisting of MFP). The numbering of the fractions of a CDR is from N- to C-terminus. If a CDR consists of a number of residues such that division into fractions would result in a non-whole number of residues residing in each fraction (such as sevenths of a CDR consisting of ARNECDQGHILKMFP, SEQ ID NO: 26) then (a) if the CDR consists of an odd number of residues, then the number of residues in the central fraction (e.g. the second third or the third fifth, etc) is rounded up to the nearest odd number or (b) if the CDR consists of an even number of residues, then the number of residues in the central fraction is rounded up and to the nearest even number. For example, the fourth seventh of a CDR consisting of ARNECDQGHILKMFP is the window consisting of QGH and the second third of a CDR consisting of ARNECDQG (SEQ ID NO: 30) is the window consisting of NECD (SEQ ID NO: 31).

Suitably the at least one lysine and/or arginine residue is present in a window defined as the second third of CDR1 and/or the second third of CDR2 and/or the second third of CDR3 and/or the third fifth of CDR1 and/or the third fifth of CDR2 and/or the third fifth of CDR3 and/or the fourth seventh of CDR1 and/or the fourth seventh of CDR2 and/or the fourth seventh of CDR3.

According to a specific embodiment, a polypeptide according to the invention does not have an amino acid sequence which is exactly the same as (i.e. shares 100% sequence identity with) the amino acid sequence of a naturally occurring polypeptide.

In one embodiment there is provided a polypeptide comprising an immunoglobulin chain variable domain comprising three complementarity determining regions (CDR1-CDR3) and four framework regions, having: (a) at least one histidine residue in place of at least one lysine residue in CDR1, CDR2 and/or CDR3, and/or (b) at least one histidine residue in place of at least one arginine residue in CDR1, CDR2 and/or CDR3; wherein the polypeptide has increased intestinal stability relative to a corresponding progenitor polypeptide not having said histidine substitutions.

A progenitor polypeptide is suitably a polypeptide which has not undergone the inventive histidine substitutions disclosed herein. Suitably the corresponding progenitor polypeptide is the 'wild type' polypeptide (for example an antibody) which was directly produced by an animal, for example by V(D)J recombination and somatic mutation (such as a llama, such as following immunisation), and which may have optionally undergone further synthetic modifications, before undergoing the inventive histidine substitutions disclosed herein.

Specificity, Affinity and Avidity

Specificity refers to the number of different types of antigens or antigenic determinants to which a particular antigen-binding polypeptide can bind. The specificity of an antigen-binding polypeptide is the ability of the antigen-binding polypeptide to recognise a particular antigen as a unique molecular entity and distinguish it from another.

Affinity, represented by the equilibrium constant for the dissociation of an antigen with an antigen-binding polypeptide (Kd), is a measure of the binding strength between an antigenic determinant and an antigen-binding site on an antigen-binding polypeptide: the lesser the value of the Kd, the stronger the binding strength between an antigenic determinant and the antigen-binding polypeptide (alternatively, the affinity can also be expressed as the affinity constant (Ka), which is 1/Kd). Affinity can be determined by known methods, depending on the specific antigen of interest.

Avidity is the measure of the strength of binding between an antigen-binding polypeptide and the pertinent antigen. Avidity is related to both the affinity between an antigenic determinant and its antigen-binding site on the antigen-binding polypeptide and the number of pertinent binding sites present on the antigen-binding polypeptide.

Suitably, polypeptides of the invention bind to their target with a dissociation constant (Kd) of $10^{-6}$ to $10^{-12}$ M, more suitably $10^{-7}$ to $10^{-12}$ M, more suitably $10^{-8}$ to $10^{-12}$ M and more suitably $10^{-9}$ to $10^{-12}$ M.

Any Kd value less than $10^{-6}$ is considered to indicate specific binding. Specific binding of an antigen-binding polypeptide to an antigen or antigenic determinant can be determined in any suitable known manner, including, for example, Scatchard analysis and/or competitive binding assays, such as radioimmunoassays (RIA), enzyme immunoassays (EIA) and sandwich competition assays, and the different variants thereof known in the art.

Potency, Inhibition and Neutralisation

Potency is a measure of the activity of a therapeutic agent expressed in terms of the amount required to produce an effect of given intensity. A highly potent agent evokes a greater response at low concentrations compared to an agent of lower potency that evokes a smaller response at low concentrations. Potency is a function of affinity and efficacy. Efficacy refers to the ability of therapeutic agent to produce a biological response upon binding to a target ligand and the quantitative magnitude of this response. The term half maximal effective concentration (EC50) refers to the concentration of a therapeutic agent which causes a response halfway between the baseline and maximum after a specified exposure time. The therapeutic agent may cause inhibition or stimulation. It is commonly used, and is used herein, as a measure of potency.

A neutralising polypeptide for the purposes of the invention is a polypeptide which binds to an agent (such as TNF-alpha) inhibiting the binding of the agent to one or more of its cognate receptors (such as TNFR1 and TNFR2), as measured by ELISA. Alternatively, or in addition, a neutralising polypeptide for the purposes of the invention is a polypeptide which defends a cell from the effects of an agent (such as TN F-alpha) by, for example, inhibiting the biological effect of the agent. For example, a neutralising polypeptide for the purposes of the invention is a polypeptide which defends a cell from the effects of a toxin (such as *Clostridium Difficile* Toxin A or B—"TcdA/TcdB") by, for example, inhibiting the biological effect of the toxin. Alternatively, or in addition, a neutralising polypeptide for the purposes of the invention is a polypeptide which binds to IL-6R (and therefore the IL-6R/IL-6 complex), inhibiting binding of the IL-6R/IL-6 complex to gp130, as measured by ELISA.

The effectiveness (e.g. neutralising ability) of a therapeutic agent can be ascertained using a potency assay. A particularly suitable potency assay is the measurement of Vero cell viability using Alamar Blue (Fields and Lancaster *American Biotechnology Laboratory* 1993 11(4):48-50). Using a range of known concentrations of a toxin, this assay can be performed to ascertain the ability of a therapeutic polypeptide to neutralise the effects of the toxin by producing a dose-response curve and/or by ascertaining the half maximal effective concentration (EC50) of the therapeutic polypeptide. This Vero Cell Cytotoxicity Standard Assay is used herein and detailed further in the Examples section below.

Another particularly suitable potency assay is the Standard TNFR2/TNF Interference ELISA Assay (detailed further in the Examples section below), which tests the effectiveness of a therapeutic agent in blocking TNF-alpha binding to TNFR2, in respect of a range of known concentrations of agent, producing a dose-response curve and/or by ascertaining the half maximal effective concentration (EC50) of the therapeutic polypeptide.

Another particularly suitable potency assay is the Standard gp130 ELISA Assay (detailed further in the Examples section below), which tests the effectiveness of a therapeutic agent in blocking the sIL-6/IL-6R complex binding to gp130, in respect of a range of known concentrations of agent, producing a dose-response curve and/or by ascertaining the half maximal effective concentration (EC50) of the therapeutic polypeptide.

Suitably the potency of the polypeptide of the invention is substantially the same as the potency of a corresponding polypeptide not having histidine substitutions of the invention.

Suitably, the polypeptide of the invention or the polypeptide of the methods of the invention inhibits binding of a binding agent to a binding partner, such as TNF-alpha to TNFR2 in the Standard TNF/TNFR2 Interference ELISA Assay, with an EC50 of 300 nM or less, more suitably 200 nM or less, more suitably 100 nM or less, more suitably 80 nM or less, more suitably 60 nM or less, more suitably 40 nM or less, more suitably 20 nM or less, more suitably 10 nM or less, more suitably 5 nM or less.

Suitably, the EC50 of the polypeptide of the invention or the polypeptide of the methods of the invention is increased by no more than 300 pM, more suitably no more than 200 pM, more suitably no more than 100 pM, more suitably no more than 50 pM, more suitably no more than 25 pM, more suitably no more than 10 pM, more suitably no more than 5 pM, relative to a corresponding polypeptide not having histidine substitutions of the invention, such as in inhibiting binding of TNF alpha to TNFR2 in the Standard TNF/TNFR2 Interference ELISA Assay.

Suitably, the EC50 of the polypeptide of the invention or the polypeptide of the methods of the invention is increased by no more than 500%, more suitably 400%, more suitably 300%, more suitably 200%, more suitably 100%, more suitably 70%, more suitably 60%, more suitably 50%, more suitably 40%, more suitably 30%, more suitably 25%, more suitably 20%, more suitably 15%, more suitably 10%, more suitably 5%, more suitably 2%, more suitably 1%, relative to a corresponding polypeptide not having histidine substitutions of the invention, such as in inhibiting binding of TNF-alpha to TNFR2 in the Standard TNF/TNFR2 Interference ELISA Assay.

Suitably the polypeptide of the invention or the polypeptide of the methods of the invention neutralizes the cytotoxicity of a toxin, such as TcdA or TcdB, in the Vero Cell Cytotoxicity Standard Assay with an EC50 of 100 nM or less, more suitably 80 nM or less, more suitably 60 nM or less, more suitably 40 nM or less, more suitably 30 nM or less, more suitably 20 nM or less, more suitably 10 nM or less, more suitably 9 nM or less, more suitably 8 nM or less, more suitably 7 nM or less, more suitably 6 nM or less more suitably 5 nM or less, more suitably 4 nM or less, more suitably 3 nM or less, more suitably 2 nM or less, more suitably 1 nM or less.

Suitably, the EC50 of the polypeptide of the invention or the polypeptide of the methods of the invention is increased by no more than 200 nM, more suitably 150 nM, more suitably 100 nM, more suitably 80 nM, more suitably 60 nM, more suitably 40 nM, more suitably 20 nM, more suitably 10 nM, more suitably 5 nM, relative to a corresponding polypeptide not having histidine substitutions of the invention, in neutralising the cytotoxicity of a toxin, such as TcdA or TcdB, in the Vero Cell Cytotoxicity Standard Assay.

Suitably, the EC50 of the polypeptide of the invention or the polypeptide of the methods of the invention is increased by no more than 500%, more suitably 400%, more suitably 300%, more suitably 200%, more suitably 100%, more suitably 70%, more suitably 60%, more suitably 50%, more suitably 40%, more suitably 30%, more suitably 25%, more suitably 20%, more suitably 15%, more suitably 10%, more suitably 5%, more suitably 2%, more suitably 1%, relative to a corresponding polypeptide not having histidine substitutions of the invention, in neutralising the cytotoxicity of a toxin, such as TcdA or TcdB, in the Vero Cell Cytotoxicity Standard Assay.

Suitably, the polypeptide of the invention or the polypeptide of the methods of the invention inhibits binding of a binding agent to a binding partner, such the sIL-6/IL-6R complex binding to gp130 in the Standard gp130 ELISA Assay, with an EC50 of 300 nM or less, more suitably 200 nM or less, more suitably 100 nM or less, more suitably 80 nM or less, more suitably 60 nM or less, more suitably 40 nM or less, more suitably 20 nM or less, more suitably 10 nM or less, more suitably 5 nM or less, more suitably 1 nM or less, more suitably 0.5 nM or less, more suitably 0.3 nM or less, more suitably 0.2 nM or less, more suitably 0.15 nM or less.

Suitably, the EC50 of the polypeptide of the invention or the polypeptide of the methods of the invention is increased by no more than 300 pM, more suitably no more than 200 pM, more suitably no more than 100 pM, more suitably no more than 80 pM, more suitably no more than 70 pM, more suitably no more than 60 pM, more suitably no more than 50 pM, more suitably no more than 25 pM, more suitably no more than 20 pM, more suitably no more than 15 pM, more suitably no more than 10 pM, more suitably no more than 5 pM, relative to a corresponding polypeptide not having histidine substitutions of the invention, such as in inhibiting binding of a binding agent to a binding partner, such the sIL-6/IL-6R complex binding to gp130 in the Standard gp130 ELISA Assay.

Suitably, the EC50 of the polypeptide of the invention or the polypeptide of the methods of the invention is increased by no more than 600%, more suitably no more than 500%, more suitably 400%, more suitably 300%, more suitably 200%, more suitably 100%, more suitably 70%, more suitably 60%, more suitably 50%, more suitably 40%, more suitably 30%, more suitably 25%, more suitably 20%, more suitably 15%, more suitably 10%, more suitably 5%, more suitably 2%, more suitably 1%, relative to a corresponding polypeptide not having histidine substitutions of the invention, such the sIL-6/IL-6R complex binding to gp130 in the Standard gp130 ELISA Assay.

Substitutions may be made to a polypeptide with the objective of introducing pH sensitivity, for example to significantly reduce the affinity of an antibody for an antigen upon entry of the antibody into the acidic endosome. However, the substitutions of the present invention suitably do not invoke substantial pH sensitivity. Suitably the substitutions to the polypeptide of the invention or the substitutions to the polypeptide of the methods of the invention are not for engineering pH dependency of target binding. Suitably the affinity of the polypeptide of the invention or the polypeptide of the methods of the invention remains substantially the same at any pH from 3 to 9, more suitably any pH from 4 to 8.

The Gastrointestinal Tract (GIT) and Digestive Enzymes

The GIT is an organ system responsible for consuming and digesting foodstuffs, absorbing nutrients, and expelling waste. In humans and other mammals, the GIT consists of the mouth, oesophagus, stomach, small intestine (duodenum, jejunum and ileum) and large intestine (cecum, colon, rectum and anal canal). The intestinal tract, as opposed to the gastrointestinal tract, consists of only the small intestine and the large intestine. Various pathogens may colonise, and various diseases may manifest in, different areas of the gastrointestinal tract.

The different parts of the gastrointestinal tract each contain a complex mixture of digestive enzymes. These digestive enzymes include proteases, lipases, amylases and nucleases. Proteases include serine proteases, threonine proteases, cysteine proteases, aspartate proteases, glutamic acid proteases and metalloproteases. Proteases are involved in digesting polypeptide chains into shorter fragments by splitting the peptide bonds that link amino acid residues (proteolysis). Some detach the terminal amino acids from the protein chain (exopeptidases); others attack internal peptide bonds of a protein (endopeptidases). The intestinal tract comprises a vast array of different proteases.

Proteolysis in the intestinal tract can be highly promiscuous such that a wide range of protein substrates are hydrolysed by the wide variety of proteases present. This is the case for proteases which cleave the wide array of ingested polypeptides in the intestinal tract into smaller polypeptide fragments.

Suitably the substitutions made to the polypeptide of the invention or to the polypeptide of the methods of the invention increase the stability of the polypeptide to one or more proteases present in the small or large intestine, relative to a corresponding polypeptide not having histidine substitutions of the invention. Suitably the proteases include proteases originating from intestinal microbiota or pathogenic bacteria, for example wherein the proteases are cell membrane-attached proteases, secreted proteases and/or proteases released on cell lysis. Suitably the one or more proteases are selected from the group consisting of trypsin, chymotrypsin, host inflammatory proteases, proteases originating from microbiota and proteases originating from pathogenic bacteria such as *C. difficile*-specific proteases. Suitably the intestinal tract is a mammalian intestinal tract, such as a human, simian, murine, bovine, ovine, canine, feline, equine or porcine intestinal tract.

Suitably the substitutions made to the polypeptide of the invention, or substitutions made to the polypeptide of the methods of the invention, increase the stability of the polypeptide in the intestinal tract, or in a model of the intestinal tract, such as in the small and/or large intestine, such as in the duodenum, jejunum, ileum cecum, colon, rectum and/or anal canal, relative to a corresponding polypeptide not having histidine substitutions of the invention. Suitably the model of the intestinal tract is the Standard Human Faecal Supernatant Intestinal Tract Model, the Standard Mouse Small Intestinal Supernatant Intestinal Tract Model, or the Standard Trypsin Intestinal Tract Model.

Suitably at least 20%, more suitably at least 25%, more suitably at least 30%, more suitably at least 35%, more suitably at least 40%, more suitably at least 50%, more suitably at least 60% of the polypeptide of the invention or the polypeptide of the methods of the invention remains viable, as determined for example by the Standard TNFR2/TNF Interference ELISA Assay when the ICVD is an anti-TNF-alpha ICVD or the Standard Toxin ELISA Assay when the ICVD is an anti-toxin ICVD, after 6 or 16 hours incubation in the Standard Mouse Small Intestinal Supernatant Intestinal Tract Model.

Suitably the stability of a polypeptide of the invention or the polypeptide of the methods of the invention, as determined for example by the Standard TNFR2/TNF Interference ELISA Assay when the ICVD is an anti-TNF-alpha ICVD or the Standard Toxin ELISA Assay when the ICVD is an anti-toxin ICVD, is increased by at least 1%, more suitably 2%, more suitably 3%, more suitably 5%, more suitably 7%, more suitably 10%, more suitably 15%, more suitably 20%, more suitably 30%, more suitably 40%, more suitably 50%, more suitably 60%, more suitably 70%, relative to a corresponding polypeptide not having histidine substitutions of the invention, after 6 or 16 hours incubation in the Standard Mouse Small Intestinal Supernatant Intestinal Tract Model.

Suitably at least 20%, more suitably at least 25%, more suitably at least 30%, more suitably at least 35%, more suitably at least 40%, more suitably at least 50%, more suitably at least 60%, more suitably at least 70%, more suitably at least 80%, more suitably at least 90% of the polypeptide of the invention or the polypeptide of the methods of the invention remains viable, as determined for example by the Standard TNFR2/TNF Interference ELISA Assay when the ICVD is an anti-TNF-alpha ICVD, the Standard Toxin ELISA Assay when the ICVD is an anti-toxin ICVD or the Standard Western Blot Stability Assay after 30 minutes, 1 hour, 4 hours or 16 hours incubation in the Standard Human Faecal Supernatant Intestinal Tract Model.

Suitably the stability of a polypeptide of the invention or the polypeptide of the methods of the invention, as determined for example by the Standard TNFR2/TNF Interference ELISA Assay when the ICVD is an anti-TNF-alpha ICVD, the Standard Toxin ELISA Assay when the ICVD is an anti-toxin ICVD or the Standard Western Blot Stability Assay, is increased by at least 1%, more suitably 2%, more suitably 3%, more suitably 5%, more suitably 7%, more suitably 10%, more suitably 15%, more suitably 20%, more suitably 25%, more suitably 30%, more suitably 40%, more suitably 50%, more suitably 60%, more suitably 70%, relative to a corresponding polypeptide not having histidine substitutions of the invention, after 30 minutes, 1 hour, 4 hours or 16 hours incubation in the Standard Human Faecal Supernatant Intestinal Tract Model.

Suitably at least 5%, more suitably at least 10%, more suitably at least at least 20%, more suitably at least 25%, more suitably at least 30%, more suitably at least 35%, more suitably at least 40%, more suitably at least 50%, more suitably at least 60% of the polypeptide of the invention or the polypeptide of the methods of the invention remains viable, as determined for example by the Standard gp130 ELISA Assay when the ICVD is an anti-IL-6R ICVD, after 4 hours incubation in the Standard Mouse Small Intestinal Supernatant Intestinal Tract Model.

Suitably the stability of a polypeptide of the invention or the polypeptide of the methods of the invention, as determined for example by the Standard gp130 ELISA Assay when the ICVD is an anti-IL-6R ICVD, is increased by at least 1%, more suitably 2%, more suitably 3%, more suitably 5%, more suitably 7%, more suitably 10%, more suitably 15%, more suitably 20%, more suitably 30%, more suitably 40%, more suitably 50%, more suitably 60%, more suitably 70%, relative to a corresponding polypeptide not having histidine substitutions of the invention, after 4 hours incubation in the Standard Mouse Small Intestinal Supernatant Intestinal Tract Model.

Suitably at least 20%, more suitably at least 25%, more suitably at least 30%, more suitably at least 35%, more suitably at least 40%, more suitably at least 50%, more suitably at least 60%, more suitably at least 70%, more suitably at least 80%, more suitably at least 90% of the polypeptide of the invention or the polypeptide of the methods of the invention remains viable, as determined for example by the Standard gp130 ELISA Assay when the ICVD is an anti-IL-6R ICVD after 16 hours incubation in the Standard Human Faecal Supernatant Intestinal Tract Model.

Suitably the stability of a polypeptide of the invention or the polypeptide of the methods of the invention, as determined for example by the Standard gp130 ELISA Assay when the ICVD is an anti-IL-6R ICVD, is increased by at least 1%, more suitably 2%, more suitably 3%, more suitably 5%, more suitably 7%, more suitably 10%, more suitably 15%, more suitably 20%, more suitably 25%, more suitably 30%, more suitably 40%, more suitably 50%, more suitably 60%, more suitably 70%, relative to a corresponding polypeptide not having histidine substitutions of the invention, after 16 hours incubation in the Standard Human Faecal Supernatant Intestinal Tract Model.

The percentage of 'viable' ICVD remaining after incubation refers to the proportion of intact ICVD (for example in the Standard Western Blot Stability Assay), or the proportion of functional ICVD (for example in the Standard TNFR2/TNF Interference ELISA Assay when the ICVD is an anti-TNF-alpha ICVD or Standard Toxin ELISA Assay when the ICVD is an anti-toxin ICVD). Alternatively, or in addition, the percentage of 'viable' ICVD remaining after incubation refers to the proportion of intact ICVD (for example in the Standard Western Blot Stability Assay), or the proportion of functional ICVD (for example in the Standard gp130 ELISA Assay when the ICVD is an anti-IL-6R ICVD).

Diseases of the Gastrointestinal Tract

Diseases of the gastrointestinal tract refer to diseases involving the gastrointestinal tract, namely the oesophagus, stomach, small intestine (duodenum, jejunum and ileum) and large intestine (cecum, colon, rectum and anal canal). The polypeptide of the invention or the polypeptide of the methods of the invention may be used in the treatment or prevention of such diseases. Suitably the polypeptide of the invention or the polypeptide of the methods of the invention is used in local and/or topical treatment or prevention of such diseases.

Exemplary diseases of the gastrointestinal tract are described below.

Autoimmune Diseases and/or Inflammatory Diseases of the Gastrointestinal Tract

Autoimmune diseases develop when the immune system responds adversely to normal body tissues. Autoimmune disorders may result in damage to body tissues, abnormal organ growth and/or changes in organ function. The disorder may affect only one organ or tissue type or may affect multiple organs and tissues. Organs and tissues commonly affected by autoimmune disorders include blood components such as red blood cells, blood vessels, connective tissues, endocrine glands such as the thyroid or pancreas, muscles, joints and skin. An inflammatory disease is a disease characterised by inflammation. Many inflammatory diseases are autoimmune diseases and vice-versa.

The chronic inflammatory bowel diseases (IBDs) Crohn's disease and ulcerative colitis, which afflict both children and adults, are examples of autoimmune and inflammatory diseases of the gastrointestinal tract (Hendrickson et al 2002 *Clin Microbiol Rev* 15(1):79-94, herein incorporated by reference in its entirety). Ulcerative colitis is defined as a condition where the inflammatory response and morphologic changes remain confined to the colon. The rectum is involved in 95% of patients. Inflammation is largely limited to the mucosa and consists of continuous involvement of variable severity with ulceration, edema, and hemorrhage along the length of the colon (Hendrickson et al 2002 *Clin. Microbiol Rev* 15(1):79-94, herein incorporated by reference in its entirety). Ulcerative colitis is usually manifested by the presence of blood and mucus mixed with stool, along with lower abdominal cramping which is most severe during the passage of bowel movements. Clinically, the presence of diarrhoea with blood and mucus differentiates ulcerative colitis from irritable bowel syndrome, in which blood is absent. Unlike ulcerative colitis, the presentation of Crohn's disease is usually subtle, which leads to a later diagnosis. Factors such as the location, extent, and severity of involvement determine the extent of symptoms. Patients who have ileocolonic involvement usually have postprandial abdominal pain, with tenderness in the right lower quadrant and an occasional inflammatory mass.

Suitably the composition of the invention is for use in the treatment of an autoimmune and/or inflammatory disease of the gastrointestinal tract, suitably selected from the list consisting of Crohn's disease, ulcerative colitis, irritable bowel syndrome, diabetes type II, glomerulonephritis, autoimmune hepatitis, Sjogren's syndrome, coeliac disease and drug- or radiation-induced mucositis (most suitably Crohn's disease).

Infection of the Gastrointestinal Tract

Viral, bacterial, parasitic and other pathogenic infections can occur in the gastrointestinal tract. These may be confined to the gastrointestinal tract or initiated in the gastrointestinal tract before spreading to other parts of the body. The polypeptide of the invention may be used for the treatment or prevention of bacterial infection including infection by common bacterial gastrointestinal tract pathogens including *Escherichia coli, Salmonella, Campylobacter, Vibrio cholerae, Shigella, Clostridium perfringens, Clostridium difficile, Bacillus cereus, Vibrio parahaemolyticus* and *Yersinia enerocolitica*. The polypeptide of the invention may be used for the treatment or prevention of viral infection including common viral gastrointestinal tract pathogens which include rotavirus, norovirus and small round viruses. Suitably the polypeptide of the invention is for use in the treatment or prevention of nosocomial infection. Suitably the polypeptide of the invention is for use in the treatment or prevention of *C. difficile* infection.

Suitably, the polypeptide of the invention binds to a target accessible via the intestinal tract, such as a target within the intestinal tract. Suitably the target is a deleterious agent originating from an intestinal tract resident pathogenic microbe. Suitably the target is a target originating from host microbiota which may induce pathogenesis, a host cell, host derived inflammatory mediators or a protein involved in disease pathogenesis. Suitably the target is selected from the group consisting of: TNF-alpha, *C. difficile* toxin A, or *C. difficile* toxin B. Alternatively the target is selected from the group consisting of: IL-6R, TNF-alpha, *C. difficile* toxin A, or *C. difficile* toxin B.

Linkers and Multimers

A construct according to the invention comprises multiple polypeptides and therefore may suitably be multivalent. Such a construct may comprise at least two identical polypeptides according to the invention. A construct consisting of two identical polypeptides according to the invention is a "homobihead". In one aspect of the invention there is provided a construct comprising a polypeptide of the invention. In a further aspect there is provided a construct comprising two or more (possibly identical) polypeptides of the invention.

Alternatively, a construct may comprise at least two polypeptides which are different, but are both still polypeptides according to the invention (a "heterobihead").

Alternatively, such a construct may comprise (a) at least one polypeptide according to the invention and (b) at least one polypeptide such as an antibody or antigen-binding fragment thereof, which is not a polypeptide of the invention (also a "heterobihead"). The at least one polypeptide of (b) may bind TNF-alpha, TcdA or TcdB (for example via a different epitope to that of (a)), or alternatively may bind to another target altogether. Suitably the different polypeptide (b) binds to, for example, another pro inflammatory cytokine or chemokine or their respective receptors, other inflammatory mediators or immunologically relevant ligands involved in human pathological processes.

Constructs can be multivalent and/or multispecific. A multivalent construct (such as a bivalent construct) comprises two or more binding polypeptides therefore presents two or more sites at which attachment to one or more antigens can occur. An example of a multivalent construct could be a homobihead or a heterobihead. A multispecific construct (such as a bispecific construct) comprises two or more different binding polypeptides which present two or more sites at which either (a) attachment to two or more different antigens can occur or (b) attachment to two or more different epitopes on the same antigen can occur. An example of a multispecific construct could be a heterobihead. A multispecific construct is multivalent.

Suitably, the polypeptides comprised within the construct are antibody fragments. More suitably, the polypeptides comprised within the construct are selected from the list consisting of: a VHH, a VH, a VL, a V-NAR, scFv, a Fab fragment or a F(ab')2 fragment. More suitably, the polypeptides comprised within the construct are VHHs.

The polypeptides of the invention can be linked to each other directly (i.e. without use of a linker) or via a linker. The linker is suitably a polypeptide and will be selected so as to allow binding of the polypeptides to their epitopes. If used for therapeutic purposes, the linker is suitably non-immunogenic in the subject to which the polypeptides are administered. Suitably the polypeptides are all connected by linkers. Suitably the linker is of the format $(G_4S)_x$. Most suitably x is 6.

Therapeutic Use and Delivery

Suitably the polypeptide of the invention is for use as a medicament, delivered by oral administration, suitably for use in the treatment or prevention of diseases of the gastrointestinal tract (see supra). The polypeptide of the invention or the polypeptide of the methods of the invention may also be used in the treatment or prevention of other medical conditions by oral administration such as metabolic disorders, such as obesity. In one embodiment, the polypeptide of the invention is intended to have local effect in the intestinal tract. In one embodiment, the polypeptide of the invention or the polypeptide of the methods of the invention is not for use in the treatment or prevention of diseases by delivery into the circulation in therapeutically effective quantities.

In one aspect of the invention there is provided a method of treating diseases of the gastrointestinal tract comprising administering to a person in need thereof a therapeutically effective amount of the inventive polypeptide.

A therapeutically effective amount of a polypeptide is an amount which is effective, upon single or multiple dose administration to a subject, in neutralising the biological effects of a chosen target to a significant extent in a subject. A therapeutically effective amount may vary according to factors such as the disease state, age, sex, and weight of the individual, and the ability of the polypeptide to elicit a desired response in the individual. A therapeutically effective amount is also one in which any toxic or detrimental effects of the polypeptide are outweighed by the therapeutically beneficial effects. The polypeptide of the invention can be incorporated into pharmaceutical compositions suitable for oral administration to a subject. The polypeptide of the invention can be in the form of a pharmaceutically acceptable salt.

In one aspect of the invention, there is provided a pharmaceutical composition comprising a polypeptide of the invention and one or more pharmaceutically acceptable diluents or carriers.

A pharmaceutical composition of the invention may be formulated for oral delivery. The pharmaceutical compositions of the invention may be in a variety of forms. These include, for example, liquid, semi-solid and solid dosage forms, such as liquid solutions, dispersions or suspensions, tablets, pills and powders. Solid dosage forms are preferred. The pharmaceutical composition may comprise a pharmaceutically acceptable excipient, and suitably may be used in the form of ingestible tablets, buccal tablets, troches, capsules, elixirs, suspensions, syrups, wafers, and the like.

Typically, the composition of the invention or pharmaceutical composition of the invention comprises a polypeptide of the invention and a pharmaceutically acceptable excipient such as a carrier. Examples of pharmaceutically acceptable carriers include one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the polypeptide of the invention. Pharmaceutical compositions may include antiadherents, binders, coatings, disintegrants, flavours, colours, lubricants, sorbents, preservatives, sweeteners, freeze dry excipients (including lyoprotectants) or compression aids. Suitably, the polypeptide of the invention is lyophilised before being incorporated into a pharmaceutical composition.

A polypeptide of the invention may also be provided with an enteric coating. An enteric coating is a polymer barrier applied on oral medication which protects the polypeptide from the low pH of the stomach. Materials used for enteric coatings include fatty acids, waxes, shellac, plastics, and plant fibers. Suitable enteric coating components include methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), methyl methacrylate-methacrylic acid copolymers, sodium alginate and stearic acid. Suitable enteric coatings include pH-dependent release polymers. These are polymers which are insoluble at the highly acidic pH found in the stomach, but which dissolve rapidly at a less acidic pH. Thus, suitably, the enteric coating will not dissolve in the acidic juices of the stomach (pH ~3), but will do so in the higher pH environment present in the small intestine (pH above 6) or in the colon (pH above 7.0). The pH-dependent release polymer is selected such that the polypeptide of the invention will be released at about the time that the dosage reaches the target region of the intestinal tract.

The composition of the invention may be formulated in a buffer, in order to stabilise the pH of the composition, at a concentration between 5-50, or more suitably 15-40 or more suitably 25-30 g/litre. Examples of suitable buffer components include physiological salts such as sodium citrate and/or citric acid. Suitably buffers contain 100-200, more suitably 125-175 mM physiological salts such as sodium chloride. Suitably the buffer is selected to have a pKa close to the pH of the composition or the physiological pH of the patient.

Exemplary polypeptide concentrations in a pharmaceutical composition may range from about 10 ng/mL to about 200 mg/mL, such as about 50 ng/mL to about 100 mg/mL, such as about 1 ug/mL to about 80 mg/mL, such as about 10 ug/mL to about 50 mg/mL, such as about 50 ug/mL to about 30 mg/mL, such as about 100 ug/mL to about 20 mg/mL, or about 1 mg/mL to about 200 mg/ml or from about 50 mg/mL to about 200 mg/mL, or from about 150 mg/mL to about 200 mg/mL.

An aqueous formulation of the polypeptide of the invention may be prepared in a pH-buffered solution, e.g., at pH ranging from about 4.0 to about 7.0, or from about 5.0 to about 6.0, or alternatively about 5.5. Examples of suitable buffers include phosphate-, histidine-, citrate-, succinate-, acetate-buffers and other organic acid buffers. The buffer concentration can be from about 1 mM to about 100 mM, or from about 5 mM to about 50 mM, depending, for example, on the buffer and the desired tonicity of the formulation.

The tonicity of the pharmaceutical composition may be altered by including a tonicity modifier. Such tonicity modifiers can be charged or uncharged chemical species. Typical uncharged tonicity modifiers include sugars or sugar alcohols or other polyols, preferably trehalose, sucrose, mannitol, glycerol, 1,2-propanediol, raffinose, sorbitol or lactitol (especially trehalose, mannitol, glycerol or 1,2-propanediol). Typical charged tonicity modifiers include salts such as a combination of sodium, potassium or calcium ions, with chloride, sulfate, carbonate, sulfite, nitrate, lactate, succinate, acetate or maleate ions (especially sodium chloride or sodium sulphate); or amino acids such as arginine or histidine. Suitably, the aqueous formulation is isotonic, although hypertonic or hypotonic solutions may be suitable. The term "isotonic" denotes a solution having the same tonicity as some other solution with which it is compared, such as physiological salt solution or serum. Tonicity agents may be used in an amount of about 5 mM to about 350 mM, e.g., in an amount of 1 mM to 500 nM. Suitably, at least one isotonic agent is included in the composition.

A surfactant may also be added to the pharmaceutical composition to reduce aggregation of the formulated polypeptide and/or minimize the formation of particulates in the formulation and/or reduce adsorption. Exemplary surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulfate (SDS). Examples of suitable polyoxyethylenesorbitan-fatty acid esters are polysorbate 20, and polysorbate 80. Exemplary concentrations of surfactant may range from about 0.001% to about 10% w/v.

A lyoprotectant may also be added in order to protect the polypeptide of the invention against destabilizing conditions during the lyophilization process. For example, known lyoprotectants include sugars (including glucose, sucrose, mannose and trehalose); polyols (including mannitol, sorbitol and glycerol); and amino acids (including alanine, glycine and glutamic acid). Lyoprotectants can be included in an amount of about 10 mM to 500 mM.

The dosage ranges for administration of the pharmaceutical composition of the invention are those to produce the desired therapeutic effect. The dosage range required depends on the precise nature of the pharmaceutical composition, the target region of the intestinal tract, the nature of the formulation, the age of the patient, the nature, extent or severity of the patient's condition, contraindications, if any, and the judgement of the attending physician. Variations in these dosage levels can be adjusted using standard empirical routines for optimisation.

The increased intestinal stability of a polypeptide of the invention means that a lower dose may be delivered orally than would otherwise need to be delivered orally in the case of a corresponding polypeptide not having histidine substitutions of the invention.

Suitable daily dosages of a polypeptide of the invention or pharmaceutical composition of the invention are in the range of 50 ng-50 mg per kg, such as 50 ug-40 mg per kg, such as 5-30 mg per kg of (e.g. human) body weight, such as less than 25, such as less than 20, such as less than 15, such as less than 10 mg, such as less than 50 ug, such as less than 50 ng per kg of body weight. The unit dose will typically will be in the region of 250-2000 mg per dose, such as from less than 1000 mg, such as less than 700 mg, such as less than 400 mg, such as less than 100 mg, such as less than 100 ug, such as less than 50 ug, such as less than 10 ug, such as less than 100 ng, such as less than 50 ng.

A dose may be administered daily or more frequently, for example 2, 3 or 4 times per day or less frequently for example every other day, once per week, once per fortnight or once per month.

Treatment of diseases also embraces treatment of exacerbations thereof and also embraces treatment of patients in remission from disease symptoms to prevent relapse of disease symptoms.

Combination Therapy

A pharmaceutical composition of the invention may also comprise one or more active agents (e.g. active agents suitable for treating diseases such as those mentioned herein). It is within the scope of the invention to use the pharmaceutical composition of the invention in therapeutic methods for the treatment of bacterial infection, autoimmune and/or inflammatory diseases as an adjunct to, or in conjunction with, other established therapies normally used in the treatment of bacterial, autoimmune and/or inflammatory diseases.

For the treatment of inflammatory bowel disease (such as Crohn's disease or ulcerative colitis), possible combinations include combinations with, for example, one or more active agents selected from the list comprising: 5-aminosalicylic acid, or a prodrug thereof (such as sulfasalazine, olsalazine or bisalazide); corticosteroids (e.g. prednisolone, methylprednisolone, or budesonide); immunosuppressants (e.g. cyclosporin, tacrolimus, methotrexate, azathioprine or 6-mercaptopurine); anti-TNF-alpha antibodies (e.g., infliximab, adalimumab, certolizumab pegol or golimumab); anti-IL12/IL23 antibodies (e.g., ustekinumab); anti-IL-6R antibodies or small molecule IL12/IL23 inhibitors (e.g., apilimod); Anti-alpha-4-beta-7 antibodies (e.g., vedolizumab); MAdCAM-1 blockers (e.g., PF-00547659); antibodies against the cell adhesion molecule alpha-4-integrin (e.g., natalizumab); antibodies against the IL2 receptor alpha subunit (e.g., daclizumab or basiliximab); JAK3 inhibitors (e.g., tofacitinib or R348); Syk inhibitors and prodrugs thereof (e.g., fostamatinib and R-406); Phosphodiesterase-4 inhibitors (e.g., tetomilast); HMPL-004; probiotics; Dersalazine; semapimod/CPSI-2364; and protein kinase C inhibitors (e.g. AEB-071). The most suitable combination agents are infliximab, adalimumab, certolizumab pegol or golimumab.

For the treatment of bacterial infections, such as *Clostridium difficile* infection, possible combinations include combinations with, for example, one or more active agents selected from the list comprising *C. difficile* toxoid vaccine, ampicillin, amoxicillin, vancomycin, metronidazole, fidaxomicin, linezolid, nitazoxanide, rifaximin, ramoplanin, difimicin, clindamycin, cephalosporins (such as second and third generation cephalosporins), fluoroquinolones (such as gatifloxacin or moxifloxacin), macrolides (such as erythromycin, clarithromycin, azithromycin), penicillins, aminoglycosides, trimethoprim-sulfamethoxazole, chloramphenicol, tetracycline, imipenem, meropenem, antibacterial agents, bactericides, or bacteriostats. Possible combinations also include combinations with one or more active agents which are probiotics, for example *Saccharomyces boulardii* or *Lactobacillus rhamnosus* GG.

Hence another aspect of the invention provides a pharmaceutical composition of the invention in combination with one or more further active agents, for example one or more active agents described above. In a further aspect of the invention, the pharmaceutical composition or polypeptide is administered sequentially, simultaneously or separately with at least one active agent selected from the list above.

Similarly, another aspect of the invention provides a combination product comprising:

(A) a pharmaceutical composition of the present invention; and (B) one or more other active agents, wherein each of components (A) and (B) is formulated in admixture with a pharmaceutically-acceptable adjuvant, diluent or carrier. In this aspect of the invention, the combination product may be either a single (combination) formulation or a kit-of-parts. Thus, this aspect of the invention encompasses a combination formulation including a pharmaceutical composition of the present invention and another therapeutic agent, in admixture with a pharmaceutically acceptable adjuvant, diluent or carrier.

The invention also encompasses a kit of parts comprising components:

(i) a pharmaceutical composition of the present invention in admixture with a pharmaceutically acceptable adjuvant, diluent or carrier; and (ii) a formulation including one or more other active agents, in admixture with a pharmaceutically-acceptable adjuvant, diluent or carrier, which components (i) and (ii) are each provided in a form that is suitable for administration in conjunction with the other.

Component (i) of the kit of parts is thus component (A) above in admixture with a pharmaceutically acceptable adjuvant, diluent or carrier. Similarly, component (ii) is component (B) above in admixture with a pharmaceutically acceptable adjuvant, diluent or carrier. The one or more other active agents (i.e. component (B) above) may be, for example, any of the agents mentioned above in connection with the treatment of bacterial infection such as *Clostridium difficile* infection, autoimmune and/or inflammatory diseases such as IBD (e.g. Crohn's disease and/or ulcerative colitis). If component (B) is more than one further active agent, these further active agents can be formulated with each other or formulated with component (A) or they may be formulated separately. In one embodiment component (B) is one other therapeutic agent. In another embodiment component (B) is two other therapeutic agents. The combination product (either a combined preparation or kit-of-parts) of this aspect of the invention may be used in the treatment or prevention of an autoimmune disease (e.g. the autoimmune diseases mentioned herein).

Vectors and Hosts

The term "vector", as used herein, is intended to refer to a nucleic acid molecule capable of transporting another nucleic acid to which it has been linked. One type of vector is a plasmid, which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian and yeast vectors). Other vectors (e.g. non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g. replication defective retroviruses. adenoviruses and adeno-associated viruses), which serve equivalent functions, and also bacteriophage and phagemid systems. The invention also relates to nucleotide sequences that encode polypeptides of the invention. The term "recombinant host cell" (or simply "host cell"), as used herein, is intended to refer to a cell into which a recombinant expression vector has been introduced. Such terms are intended to refer not only to the particular subject cell but to the progeny of such a cell.

In one aspect of the invention there is provided a polynucleotide encoding a polypeptide of the invention. In a further aspect of the invention there is provided a vector comprising the polynucleotide or cDNA comprising said polynucleotide. In a further aspect of the invention there is provided a host cell transformed with said vector, which is capable of expressing the polypeptide of the invention. Suitably the host cell is a mammalian cell, a plant cell, a yeast cell such as a yeast cell belonging to the genera *Aspergillus, Saccharomyces, Kluyveromyces, Hansenula* or *Pichia*, such as *S. cerevisiae* or *P. pastoris*; or a bacterial cell such as *E. coli*.

Preparative Methods

Polypeptides of the invention can be obtained and manipulated using the techniques disclosed for example in Green and Sambrook 2012 *Molecular Cloning: A Laboratory Manual* 4$^{th}$ Edition Cold Spring Harbour Laboratory Press. Suitably the substitutions made to the polypeptide of the invention, or substitutions made in the methods of the invention, are introduced synthetically. Suitably, the substitutions are not introduced by V(D)J recombination or somatic mutation.

In particular, artificial gene synthesis may be used to produce a polypeptide according to the invention (Nambiar et al 1984 *Science* 223:1299-1301, Sakamar and Khorana 1988 *Nucl. Acids Res* 14:6361-6372, Wells et al 1985 *Gene* 34:315-323 and Grundstrom et al 1985 *Nucl. Acids Res* 13:3305-3316, herein incorporated by reference in their entirety). A gene encoding a polypeptide of the invention can be synthetically produced by, for example, solid-phase DNA synthesis. Entire genes may be synthesized de novo, without the need for precursor template DNA. To obtain the desired oligonucleotide, the building blocks are sequentially coupled to the growing oligonucleotide chain in the order required by the sequence of the product. Upon the completion of the chain assembly, the product is released from the solid phase to solution, deprotected, and collected. Products can be isolated by high-performance liquid chromatography (HPLC) to obtain the desired oligonucleotides in high purity (Verma and Eckstein 1998 *Annu Rev Biochem* 67:99-134).

The constructs of the invention may be fused genetically at the DNA level i.e. a polynucleotide construct which encodes the complete construct comprising one or more polypeptides. One way of joining multiple polypeptides via the genetic route is by linking the polypeptide coding sequences via a labile peptide linker coding sequence. For example, the carboxy-terminal end of the first polypeptide may be linked to the amino-terminal end of the next polypeptide via a labile peptide linker coding sequence. This linking mode can be extended in order to link polypeptides for the construction of tri-, tetra-, etc. functional constructs. A method for producing multivalent (such as bivalent) VHH polypeptide constructs is disclosed in WO96/34103 (herein incorporated by reference in its entirety).

Mutations can be made to the DNA or cDNA that encode polypeptides which are silent as to the amino acid sequence of the polypeptide, but which provide preferred codons for translation in a particular host. The preferred codons for translation of a nucleic acid in, e.g., *E. coli* and *S. cerevisiae*, are known.

Mutation of polypeptides can be achieved for example by substitutions, additions or deletions to a nucleic acid encoding the polypeptide. A substitution is the replacement of a residue with a different residue in the same, corresponding location. The substitutions, additions or deletions to a nucleic acid encoding the polypeptide can be introduced by many synthetic methods, including for example error-prone PCR, shuffling, oligonucleotide-directed mutagenesis, assembly PCR, PCR mutagenesis, in vivo mutagenesis, cassette mutagenesis, recursive ensemble mutagenesis, exponential ensemble mutagenesis, site-specific mutagenesis (Ling et al 1997 *Anal Biochem* 254(2):157-178, herein incorporated by reference in its entirety), gene reassembly, Gene Site Saturation Mutagenesis (GSSM), synthetic ligation reassembly (SLR) or a combination of these methods. The modifications, additions or deletions to a nucleic acid can also be introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, ensemble mutagenesis, chimeric nucleic acid multimer creation, or a combination thereof.

Expression of polypeptides comprising immunoglobulin chain variable domains such as VHs and VHHs can be achieved using a suitable expression vector such as a prokaryotic cell such as bacteria, for example *E. coli* (for example according to the protocols disclosed in WO94/04678 and WO96/34103, which are incorporated herein by reference). Expression of immunoglobulin chain variable domains such as VHs and VHHs can also be achieved using eukaryotic cells, for example insect cells, CHO cells, Vero cells or suitably yeast cells such as yeasts belonging to the genera *Aspergillus, Saccharomyces, Kluyveromyces, Hansenula* or *Pichia*. Suitably *S. cerevisiae* is used (for example according to the protocols disclosed in WO94/025591, which is incorporated herein by reference).

Suitably, a polypeptide of the invention can be produced in a fungus such as a yeast (for example, *S. cerevisiae*) comprising growth of the fungus on a medium comprising a carbon source wherein 50-100 wt % of said carbon source is ethanol, according to the methods disclosed in WO02/48382.

CLAUSES

A set of clauses defining the invention and its preferred aspects is as follows:
1. A polypeptide comprising an immunoglobulin chain variable domain comprising three complementarity determining regions (CDR1-CDR3) and four framework regions, wherein:
   (a) at least one lysine residue in CDR1, CDR2 and/or CDR3 has been substituted with at least one histidine residue,
   and/or
   (b) at least one arginine residue in CDR1, CDR2 and/or CDR3 has been substituted with at least one histidine residue;
   wherein the polypeptide has increased intestinal stability relative to a corresponding
   polypeptide not having said histidine substitutions.
2. A method of increasing the intestinal stability of a polypeptide comprising an immunoglobulin chain variable domain, wherein the immunoglobulin chain variable domain comprises three complementarity determining regions (CDR1-CDR3) and four framework regions, wherein the method comprises the step of substituting:
   (a) at least one lysine residue in CDR1, CDR2 and/or CDR3 with at least one histidine residue,
   and/or
   (b) at least one arginine residue in CDR1, CDR2 and/or CDR3 with at least one histidine residue.
3. A method of making a polypeptide comprising an immunoglobulin chain variable domain, wherein the immunoglobulin chain variable domain comprises three complementarity determining regions (CDR1-CDR3) and four framework regions, wherein the method comprises the step of substituting:
   (a) at least one lysine residue in CDR1, CDR2 and/or CDR3 with at least one histidine residue,
   and/or
   (b) at least one arginine residue in CDR1, CDR2 and/or CDR3 with at least one histidine residue
   wherein the polypeptide has increased intestinal stability relative to a corresponding polypeptide not having said histidine substitutions.
4. The polypeptide, method of increasing the intestinal stability of a polypeptide or method of making a polypeptide according to any one of clauses 1 to 3, wherein the substitutions increase the stability of the polypeptide in the intestinal tract, such as in the small and/or large intestine, such as in the duodenum, jejunum, ileum cecum, colon, rectum and/or anal canal, relative to a corresponding polypeptide not having said histidine substitutions.
5. The polypeptide, method of increasing the intestinal stability of a polypeptide or method of making a polypeptide according to any one of clauses 1 to 4, wherein the substitutions increase the stability of the polypeptide in a model of the intestinal tract, such as in the small and/or large intestine, such as in the duodenum, jejunum, ileum cecum, colon, rectum and/or anal canal, relative to a corresponding polypeptide not having said histidine substitutions.
6. The polypeptide, method of increasing the intestinal stability of a polypeptide or method of making a polypeptide according to clause 5 wherein the model of the intestinal tract is the Standard Human Faecal Supernatant Intestinal Tract Model.
7. The polypeptide, method of increasing the intestinal stability of a polypeptide or method of making a polypeptide according to clause 6, wherein the stability of the polypeptide, as determined by the Standard TNFR2/TNF Interference ELISA Assay when the immunoglobulin chain variable domain is an anti-TNF-alpha immunoglobulin chain variable domain, or the Standard gp130 ELISA Assay when the immunoglobulin chain variable domain is an anti-IL-6R immunoglobulin chain variable domain, is increased by at least 1%, more suitably 5%, more suitably 10%, relative to a corresponding polypeptide not having said histidine substitutions, after 16 hours incubation in the Standard Human Faecal Supernatant Intestinal Tract Model.
8. The polypeptide, method of increasing the intestinal stability of a polypeptide or method of making a polypeptide according to any one of clauses 1 to 7, wherein the substitutions increase the stability of the polypeptide to one or more proteases produced in the small or large intestine, relative to a corresponding polypeptide not having said histidine substitutions.
9. The polypeptide, method of increasing the intestinal stability of a polypeptide or method of making a polypeptide according to any one of clauses 1 to 8 wherein the potency of the polypeptide is substantially the same as the potency of a corresponding polypeptide not having said histidine substitutions.
10. The polypeptide, method of increasing the intestinal stability of a polypeptide or method of making a polypeptide according to any one of clauses 1 to 9, wherein the at least one lysine and/or arginine residue is present in a window defined as the second third of CDR1 and/or the second third of CDR2 and/or the second third of CDR3.
11. The polypeptide, method of increasing the intestinal stability of a polypeptide or method of making a polypeptide according to clause 11, wherein each lysine and/or arginine residue in CDR1, CDR2 and/or CDR3 has been substituted with one histidine residue each.
12. The polypeptide, method of increasing the intestinal stability of a polypeptide or method of making a polypeptide according to any one of clauses 1 to 12, wherein the polypeptide is an antibody, a modified antibody containing additional antibody binding regions or an antibody fragment such as an scFv, a Fab fragment, a F(ab')2 fragment or an immunoglobulin chain variable domain such as a VHH, a VH, a VL, a V-NAR.
13. The polypeptide, method of increasing the intestinal stability of a polypeptide or method of making a polypeptide according to any one of clauses 1 to 12, wherein the polypeptide binds to a target accessible via the intestinal tract.
14. A pharmaceutical composition comprising the polypeptide or construct according to any one of clauses 1 to 13 for use as a medicament for oral administration.
15. The pharmaceutical composition according to clause 14, wherein the composition is presented in enterically coated form.

Further Clauses

A set of further clauses defining the invention and its preferred aspects is as follows. The features recited in the claims recited below optionally apply mutatis mutandis to these further clauses 1 to 3.
1. A polypeptide comprising a region which is capable of binding a target with high affinity, wherein:
   (a) at least one lysine residue in the region has been substituted with at least one histidine residue, and/or
   (b) at least one arginine residue in the region has been substituted with at least one histidine residue;
   wherein the polypeptide has increased intestinal stability relative to a corresponding polypeptide not having said histidine substitutions.
2. A method of increasing the intestinal stability of a polypeptide comprising a region which is capable of binding a target with high affinity, wherein the method comprises the step of substituting:
   (a) at least one lysine residue in the region with at least one histidine residue, and/or
   (b) at least one arginine residue in the region with at least one histidine residue.
3. A method of making a polypeptide comprising a region which is capable of binding a target with high affinity, wherein the method comprises the step of substituting:
   (a) at least one lysine residue in the region with at least one histidine residue, and/or
   (b) at least one arginine residue in the region with at least one histidine residue,
   wherein the polypeptide has increased intestinal stability relative to a corresponding polypeptide not having said histidine substitutions.

The present invention will now be further described by means of the following non-limiting examples.

EXAMPLES

Example 1: Standard Intestinal Tract Models, Standard Intestinal Stability Assays and Standard Potency Assays The intestinal stability and potency of a polypeptide comprising an immunoglobulin chain variable domain can be assayed using the following methods. The methods below refer to ICVDs, but are equally applicable to any polypeptide which comprises an ICVD, such as an antibody.

1.1 Standard Intestinal Tract Models

Ex vivo samples from human faeces and mouse small intestine samples are highly relevant matrices for estimation of stability in the human intestinal tract. Such samples contain native host-produced, and associated microbial-produced, proteases along with any chaotropic agents or surfactants that may influence ICVD stability in the presence of proteases. The enzymatic cleavage sites of at least some proteases present in the small intestine from murine and human origin are well characterised and conserved between the two species. Murine small intestinal supernatants were found to be a particularly stringent challenge in terms of total protease activity by comparison to small intestinal samples from pigs and clinically-derived human lavage samples of the small intestine.

The intestinal tract models detailed below, which utilise ex vivo samples from human faeces and mouse small intestine, therefore allow one to assay the stability of a polypeptide comprising an ICVD in an environment which is highly representative of the conditions of the intestinal tract. The percentage of viable ICVD remaining after incubation is assessed after incubation in an intestinal tract model using an appropriate assay such as the Standard Western Blot Stability Assay (for assaying proportions of intact ICVD) or the Standard TNFR2/TNF Interference ELISA Assay or Standard Toxin ELISA Assay (both for assaying proportions of functional ICVD).

Note that from the point of sampling from mouse or human up to the point of use in an ICVD stability assay, all faecal/intestinal samples, slurries and supernatants should be kept chilled on ice or manipulations such as centrifugation carried out at 4° C. Once generated, supernatant samples may be frozen at −80° C. and thawed once (or twice) before use. Repeat freeze-thawing is likely to result in loss of protease stability. Prolonged storage (>1 year) at −80° C. does not appear to reduce total protease activity. However, slurries and supernatants should be monitored on a case-by-case basis over time.

1.1.1 The Standard Human Faecal Supernatant Intestinal Tract Model

Faecal Supernatant Pool Production

To generate supernatants for stability testing, Ix PBS is added to faecal samples at a ratio of 1 or 2 mLs 1×PBS per gram of faeces. The samples are then vortexed to homogeneity. The resulting material is referred to as a faecal slurry (in the case of a very limited number of particularly firm samples used in the examples below, it was necessary to add 3 mLs 1×PBS per gram faeces in order to generate a homogenous faecal slurry). To generate supernatants for testing, slurries are centrifuged at 4.5 k rpm or 13.5 k rpm (4° C.) for 1-5 minutes to remove the bulk of the solid material and all cellular material. The supernatant from the first spin is then re-centrifuged at 13.5 k rpm (4° C.) for 5 minutes, leaving only the soluble fraction, including proteases. Supernatants from multiple individuals are pooled together such that each pool represents the combined protease output from the faeces of multiple individuals.

For the purposes of the worked examples below, hospital-derived human faecal samples were obtained (and the presence of C. difficile in the samples was established), before supernatant pools were then generated as described above. The pools were characterised according to Table 1.

TABLE 1

| ID | Individuals per pool | Clostridium difficile status |
| --- | --- | --- |
| Pool 2 | 2 | Toxin Negative by Vero Cell Cytotox Assay |
| Pool 3 | 5 | Toxin Positive by Vero Cell Cytotox Assay |
| Pool4 | 5 | Toxin Negative by Vero Cell Cytotox Assay |

Performing the Assay

Prepare 20× protease inhibitor solution by adding 1 tab of Sigmafast Protease Inhibitor Cocktail (Sigma S8830, containing AEBSF (4-(2-Aminoethyl) benzenesulfonyl fluoride, Bestatin, E-64, Pepstatin A, Phosphoramidon, Leupeptin, Aprotinin) to 5 mL protease stop buffer (1×PBS, 2% BSA, 5 mM EDTA). This solution may be stored for 2 weeks at 2-8 degrees C. On the day of the assay, briefly vortex the supernatant matrix to ensure homogeneity. Prepare all reactions on ice and keep chilled until the assay is first incubated.

Prepare 2× protease stop solution by diluting 20× protease inhibitor solution in protease stop buffer and adding PMSF to a concentration of 1 mM in the 2× stop buffer (1/100 dilution of 0.1 M solution Sigma 93482). Keep this solution chilled on ice at all times before use.

Prepare ICVD (or antibody) solutions at 250 µg/mL in 0.1% BSA. On ice, in thin-walled PCR tubes or plates, dilute the 250 µg/mL ICVD into the supernatant matrix to give a final ICVD concentration (at time zero) of 20 µg/mL. Mix the resulting solution on ice by pipetting, ensuring the solution does not warm up. Once homogenous, immediately remove one volume of the sample matrix plus 20 µg/mL ICVD and mix with an equal volume of 2× protease stop solution. Mix the stopped matrix solution on ice and immediately freeze at −80 degrees C. This is the time zero sample. Incubate the remaining test matrix sample plus 20 µg/mL ICVD at 37 degrees C. in a PCR machine or similar apparatus. At the required timepoints repeat the procedure above to generate stopped supernatant samples for comparison to the time zero sample. In addition, generate a protease-stopped matrix control that does not contain ICVD by adding one volume of matrix sample (containing no ICVD) from time zero with an equal volume of 2× protease stop solution. This will be used as a control in downstream analysis to assess the effect of the matrix on, for example, ELISAs or western blotting profiles.

Following measurement using the Standard Western Blot Stability Assay, the Standard TNFR2/TNF Interference ELISA Assay or the Standard Toxin ELISA Assay, the amount of viable ICVD remaining after incubation in a matrix sample at a given timepoint is divided by the amount present at the zero timepoint. The resulting figure is then multiplied by 100 to give % stability. In the case of the Standard Western Blot Stability Assay, this provides proportion of intact ICVD. In the case of the Standard TNFR2/TNF Interference ELISA Assay or the Standard Toxin ELISA Assay, this provides the proportion of functional ICVD.

1.1.2 The Standard Mouse Small Intestinal Supernatant Intestinal Tract Model
Faecal Supernatant Pool Production C57BL/6 ('black 6') mice are sacrificed. The small intestine, including the full duodenum, jejunum and ileum are excised from the body cavity of mice carefully so as to minimise unnecessary tissue damage. The solid contents of the small intestine are collected and the internal surface of the small intestine flushed with 1 mL 0.9% saline (to preserve the native pH of the intestinal contents). The 1 mL intestinal washout solution and intestinal contents samples are then mixed together and homogenised fully by vortexing to generate a small intestinal slurry. To generate supernatants for testing, slurries are centrifuged at 13.5 k rpm (4° C.) for 2 minutes to remove the bulk of the solid material and all cellular material. The supernatant from the first spin are then re-centrifuged at 13.5 k rpm (4° C.) for 5 minutes, leaving only the soluble fraction, including proteases. Supernatants from multiple mice (5 on average per pool) are mixed together such that each pool represents the combined protease output from the small intestine of multiple mice.

In the examples below, it was found that different pools of mouse small intestinal supernatant used over time demonstrated similar proteolytic activity.

Performing the Assay

The supernatants are used in the same manner as described above under The Standard Human Faecal Supernatant Intestinal Tract Model under 'Performing the Assay'.

1.2 The Standard Western Blot Stability Assay
For Assessment of Percentage Viable ICVD Remaining after Incubation in an Intestinal Tract Model
Preparation of Samples for SDS-PAGE (Under Reducing Conditions):

1) Prepare sample buffer for reducing SDS-PAGE: Add reducing agent 0.5M Dithiothreitol (DTT) (Novex NP0004) to Novex 4×LDS sample buffer (NP0007) in a ratio of 1:9. For example, add 10 µL 0.5M DTT to 90 µL of 4× sample buffer. The resulting solution will be referred to as '4× load dye' from this point forward.
2) 1× load dye may be prepared by diluting the 4× load dye stock 1:3 with sterile $H_2O$.
3) Add 15 µL of each ICVD-containing experimental sample in digestive matrix, from time zero or 30 minutes, to 5 µL 4× load dye. Aim to load a final amount of 100-200 ng ICVD from the stopped zero timepoint. Match the volume of sample from the 30 minute timepoint to the volume added for the zero timepoint, so that any loss/degradation of ICVD over time is evident by eye on the final blot (the same applies for other timepoints such as 15 minute, 1 hour, 2 hour, etc, which may also be used). If possible, include un-treated standards of the test ICVD (at 100 and 10 ng) to confirm that the transfer and detection systems are performing correctly.
4) Heat all samples containing ICVD to 95° C. for 5-10 minutes (treat all samples equally) to denature the proteins and coat them with LDS present in the load dye. Allow the samples to cool, spin them down briefly in a centrifuge to collect all of the liquid.
5) Prepare a suitable reference ladder that can be visualised following blotting (Super Signal MW protein Ladder (Pierce)). Add 6.5 µL of protein ladder+13 µL Ix load dye. Note that the reference ladder does not need to be heated before gel loading (see supplier's instructions).

Electrophoresis

Use a Novex 10% Bis-Tris gel (NP0302Box) in combination with Ix SDS-MES running buffer (Novex NP0002-02) to visualise ICVDs by SDS-PAGE.

1) Prepare a Ix SDS-MES solution (from Novex NP0002-02, 20× stock) and assemble a Novex 10% Bis-Tris gel in an appropriate electrophoresis tank.
2) Load 15 µL of the samples prepared above per lane of the gel using gel loading pipette tips.
3) Run the gel at 200V until the dye front reaches the edge of the gel, but no further.

Blotting

1) Following electrophoresis, transfer proteins onto nitrocellulose membranes (IB3010, Invitrogen) using an iblot semi-dry transfer apparatus (Invitrogen, 7 minute semi-dry transfer program 3).
2) Block the membrane by incubating with 25 mL block solution (1% BSA, 2% Marvel, 0.05% Tween20, 1×PBS pH7.4) for 2 hours rocking gently at room temperature.
3) For the primary detection antibody, prepare a 1/1000 dilution of pAb 1952 Rabbit α-VHH (raised at Eurogentech using a VHH immunogen—another pAb rabbit a-ICVD, such as a pAb rabbit α-VH, could also be used) in block solution (1% BSA, 2% Marvel, 0.05% Tween20, 1×PBS pH7.4). Incubate the blot with 25 mL of this solution rocking gently at 4° C. overnight.
4) The following day, place the blot into 25 mL PBST (1×PBS, 0.1% Tween20) and incubate on a rocker for 5 minutes at room temperature. Repeat this procedure 5 times, each time using a fresh volume of PBST to wash off any non-specifically bound primary antibody. Complete 6 washes in total.
5) For the secondary detection antibody, prepare HRP-conjugated pAb Swine α-Rabbit (Dako, P0217) at a dilution of 1/1000 in block solution. Add normal goat serum (Dako) to this solution to a final concentration of 1% (for example 500 µL goat serum in 50 mL of secondary antibody solution). Incubate the blot with 25 mL of this solution for 2 hours rocking gently at room temperature.
6) Place the blot into 25 mL PBST (1×PBS, 0.1% Tween 20) and incubate on a rocker for 5 minutes. Repeat this procedure 5 times, each time using a fresh volume of PBST, to wash off any non-specifically bound secondary antibody. Complete 6 washes in total.
7) To develop the blot, incubate with 2 mL SuperSignal West Pico Chemiluminescent (ECL, Pierce 34087) for 1-2 minutes, ensuring that the full surface of the blot is covered in substrate
8) Visualise the ICVD present on the blot using an ImageQuant LAS4000 machine or equivalent, 5-10 minutes exposure. Vary the exposure time used to obtain the best ICVD signal. Band densities are determined using ImageQuant TL software or equivalent.

The amount of viable ICVD in a matrix sample at a given timepoint is divided by the amount present at the zero timepoint. The resulting figure is then multiplied by 100 to give % stability.

1.3 The Standard Toxin ELISA Assay

For Assessing the Potency of an Anti-TcdA or Anti-TcdB ICVD and for Assessment of Percentage Viable Anti-TcdA or Anti-TcdB ICVD Remaining after Incubation in an Intestinal Tract Model.

Materials:
  96-well, Flat-Bottomed, Nunc Maxisorp Immunoplates
  Recombinant, N-terminally His10-tagged, *Clostridium difficile* TcdB cell binding domain (CBD-B) from strain R20291 (ribotype 027) in 1×PBS. This protein was cloned, expressed from *E. coli*, and His-tag purified by FPLC.
  Purified, full-length *Clostridium difficile* toxin A from strain VP110463 (ribotype 087). Bacteria grown in static, anaerobic cultures and secreted TcdA purified by FPLC ion exchange chromatography.
  Anti-VHH Polyclonal Rabbit antibody: 6CP (equivalent anti-ICVD, such as anti-VH polyclonal rabbit antibodies could also be used).
  Swine anti-rabbit polyclonal immunoglobulins—HRP conjugated (Dako, P0217)
  Supersensitive TMB for ELISA: Sigma (T4444)
  0.5M Sulphuric Acid
  Block buffer: 1% BSA in Ix PBS (pH 7.2-7.5).
  Block buffer plus 2× Protease inhibitor (1% BSA in Ix PBS, pH 7.3-7.5, 2× protease inhibitor cocktail, 2.5 mM EDTA, 0.5 mM PMSF).
  PBST: 1×PBS plus 0.05% Tween 20.

Block buffer plus 2× Protease inhibitor is used as the assay diluent to prepare ICVD solutions prior to addition to the ELISA plate, when the ICVD sample is present in a digestive matrix such as mouse small intestinal supernatant or human faecal supernatant that may otherwise interfere with the performance of the ELISA. 1/200 dilution of 0.1 M PMSF solution Sigma 93482 can be used to achieve 0.5 mM PMSF. EDTA must also be added to a final concentration of 2.5 mM. Sigmafast protease Inhibitor cocktail (Sigma S8830, contains AEBSF (4-(2-Aminoethyl) benzenesulfonyl fluoride, Bestatin, E-64, Pepstatin A, Phosphoramidon, Leupeptin, Aprotinin) is used in this buffer. A stock of 20× protease inhibitor solution can be made by adding 1 tab of Sigmafast Protease Inhibitor Cocktail (Sigma S8830) to 5 mL protease stop buffer (1×PBS, 2% BSA, 5 mM EDTA). This solution may be stored for 2 weeks at 2-8° C. and diluted into block buffer on the day of the ELISA.

Anti-TcdA ICVD Detection by ELISA

This assay is designed to test anti-TcdA specific ICVDs for their ability to bind to *Clostridium difficile* toxin A bound to an ELISA plate. The plate coating toxin for this assay is full-length TcdA VP110463 (087).

Method:
1. Dilute *C. difficile* TcdA in 1×PBS to make a 2 µg/mL coating solution. Add 50 µL of this per well of a Nunc Maxisorp plate, seal the plate and incubate overnight at 2-8° C. Do not prepare large numbers of plates (over 3) with the same stock of 2 µg/mL solution TcdA.
2. Wash the plate×4 with 380 µL PBST with a plate washer. Tap the plate out to ensure minimal residue is left.
3. Add 200 µL per well of block buffer, seal and leave to incubate at room temperature for at least an hour shaking. Plates can also be left to block overnight at 2-8° C. if necessary.
4. Prepare a serial dilution series of ICVD reference standard using block buffer, or block buffer plus 2× Protease inhibitor if the main assay samples are from a digestive matrix, as a diluent. The dilution range should be adjusted based on the binding of each ICVD tested such that it covers the full assay signal range, from the background signal to saturation, with the linear range well-defined. Prepare a sufficient volume of each dilution to plate 50 µL in triplicate
5. Prepare appropriate dilutions of ICVD-containing samples to be tested in block buffer, or block buffer plus 2× protease inhibitor if the samples are from a digestive matrix, as a diluent. Prepare dilutions such that their estimated concentration will fall in the linear range of assay detection. The dilution range should be adjusted based on the binding of each ICVD tested. These dilutions should also be made serially in a microplate such that there is sufficient volume for triplicate 50 µL replicates on the final ELISA plate. Include an assay blank (no ICVD). For digest analysis ELISAs, include a protease inhibitor—stopped time zero matrix control (containing no ICVD) to check for background signal in the assay. This should be diluted in Block buffer plus 2× protease inhibitor and should match the top concentration of matrix that contains an ICVD sample tested on the plate. Keep samples chilled during preparation if they are prepared from a digestive matrix. Prepare enough of each sample to add to the plate in triplicate at 50 µL/well
6. Remove the Block buffer on the ELISA plate to waste, tap out any residual onto a paper towel and add 50 µL of diluted sample to each well. Include 1) no matrix, no ICVD (blank wells) and 2) Matrix only (no ICVD) wells. Seal the plate and incubate at room temp, shaking for 2 hours.
7. Wash ×4 as per step 2.
8. Add 50 µL per well of rabbit anti-VHH PAb diluted to 1/2000 in block buffer, seal the plate and incubate at room temperature, shaking, for 1 hour.
9. Wash ×4 as per step 2.
10. Add 50 µL per well of Swine anti-rabbit-HRP diluted to 1/2000 using Block buffer, seal the plate and incubate at room temperature, shaking, for 1 hour.

11. Wash ×4 as per step 2.
12. Add 100 µL per well of TMB, seal the plate and incubate at room temperature for no longer than 30 minutes, shaking. The plate should be covered with silver foil as TMB is light sensitive.
13. Add 50 µL of 0.5 M sulphuric acid to each well and read the plate at 450 nm.
14. Use the ICVD standard calibration curve to interpolate unknown sample concentrations using GraphPad Prism software (or equivalent).

Anti-TcdB ICVD Detection by ELISA

This assay is designed to test anti-TcdB specific ICVDs for their ability to bind to *Clostridium difficile* TcdB Cell Binding Domain (CBD-B) bound to an ELISA plate. It is critical to check before running this assay that the ICVD being tested does not bind elsewhere on TcdB, otherwise no signal will be observed.

Method:

1. Dilute *C. difficile* CBD-B (027) in PBS to make a coating solution of 0.5-1 μg/mL. Add 50 μL of this per well of a Nunc Maxisorp plate, seal with film and incubate overnight at 2-8° C. Do not prepare large numbers of plates (over 3) with the same stock of 0.5-1 μg/mL CBD-B solution.
2. Add 200 μL per well of block buffer, seal and leave to incubate at room temperature for at least and hour shaking. Plates can also be left to block overnight at 2-8° C. if necessary.
3. Prepare a serial dilution series of ICVD reference standard using block buffer, or block buffer plus 2× Protease inhibitor if the main assay samples are from a digestive matrix, as a diluent. The dilution range should be adjusted based on the binding of each ICVD tested such that it covers the full assay signal range, from the background signal to saturation, with the linear range well-defined. Prepare a sufficient volume of each dilution to plate 50 μL in triplicate
4. Prepare appropriate dilutions of ICVD-containing samples to be tested in block buffer, or block buffer plus 2× protease inhibitor if the samples are from a digestive matrix, as a diluent. Prepare dilutions such that their estimated concentration will fall in the linear range of assay detection. The dilution range should be adjusted based on the binding of each ICVD tested. These dilutions should also be made serially in a microplate such that there is sufficient volume for triplicate 50 μL replicates on the final ELISA plate. Include an assay blank (no ICVD). For digest analysis ELISAs, include a protease inhibitor—stopped time zero matrix control (containing no ICVD) to check for background signal in the assay. This should be diluted in Block buffer plus 2× protease inhibitor and should match the top concentration of matrix that contains an ICVD sample tested on the plate. Keep samples chilled during preparation if they are prepared from a digestive matrix. Prepare enough of each sample to add to the plate in triplicate at 50 μL/well
5. Remove the Block buffer on the ELISA plate to waste, tap out any residual onto a paper towel and add 50 μL of sample dilution to each well. Include 1) no matrix, no ICVD (blank wells) and 2) Matrix only (no ICVD) wells. Seal the plate and incubate at room temp, shaking for 2 hours.
6. Wash ×4 as per step 2.
7. Add 50 μL per well of rabbit anti-VHH pAb (or other ICVD equivalent) diluted to 1/2000 in block buffer, seal the plate and incubate at room temperature, shaking, for 1 hour.
8. Wash ×4 as per step 2.
9. Add 50 μL per well of Swine anti-rabbit-HRP diluted to 1/2000 using Block buffer, seal the plate and incubate at room temperature, shaking, for 1 hour.
10. Wash ×4 as per step 2.
11. Add 100 μL per well of TMB, seal the plate and incubate at room temperature for no longer than 30 minutes, shaking. The plate should be covered with silver foil as TMB is light sensitive.
12. Add 50 μL of 0.5 M sulphuric acid to each well and read the plate at 450 nm.
13. Use the ICVD standard calibration curve to interpolate unknown sample concentrations using GraphPad Prism software (or equivalent).

1.4 The Standard TNFR2/TNF Interference ELISA Assay

For Assessing the Potency of an Anti-TNF ICVD and for Assessment of Percentage Viable Anti-TNF ICVD Remaining after Incubation in an Intestinal Tract Model 1. Principle This assay detects binding of recombinant human TNF to the fusion protein, Enbrel (etanercept). This protein is comprised of soluble TNRF2 bound to the Fc region of human IgG, and can be used for capture of TNFα. This interaction can be competed for by anti-TNF ICVDs, causing reduced binding of TNFα to Enbrel. Bound TNF is then detected by an anti-hTNFα antibody. Therefore, high signal in this ELISA represents a low concentration of anti-TNF ICVD, and vice versa. Due to an overnight incubation step with the primary detection antibody, this assay usually takes approximately one and a half days to complete.

2. Materials

Solutions Required:

0.5 M Sulphuric acid ($H_2SO_4$)

1×PBS

PBST (Ix PBS, 0.05% Tween 20)

Block buffer (1% BSA in Ix PBS, pH 7.3-7.5)

Block buffer plus 2× Protease inhibitor (1% BSA in Ix PBS, pH 7.3-7.5, 2× protease inhibitor cocktail, 2.5 mM EDTA, 0.5 mM PMSF).

Block buffer plus 2× Protease inhibitor is used as the assay diluent to prepare ICVD and TNF solutions, prior to mixing and addition to the ELISA plate, when the ICVD sample is present in a digestive matrix such as mouse small intestinal supernatant or human faecal supernatant that may otherwise interfere with the performance of the ELISA. 1/200 dilution of 0.1 M PMSF solution Sigma 93482 can be used to achieve 0.5 mM PMSF. EDTA must also be added to a final concentration of 2.5 mM. Sigmafast protease Inhibitor cocktail (Sigma S8830, contains AEBSF (4-(2-Aminoethyl) benzenesulfonyl fluoride, Bestatin, E-64, Pepstatin A, Phosphoramidon, Leupeptin, Aprotinin) is used in this buffer. A stock of 20× protease inhibitor solution can be made by adding 1 tab of Sigmafast Protease Inhibitor Cocktail (Sigma S8830) to 5 mL protease stop buffer (1×PBS, 2% BSA, 5 mM EDTA). This solution may be stored for 2 weeks at 2-8° C. and diluted into block buffer on the day of the ELISA.

Reagents Required:
- Enbrel stock of known concentration (e.g. 2 mg/ml in PBS)
- Recombinant human TNF stock of known concentration (Life Technologies, Cat No PHC 3015) made up at 10 µg/ml in 1% BSA in PBS and kept at −80° C. in small (≤20 µl) aliquots
- Anti TNFα ICVD standard of known concentration
- Rabbit anti human TNFα antibody (Peprotech, 500-P31ABt, 300 µg/ml)
- ExtrAvidin HRP (Sigma, E2886)
- TMB substrate (Microwell Peroxidase substrate System 2-C, KPL, 50-70-00)

3. Procedure

Preparation:
Determine number of plates required for the assay. Coat Maxisorb 96-well ELISA plate (Nunc) with 50 µl/well 1 µg/ml Enbrel in 1×PBS. Shake plate briefly, seal and incubate at 4° C. overnight.

Assay:
1. Wash the ELISA plate using a plate washer (4×-380 µl PBST). Bang the plate on towel to remove residual liquid.
2. Apply 200 µl/well block buffer. Seal and incubate on a rotary plate shaker for ≥1 hour.
3. Prepare a serial dilution series of ICVD reference standards between 0.04 nM and 10 nM in minimum final volumes of 100 µl using block buffer, or Block buffer plus 2× Protease inhibitor if the main assay samples are from a digestive matrix, as a diluent. The dilution range should be adjusted based on the potency of each ICVD tested. Example shown in Table 2.

TABLE 2

| Dilution factor | Minimum volume of 10 nM ICVD needed (ul) | Dilution number | [Final solutions], (pM) | Volume to be transferred, (ul) | Volume diluent in each well (ul) |
|---|---|---|---|---|---|
| 2.545 | 280 | 1 | 10000.0 | 110 | 170 |
|  |  | 2 | 3928.571 |  |  |
|  |  | 3 | 1543.367 |  |  |
|  |  | 4 | 606.323 |  |  |
|  |  | 5 | 238.198 |  |  |
|  |  | 6 | 93.578 |  |  |
|  |  | 7 | 36.763 |  |  |

4. Prepare appropriate dilutions of ICVD-containing samples to be tested in block buffer, or block buffer plus 2× Protease inhibitor if the samples are from a digestive matrix, as a diluent. Prepare a serial dilution series. The dilution range should be adjusted based on the potency of each ICVD tested such that it covers the full assay signal range, from the background signal to saturation, with the linear range well-defined. These dilutions should also be made serially in a microplate such that there is sufficient volume for triplicate 50 µL replicates on the final ELISA plate. For digest analysis ELISAs, include a protease inhibitor—stopped time zero matrix control (containing no ICVD). This should be diluted in Block buffer plus 2× Protease inhibitor and should match the top concentration of matrix that contains an ICVD sample tested on the plate. Keep samples chilled during preparation if they are prepared from a digestive matrix.
5. Prepare a 5 ng/ml solution of hrTNFα in block buffer, or Block buffer plus 2× Protease inhibitor if the assay samples are from a digestive matrix.
6. In a separate 96-well plate, fill the blank well (for example, well H1) with block buffer or Block buffer plus 2× Protease inhibitor. Fill remaining relevant wells with 85 µl TNF solution.
7. Mix together 85 µl of each ICVD dilution from the preparation plate with 85 µl hrTNFα solution in the second plate. Include one well containing block buffer, or Block buffer plus 2× Protease inhibitor only (blank well). Include another well where hrTNFα is diluted with block buffer, or Block buffer plus 2× Protease inhibitor only (TNF only control well). Include a well where hrTNFα is diluted with 'stopped' digestive matrix, as described above. Seal, and incubate on a rotary plate shaker for 1 hour.
8. Wash blocked ELISA plate as in step 1.
9. Transfer 50 µl ICVD-TNF mixtures (plus appropriate controls; 1) no TNF, no ICVD, 2) TNF, but no ICVD 3) TNF plus 'stopped' digestive matrix, no ICVD) to washed ELISA plate in triplicate. Seal and incubate on a rotary plate shaker for 2 hours.
10. Wash blocked ELISA plate as in step 1.
11. Prepare 5 ml/plate 1/1000 dilution of anti human TNFα antibody (Peprotech, P31A) made up in block buffer. Add 50 µl/well, seal, shake on rotary plate shaker briefly, then incubate in cold room fridge (4° C.) overnight.

Note: This step can be reduced to 2h on the plate shaker at RT, but the signal will be reduced with consequent reduction in sensitivity. 12. Wash blocked ELISA plate as in step 1.
13. Prepare 5 ml/plate 1/1000 dilution of ExtrAvidin-linked HRP (Sigma, E2886). Add 50 µl/well, seal and incubate on a rotary plate shaker for ≥30 min.
14. Wash blocked ELISA plate as in step 1.
15. Prepare 10 ml/plate TMB substrate (1:1 ratio of substrate A and B). Add 100 µl/well, seal and incubate on a rotary plate shaker ≤30 mins. Shield from light.
16. Stop reaction with 50 µl/well 0.5 M $H_2SO_4$.
17. Read plate at 450 nm.
18. Use the ICVD standard calibration curve to interpolate unknown sample concentrations using GraphPad Prism software (or equivalent).

In Step 6, equal volumes of diluted ICVD and TNFα are mixed before addition to the ELISA plate. This step effectively dilutes by twofold the concentrations of ICVD and TNFα. Therefore, the final concentration of TNFα on the plate will be 2.5 ng/ml and the final concentration of the ICVD standard curve will be from 0.02 nM to 5 nM. This dilution should be accounted for when estimating appropriate sample dilution factors. The TMB substrate reaction may progress quickly. The colour of the plate should be checked periodically, and if a very bright blue colour appears before 30 mins, the reaction should be stopped since very high absorbance can lead to high background. Appropriate controls should include triplicate wells of: BSA only, no ICVD (i.e. 2.5 ng/ml TNFα only), and if desired, no TNFα (i.e. 5 nM ICVD only). For digestion analysis ELISAs, a no-ICVD matrix sample that has been stopped by the addition of 2× protease stop solution should be added to TNF. The lowest dilution (or highest concentration) of the background matrix in the control should match the lowest dilution (or highest concentration) of digestive matrix in the highest ICVD concentration mixed with TNF/applied to the plate.

1.5 The Vero Cell Cytotoxicity Standard Assay For Assessing the Potency of an Anti-Toxin ICVD Culture and Maintenance of Vero Cells Prior to Use Routine subculture of Vero cells can be achieved as follows:
1. Once a flask of cells has grown to full confluence, aspirate all cell culture medium and apply 2 ml 1× trypsin (dissolved in 0.02% EDTA, Sigma E8008). Once the trypsin has been applied work quickly to prevent loss of cells during washing.
2. Wash the first trypsin application over the surface of the cells and then fully aspirate to remove all traces of cell culture medium (any traces of serum from the medium will inhibit trypsin activity).
3. Apply 2 ml of trypsin and wash over the surface of the cells.
4. Remove approximately 1.5-1.7 ml of trypsin from the flask.
5. Tilt the flask so that the remaining 300-500 μL cover the Vero cells on the surface of the plate.
6. Incubate the cells at 37° C. 5% $CO_2$ for 10-12 minutes.
7. To stop trypsin activity add 10 ml Vero cell medium.
8. Resuspend the cells by gently jetting the suspension against the bottom of the flask with a pipette until the medium becomes cloudy (indicating dissipation of cell clumps). 3-4 times should be sufficient. Avoid excessive pipetting as this may harm the cells.
9. Add 0.2 to 0.5 ml of the cell suspension to 25-30 ml fresh Vero cell medium in a 75 $cm^2$ cell culture flask (Corning). Incubate the flask at 37° C. 5% $CO_2$ to allow growth of the cells to full confluence. This should occur in 3-5 days, depending on the inoculum volume and cell count. To obtain finer control over the process, cells may be enumerated using a haemocytometer, as outlined below, and added at a fixed inoculum to the medium. Once in a confluent state the cell monolayer should remain healthy for another 1-2 days without medium replacement. To prolong the life of the confluent monolayer for use it is often helpful to refresh ⅓-½ of the culture medium (do not replace all the medium as it will have been conditioned with cytokines from the growing Veros). The cells should be split before rounding and detachment starts to occur.

Preparing Plates for the Assay (Day −1)

Ideally, plates should be prepared the day before use in the cytotoxicity assay. However, plates may also be prepared on the day of use if necessary. If the latter is the case, prepare plates in the morning (for use in the afternoon) and ensure that at least 3 hours are allowed for cell attachment to the microplate prior to use. A fully confluent flask of Vero cells should be used to make the cell suspension for plating.
1. Add 150 μl sterile $H_2O$ to the inter-well spaces and 300 μl to the top and bottom row of a 96-well flat bottomed microplate. This ensures that the cultured cells are hydrated during growth in the microplate.
2. Trypsinise and resuspend (in 10 ml Vero cell culture medium) a confluent flask of Vero cells, as described above.
3. Enumerate the cells using a haemocytometer and light microscope (take four independent counts and use the mean, for example using the four grid corners of a single haemocytometer slide). If there is any concern about cell viability following trypsinisation add Trypan blue dye to the cells before enumeration (1:1 v/v) and multiply the viable cell count ×2.
4. Dilute the cells to $5 \times 10^4$ cells/ml in the required volume (allow 8 ml per assay plate) of Vero cell culture medium.
5. Using a multichannel pipette, dispense 100 μl of the cell suspension into each well. This is equivalent to 5000 cells/well. If multiple plates are being prepared keep swirling and/or pipetting the cell suspension between consecutive platings to ensure that the cells are evenly distributed.
6. Centrifuge the microplate at 1,000 rpm for 2 minutes at room temperature to fix the cells evenly in place across the bottom of the plate. Spin 2 plates maximum in each arm of the centrifuge to avoid the arms tipping inward and spilling the inter-well water.
7. Visually confirm that cell distribution and number are as expected using a light microscope.
8. Incubate plates at 37° C. 5% $CO_2$.

Setting Up the Assay (Day 0)

Note: All solutions described in this section are prepared in Vero cell culture medium. You should calculate the required final volume of toxin and ICVD to cover the number of plates/combinations before starting the assay. Mix all solutions well (by vortexing and/or multiple inversions) between dilution steps.
1. Prepare the required volume of toxin at double (2×) the final assay concentration. The assay concentration required should be determined beforehand (see preliminary work, below).
2. Prepare the test ICVDs at double (2×) the top concentration to be tested in the assay. Aim for a top concentration of ICVD that will demonstrate a clear dose-response toxin neutralisation relationship in the assay (see example graph, below).
3. Prepare 10 serial dilutions (including the undiluted top concentration) of the 2×ICVD stock in a dilution trough. Typically, a 1/3 dilution produces a useful data range.
4. Use a 96-well round-bottom microplate to prepare mixed solutions before addition to the plates containing Vero cells.
5. In triplicate, prepare solutions of medium only, toxin only (Ix dilution) and Triton-X100 (0.01%) controls and add each to empty plate wells.
6. Attach 10 μl pipette tips to the central 6 rows of an 8-channel aspirator. Carefully remove all medium (around 100 μl per well) from the Vero cell microplate prepared on Day 0.
7. Using a multichannel pipette, add 100 μl from one row of the preparation plate to the cells on the assay plate. Repeat this twice to fill the two adjacent rows on the assay plate (3 replicate rows in total):
8. Once plate feeding is complete incubate at 37° C. for 3 days.

Processing the Assay (Day 3)
1. Observe the plates under a light microscope. Check for confluent growth in the medium only control wells and a good toxin response in the toxin-only control well.
2. Using a multichannel pipette, in the dark, add 10 μl Alamar blue reagent (light sensitive) to each well.
3. Shake the plate for 30 seconds to ensure mixing of the Alamar blue into the culture medium.
4. Incubate the plate for 1 hr 30 minutes at 37° C. 5% C02
5. Following incubation, in the dark, add 50 μl 3% SDS.
6. Read the plate using a plate reader (such as Fluostar Omega), excitation filter 544, emission filter 590, bottom optic. Set the blank (against which the data will be corrected) to the three plate wells treated with Triton X100.
7. Calculate the mean of three replicates for each treatment on the plate. Calculate % toxin neutralisation values using the formula: % Neutralisation=(ICVD treatment−toxin control)*100/(medium control−toxin control).

Preliminary Work: Determining the Optimal Amount of Toxin to Use in the Main Neutralisation Assay For ease of interpretation in the main assay, the appropriate concentration of toxin to use should be determined beforehand by conducting a toxin dose-response experiment on Vero cells. Prepare 10 serial dilutions of toxin in a 12 well dilution trough. Use the remaining two wells for 0.01% Triton and a medium only control. Prepare a minimum of 330 µL of each solution in the dilution trough (this allows three replicates at 100 µl each). If there is no indication of how potent the toxin preparation is in advance, choose a broad dilution range for the preliminary experiment. This can be repeated over a finer concentration range, if necessary. Apply these solutions to Vero cells in a flat-bottomed microplate, incubate and process the plate as described above.

To assay an ICVD, or full antibody, for neutralising activity against a given concentration of toxin, the minimum concentration of each toxin preparation capable of inducing the maximum reduction in cell viability is selected. An exemplary toxin dose-response curve on Vero cells is provided in FIG. 1. The horizontal bar indicates toxin concentrations suitable for use in the main neutralisation assay.

1.6 The Standard gp130 ELISA Assay

For Assessing the Potency of an Anti-IL-6R ICVD

The objective of this assay is to measure the potency of anti-IL-6R ICVDs by measuring interference in the binding to gp130 of a sIL-6/IL-6R complex. This assay detects binding of hIL-6R/hIL-6 complexes to recombinant human gp130. This interaction can be competitively inhibited by anti-IL-6R ICVDs, causing reduced binding of hIL-6R-hIL-6 complexes to gp130. Therefore, high signal in this ELISA represents a low concentration of anti-IL-6R ICVD, and vice versa.

Materials

Solutions Required:
  1×PBS
  PBST (1×PBS, 0.05% Tween 20)
  Block buffer (1% BSA in Ix PBS, pH 7.3-7.5)
  0.5 M Sulphuric acid ($H_2SO_4$)

Reagents Required:
  Recombinant soluble human gp130 at known concentration
  ICVD stock of known concentration
  Recombinant soluble human IL-6 at known concentration
  Recombinant soluble human IL-6R at known concentration
  Biotinylated goat anti-IL-6R polyclonal antibody (R&D systems BAF227); resuspended at 250 µg/ml in sterile PBS.
  ExtrAvidin-Peroxidase (Sigma E2886)
  TMB substrate (Microwell Peroxidase substrate System 2-C, KPL, 50-70-00)

Procedure

Preparation:
1. Determine number of plates required for the assay.
2. Prepare the relevant volume (up to 3 plates at a time) of 0.2 µg/ml recombinant soluble human gp130 in PBS with 5 µg/mL BSA in 1×PBS.
3. Working quickly, dispense 50 µl/well into Maxisorp 96-well ELISA plates (Nunc), loading a maximum of 3 plates in one batch.
4. Shake plate briefly, seal and incubate at 4° C. overnight.

Assay:
1. Wash the ELISA plate using a plate washer (4×-380 µl PBST). Bang the plate on towel to remove residual liquid.
2. Apply 200 µl/well block buffer. Seal and incubate on a rotary plate shaker for ≥1 hour.
3. Prepare a dilution series of ICVD standards between 0.004 nM to 80 nM in minimum final volumes of 70 µl using block buffer as a diluent.
4. Prepare appropriate dilutions of samples to be tested in block buffer, such that their estimated final concentration on the plate will fall in the range of 0.001 nM to 250 nM ICVD.
5. Prepare a 40 ng/ml IL-6R solution in block buffer.
6. In a separate 96-well plate, mix together 50 µl of each ICVD dilution with 50 µl IL-6R solution. In each dilution series include one well with no ICVD. Incubate for 1 hour on a rotary plate shaker.
7. Prepare a 100 ng/ml IL-6 solution in block buffer.
8. In a further additional 96-well plate, mix together 85 µl ICVD-IL-6R mixture from step 6 with 85 µl IL-6 solution prepared in step 7. Include wells containing block buffer only, such that the following controls are applied to each plate: IL-6 only, and no ICVD (IL-6+IL-6R only). Incubate for 10 minutes on rotary plate shaker.
9. Wash blocked ELISA plate as in step 1.
10. Transfer 50 µl of the mixtures prepared in step 8 to the washed ELISA plate in triplicate. Seal and incubate on a rotary plate shaker for 2 hours.
11. Wash blocked ELISA plate as in step 1.
12. Prepare 5.2 ml/plate 125 µg/mL of BAF227 anti-hIL-6R antibody made up in block buffer. Add 50 µl/well, seal, shake briefly, and incubate for 1 hour at room temperature or overnight at 4° C.
13. Wash blocked ELISA plate as in step 1.
14. Prepare 5.2 ml/plate of 1/1,000-1/3000 dilution of Extravidin in block buffer. Add 50 µl/well, seal, and incubate on a rotary shaker for 30 mins.
15. Wash blocked ELISA plate as in step 1.
16. Prepare 10 ml/plate TMB substrate (1:1 ratio of substrate A and B). Add 100 µl/well, seal and incubate on a rotary plate shaker until a mid blue colour evolves in the lowest dilution wells or up to a maximum of 30 mins. Shield from light.
17. Stop reaction with 50 µl/well 0.5 M $H_2SO_4$.
18. Read plate at 450 nm.
19. Use standard curve to interpolate concentrations of active ICVD. Raw OD450 values are adjusted with readings taken from blank control wells. Standard curves are plotted using appropriate software (e.g. Graphpad Prism using Log(inhibitor) vs. response—variable slope (four parameters)). ICVD concentrations in the test samples are calculated in the software using the standard curve.

For Assessment of Percentage Viable Anti-IL-6R ICVD Remaining after Incubation in an Intestinal Tract Model The objective of this assay is to measure the remaining concentration of active anti-IL-6R ICVDs which have previously been incubated in the presence of proteolytic material, such as mouse small intestinal supernatant or human faecal extract, thereby elucidating the impact on the ICVD of any proteolysis which may have taken place during incubation and therefore the proteolytic stability of the anti-IL-6R ICVDs. This assay detects binding of hIL-6R/hIL-6 complexes to recombinant human gp130. This interaction can be competitively inhibited by anti-IL-6R ICVDs, causing reduced binding of hIL-6R-hIL-6 complexes to gp130. Therefore, high signal in this ELISA represents a low concentration or low affinity of anti-IL-6R ICVD remaining active, and vice versa. The % survival is the percentage concentration of active ICVD, interpolated using the standard curve, maintained between a sample before and after digestion.

Materials
Solutions required:
1×PBS
1% BSA in PBS
PBST (1x PBS, 0.05% Tween 20)
Block buffer (1% BSA in 1x PBS, pH 7.3-7.5)
Assay buffer (1% BSA, 2×protease inhibitor* in 1x PBS)
0.5 M Sulphuric acid (H2SO4)
*2× protease inhibitor=1 tablet per 50 ml buffer Reagents Required:
Recombinant soluble human gp130 at known concentration
SigmaFast protease inhibitor tablets (S8820)
ICVD stock of known concentration
Soluble human IL-6 at known concentration
Soluble human IL-6R at known concentration
Biotinylated goat anti-IL-6R polyclonal antibody (R&D systems BAF227); resuspended at 250 µg/ml in sterile PBS.
ExtrAvidin-Peroxidase (Sigma E2886)
TMB substrate (Microwell Peroxidase substrate System 2-C, KPL, 50-70-00)

Procedure
Preparation:
1. Determine number of plates required for the assay.
2. Prepare the relevant volume (up to 3 plates at a time) of 0.2 µg/ml recombinant soluble human gp130 in PBS+5 µg/ml BSA.
3. Working quickly, dispense 50 µl/well into Maxisorp 96-well ELISA plates (Nunc), loading a maximum of 4 plates in one batch.
4. Shake plate briefly, seal and incubate at 4° C. overnight.

Assay:
1. Wash the ELISA plate using a plate washer (4×-380 µl PBST). Bang the plate on towel to remove residual liquid.
2. Apply 200 µl/well block buffer. Seal and incubate on a rotary plate shaker for ≥1 hour.
3. Prepare a dilution series of ICVD standards between 0.004 nM to 1000 nM in minimum final volumes of 70 µl using assay buffer as a diluent.
4. Prepare appropriate dilutions of samples to be tested in assay buffer, such that their estimated final concentration on the plate will fall in the range of 0.001 nM to 250 nM ICVD. Ensure that samples containing GI/faecal material are kept on ice as much as possible.
5. Prepare a 400 ng/ml IL-6 solution in assay buffer.
6. Prepare a 40 ng/ml IL-6R solution in assay buffer.
7. In a separate 96-well plate, mix together 50 µl of each ICVD dilution with 50 µl IL-6 solution. In each dilution series include one well with no ICVD.
8. In a further additional 96-well plate, mix together 85 µl ICVD-IL-6 mixture from step 7 with 85 µl IL-6R solution prepared in step 6. Include wells containing assay buffer only, such that the following controls are applied to each plate: IL-6 only, and no ICVD (IL-6+IL-6R only). Incubate for 5 minutes on rotary plate shaker.
9. Wash blocked ELISA plate as in step 1.
10. Transfer 50 µl of the mixtures prepared in step 8 to the washed ELISA plate in triplicate. Seal and incubate on a rotary plate shaker for 2 hours.
11. Wash blocked ELISA plate as in step 1.
12. Prepare 5 ml/plate 125 ng/mL of BAF227 anti-hIL-6R antibody made up in block buffer. Add 50 µl/well, seal, shake briefly, and incubate for 1 hour at room temperature or overnight at 4° C.
13. Wash blocked ELISA plate as in step 1.
14. Prepare 5 ml/plate 1/1000-1/3000 dilution of Extravidin in block buffer. Add 50 µl/well, seal, and incubate on a rotary shaker ≤30 mins
15. Wash blocked ELISA plate as in step 1.
16. Prepare 10 ml/plate TMB substrate (1:1 ratio of substrate A and B). Add 100 µl/well, seal and incubate on a rotary plate shaker until a mid blue colour evolves in the lowest dilution wells or up to a maximum of 30 mins. Shield from light.
17. Stop reaction with 50 µl/well 0.5 M $H_2SO_4$.
18. Read plate at 450 nm.
19. Use standard curve to interpolate concentrations of active ICVD. Raw OD450 values are adjusted with readings taken from blank control wells. Standard curves are plotted using appropriate software (e.g. Graphpad Prism using Log(inhibitor) vs. response—variable slope (four parameters)). ICVD concentrations in the test samples are calculated in the software using the standard curve. The active ICVD concentration in the test sample is expressed as a % of that in the 0 h sample to give % survival.

Example 2: Substitution of a Lysine Residue with Alanine, Histidine or Glutamine in CDR2 of an Anti-TNF-Alpha ICVD Q65B1 is an anti-TNF-alpha ICVD isolated, cloned and purified from a llama immunised with soluble human recombinant TNF-alpha. Residue K59 of the Q65B1 polypeptide sequence was substituted with alanine, histidine or glutamine and the impact of each substitution on intestinal tract stability and potency was tested.

DNA encoding each ICVD was cloned into vector pMEK222, expressed, and purified from the periplasm of *E. coli* (either by Talon or Nickel NTA column). All ICVDs tested here carry an identical C-terminal Flag-His6 tag.

Residue K59 resides in CDR2 of Q65B1. Q65B1 with a K59A substitution is labelled "ID43F", Q65B1 with a K59H substitution is labelled "ID8F-EV", and Q65B1 with a K59Q substitution is labelled "ID44F".

2.1.1 Potency—Standard TNFR2/TNF Interference ELISA Assay—Experiment 1

Dose-response curves of each ICVD were generated using the Standard TNFR2/TNF Interference ELISA Assay, which were used to generate EC50 values (FIG. 2A and Table 3).

TABLE 3

| Construct | Substitution | EC50 (pM) |
|---|---|---|
| Q65B1 | None (K59) | 98.4 |
| ID8F-EV | K59H | 139.3 |
| ID43F | K59A | 602.6 |
| ID44F | K59Q | 245.47 |

2.1.2 Potency—Standard TNFR2/TNF Interference ELISA Assay—Experiment 2

Figure 2B:
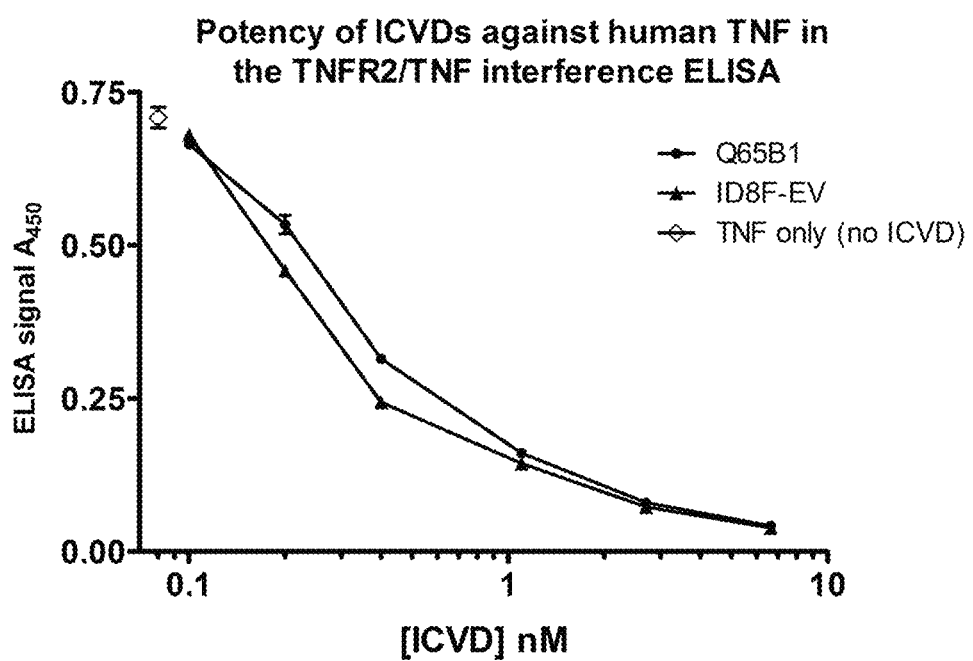

In a repeat experiment, dose-response curves of Q65B1 and ID8F-EV were generated again using the Standard TNFR2/TNF Interference ELISA assay (FIG. 2B).

2.2.1 Intestinal stability—Standard Mouse Small Intestinal Supernatant Intestinal Tract Model—Experiment 1

Figure 3A:
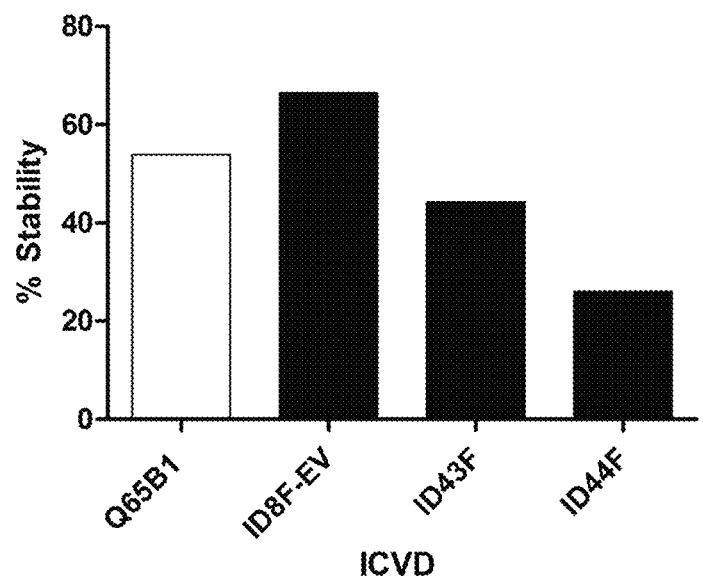

ICVDs were digested in mouse small intestinal material for 6 hours according to the Standard Mouse Small Intestinal Supernatant Intestinal Tract Model. Percentage stability of ICVDs was calculated using the Standard TNFR2/TNF Interference ELISA Assay. The results are shown in FIG. 3A.

2.2.2 Intestinal stability—Standard Mouse Small Intestinal Supernatant Intestinal Tract Model—Experiment 2

Q65B1 and ID8F-EV were digested in mouse small intestinal material for 16 hours according to the Standard Mouse Small Intestinal Supernatant Intestinal Tract Model. Percentage stability of ICVDs were calculated using the Standard TNFR2/TNF Interference ELISA Assay. The results are shown on the right hand side of FIG. 3B.

2.2.3 Intestinal stability—Standard Human Faecal Supernatant Intestinal Tract Model Q65B1 and ID8F-EV were digested for 16 hours in human faecal supernatant according to the the Standard Human Faecal Supernatant Intestinal Tract Model. Percentage stability of ICVDs were calculated using the Standard TNFR2/TNF Interference ELISA Assay. The results are shown on the left hand side of FIG. 3B.

2.3 Conclusion

K59A and K59Q reduced potency compared to K59 and K59H (see FIG. 2A, ID43F and ID44F vs Q65B1 and ID8F-EV, respectively). It can be seen from FIGS. 2A and 2B that any observed variation in the potency of ID8F-EV (K59H) relative to Q65B1 (K59) may be down to experimental variation and that these ICVDs have substantially the same potency.

K59A and K59Q reduced stability in mouse small intestinal material after 6 hours incubation, compared to K59 (see FIG. 3A, ID43F and ID44F vs Q65B1, respectively) and compared to K59H (see FIG. 3A, ID8F-EV).

Figure 3B:
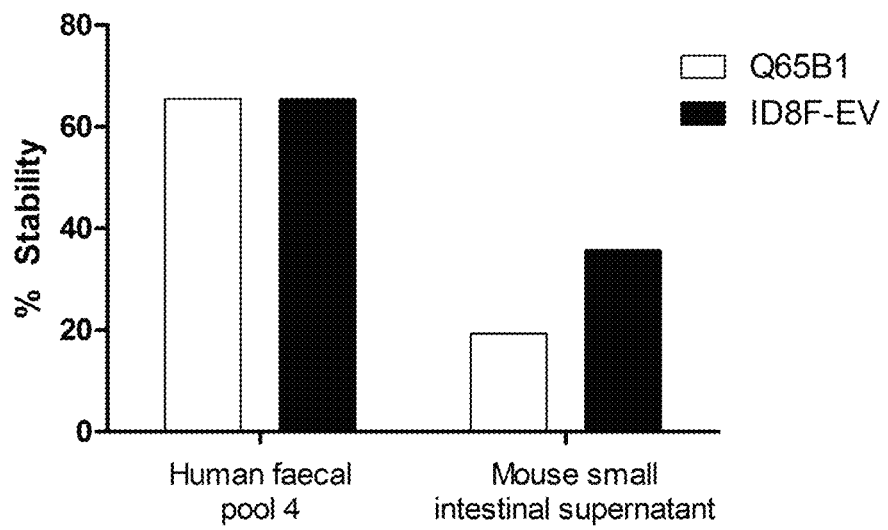

K59H increased stability in mouse small intestinal material after 6 hours and after 16 hours incubation, compared to K59 (see FIG. 3A and FIG. 3B, ID8F-EV vs Q65B1). ID8F-EV and Q65B1 were undifferentiated in stability after 16 hours incubation in this human faecal supernatant assay (FIG. 3B).

The stability increases of K59H were achieved without significantly compromising potency.

Example 3: Substitution of a Lysine Residue with a Histidine Residue in Both CDR2 and CDR3 of an Anti-TNF-Alpha ICVD Both residues K59 and K101 of Q65B1 were substituted with histidine (making "ID34F"). Residue K59 resides in CDR2 of Q65B1 and residue K101 resides in CDR3 of Q65B1. DNA encoding ID34F was cloned and expressed in yeast.

Q65B1 substituted with a K59H residue (as in Example 2) was produced again, having the same sequence as ID8F-EV described above. However, on this occasion DNA encoding this ICVD was cloned and expressed in yeast (therefore lacking the C-terminal Flag-His6 tag) and is therefore labelled "ID32F" in this example.

3.1 Potency—Standard TNFR2/TNF Interference ELISA Assay

Dose-response curves of each ICVD were generated using the Standard TNFR2/TNF Interference ELISA Assay. A concentration range of 0-3 nM was used (FIG. 4).

Figure 5A:
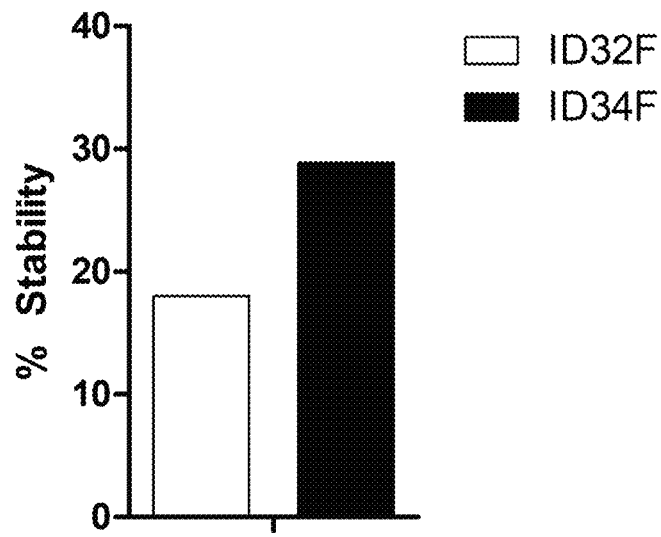

3.2.1 Intestinal stability—Standard Mouse Small Intestinal Supernatant Intestinal Tract Model ICVDs were digested for 16 hours in mouse small intestinal material according to the Standard Mouse Small Intestinal Supernatant Intestinal Tract Model. Percentage stability of ICVDs was calculated using the Standard TNFR2/TNF Interference ELISA Assay. The results are shown in FIG. 5A.

Figure 5B:
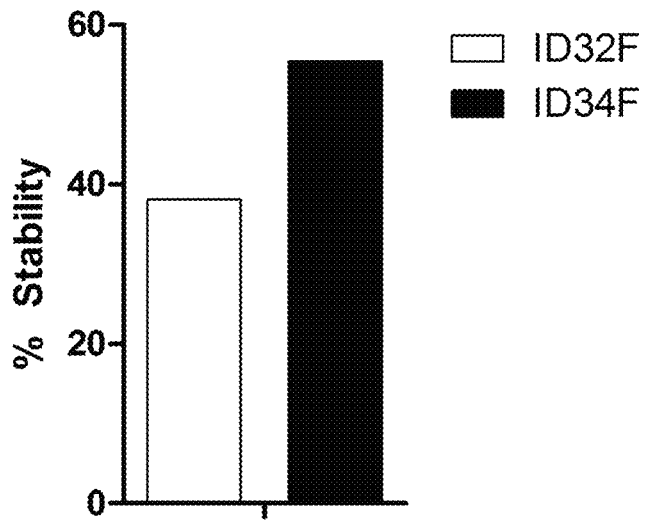

3.2.2 Intestinal Stability—Standard Human Faecal Supernatant Intestinal Tract Model ICVDs were digested for 16 hours in human faecal supernatant according to the Standard Human Faecal Supernatant Intestinal Tract Model. Percentage stability of ICVDs was calculated using the Standard TNFR2/TNF Interference ELISA Assay. The results are shown in FIG. 5B.

3.3 Conclusion

The additional K101H substitution in CDR3 of ID34F further increased intestinal stability of the ICVD according to both the Standard Mouse Small Intestinal Supernatant Intestinal Tract Model (FIG. 5A) and the Standard Human Faecal Supernatant Intestinal Tract Model (FIG. 5B), without significantly impacting potency (FIG. 4).

Example 4: Substitution of an Arginine Residue with an Alanine, Histidine, Glutamine, Phenylalanine or Tryptophan Residue in CDR3 of an Anti-TcdB ICVD ID45B is a modified anti-TcdB ICVD derived from a progenitor ICVD (Q31B1). Q31B1 was isolated, cloned and purified from a llama immunised with TcdB toxoids prepared by formalin inactivation of purified TcdB. Residue R107 of the ID45B polypeptide sequence was substituted with alanine, histidine, glutamine, phenylalanine or tryptophan and the impact of each substitution on intestinal stability and potency was tested.

DNA encoding each ICVD was cloned into vector pMEK222, expressed, and purified from the periplasm of *E. coli* (either by Talon or Nickel NTA column). All ICVDs tested here carry an identical C-terminal Flag-His6 tag.

Residue R107 resides in CDR3 of ID45B. The substituted ICVDs were labelled according to Table 4.

TABLE 4

| ICVD | Substitution |
| --- | --- |
| ID45B | None (R107) |
| ID46B | R107H |
| ID47B | R107A |
| ID48B | R107Q |
| ID49B | R107F |
| ID5OB | R107W |

4.1 Potency—Vero Cell Cytotoxicity Standard Assay

Figure 6A:
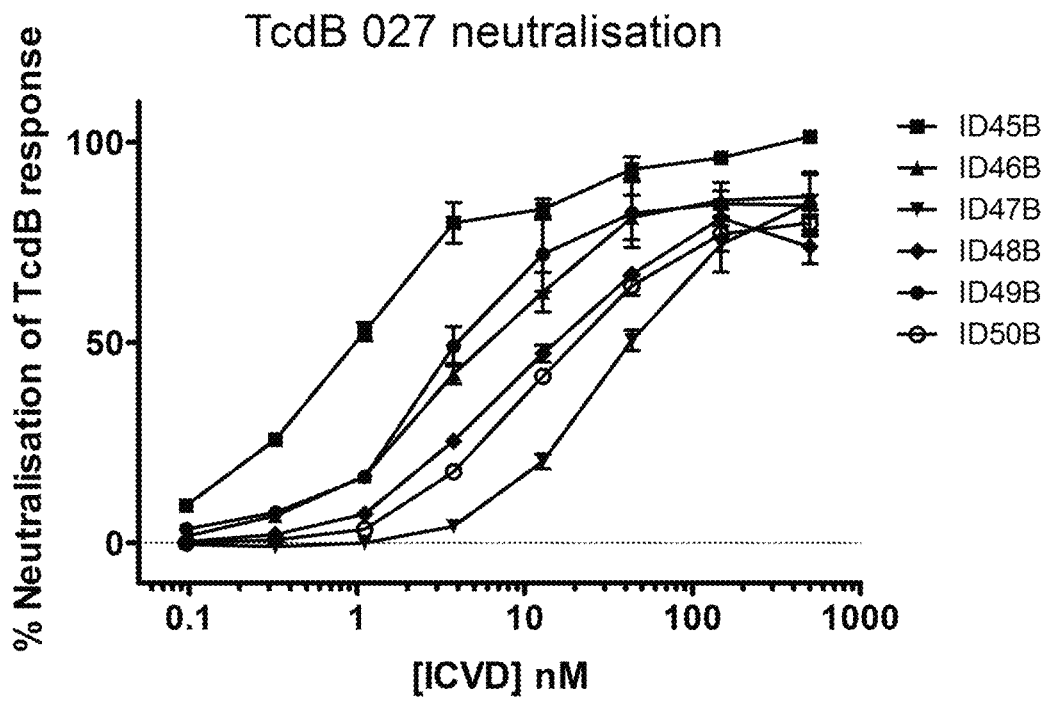

Dose-response curves of each ICVD were generated using the Vero Cell Cytotoxicity Standard Assay (FIG. 6A).

4.2 Intestinal Stability—Standard Human Faecal Supernatant Intestinal Tract Model ICVDs were digested for 30 minutes in human faecal supernatant pool 4 according to the Standard Human Faecal Supernatant Intestinal Tract Model. Percentage survival of ICVDs was calculated using the Standard Western Blot Stability Assay. The results are shown in FIG. 6B.

4.3 Conclusion

All substitutions reduced potency relative to 'unsubstituted' ID45B. However, R107H and R107F substitutions (ID46B and ID49B) resulted in only a minor potency reduction, whilst R107A, R107Q and R107W substitutions (ID47B, ID48B and ID50B) resulted in substantial potency reduction (FIG. 6A).

Figure 6B:
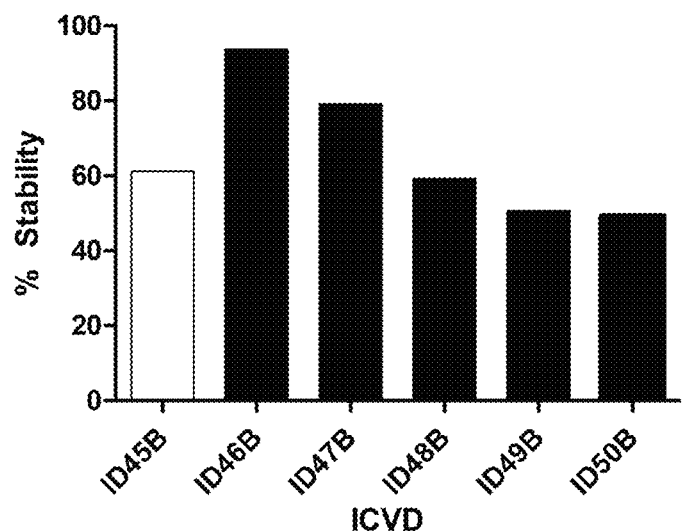

Whilst both R107H and R107F substitutions resulted in a similar minor potency reduction, R107H resulted in the highest intestinal stability increase of all substitutions tested (see FIG. 6B, ID46B—an approximate 35% increase in recovery compared to 0 mins, compared to ID45B R107). The R107F substitution, in contrast, resulted in an approximate 10% decrease compared to R107 (FIG. 6B, ID49B).

R107H provided the largest increase in stability, with only a minor impact on potency.

Example 5: Substitution of Multiple Arginine Residues with Histidine Residues in CDR2 of Anti-TcdB ICVD ID2B, and the Impact of Substitution Position within CDR3 of ID2B ID2B is a modified anti-TcdB ICVD derived from a progenitor ICVD (Q31B1). Residues R53 and R56 in CDR2 of the ID2B polypeptide sequence were both substituted with histidine residues (making "ID20B"). Independently, residues R107 and R109 in CDR3 of the ID2B polypeptide sequence were each substituted with a histidine residue (the sole R107H substitution making "ID21B" and the sole R109H substitution making "ID22B"). These ICVDs are summarised in Table 5. The impact of these substitutions on trypsin stability, intestinal stability and potency was tested.

TABLE 5

| ICVD | Substitution(s) |
| --- | --- |
| ID2B | None |
| ID20B | R53H and R56H (both in CDR2) M34I |
| ID21B | R107H (in CDR3) M34I |
| ID22B | R109H (in CDR3) M34I |

DNA encoding ID2B was cloned into vector pMEK222, expressed, and purified from the periplasm of *E. coli*. ID2B carries a C-terminal Flag-His6 tag. DNA encoding I D20B, ID21B and I D22B was cloned and expressed in yeast.

5.1 Potency—Vero Cell Cytotoxicity Standard Assay

Figure 7:
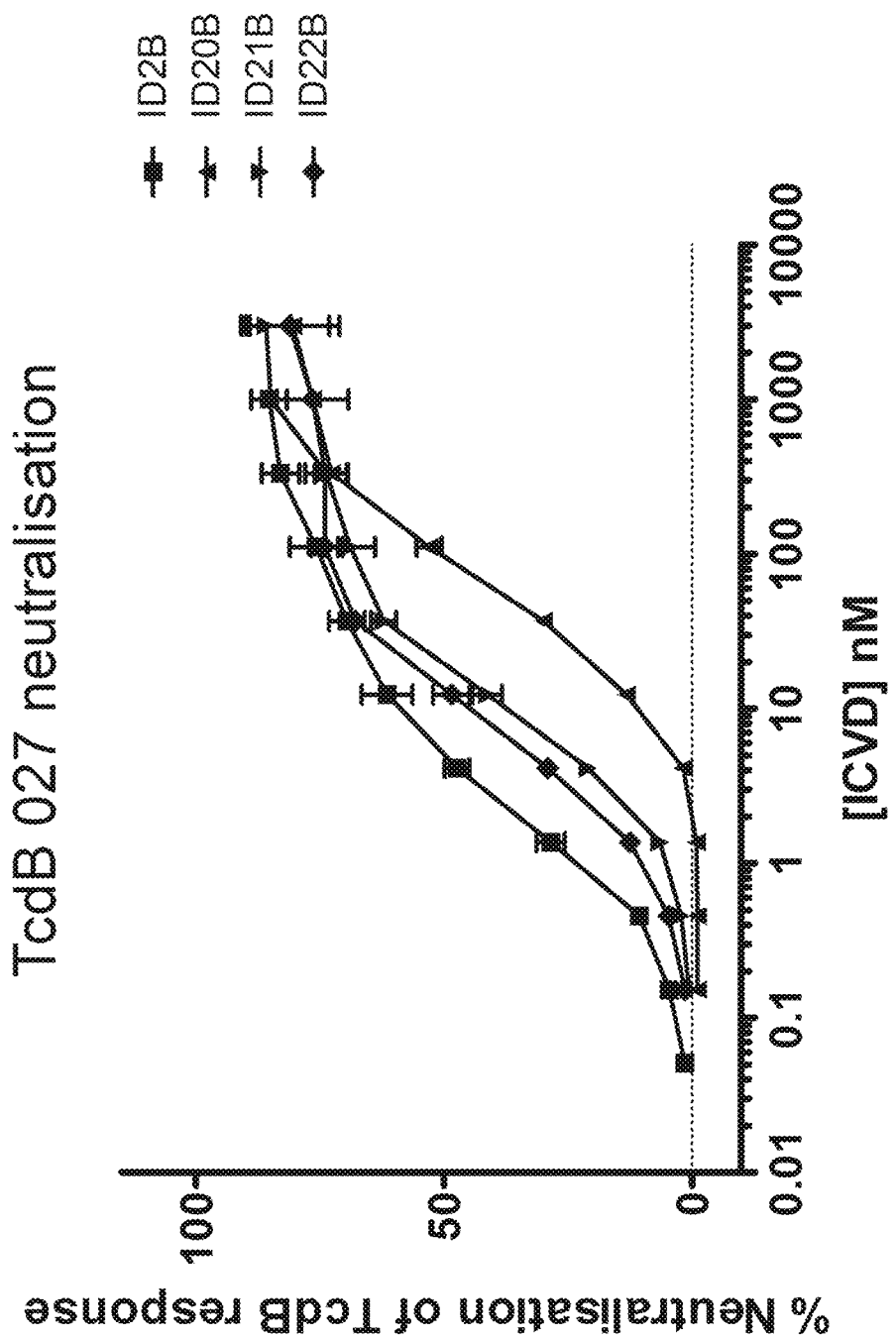

Dose-response curves of each ICVD were generated using TcdB from the 027 *C. difficile* ribotype in the Vero Cell Cytotoxicity Standard Assay (FIG. 7).

5.2.1 The Standard Trypsin Intestinal Tract Model

The ICVDs were assayed for trypsin stability. A buffered (10 mM acetic acid, pH 3.2, containing 0.01% thimerosal) aqueous suspension of TPCK-treated Trypsin-agarose beads (trypsin from bovine pancreas; T4019; Sigma Aldrich) is used for the assay. The beads are washed 3 times with water (250 µl beads+1.25 ml water) followed by washing 5 times with Trypsin buffer (TRYP buffer; 1 mM Tris-HCl, 20 mM CaCl2 [pH 8.0]). Finally, the resin is resuspended in TRYP buffer as a 50% (v/v) suspension.

100 µl of a 2 mg/ml construct solution is mixed with 225 µl 50% (v/v) immobilized TPCK-treated Trypsin in TRYP buffer. After time intervals of 0, 10, 15, 30, 45 and 60 minutes of incubation at 37° C. in a shaker, samples are taken as follows: resin is pelleted by a 1 min centrifugation step at 500×g, and a 40 µl sample is taken from the supernatant and mixed with 2× sample loading buffer (such as Laemmli buffer). The remaining suspension is mixed again, and put back at 37° C. in the shaker.

Figure 8A:
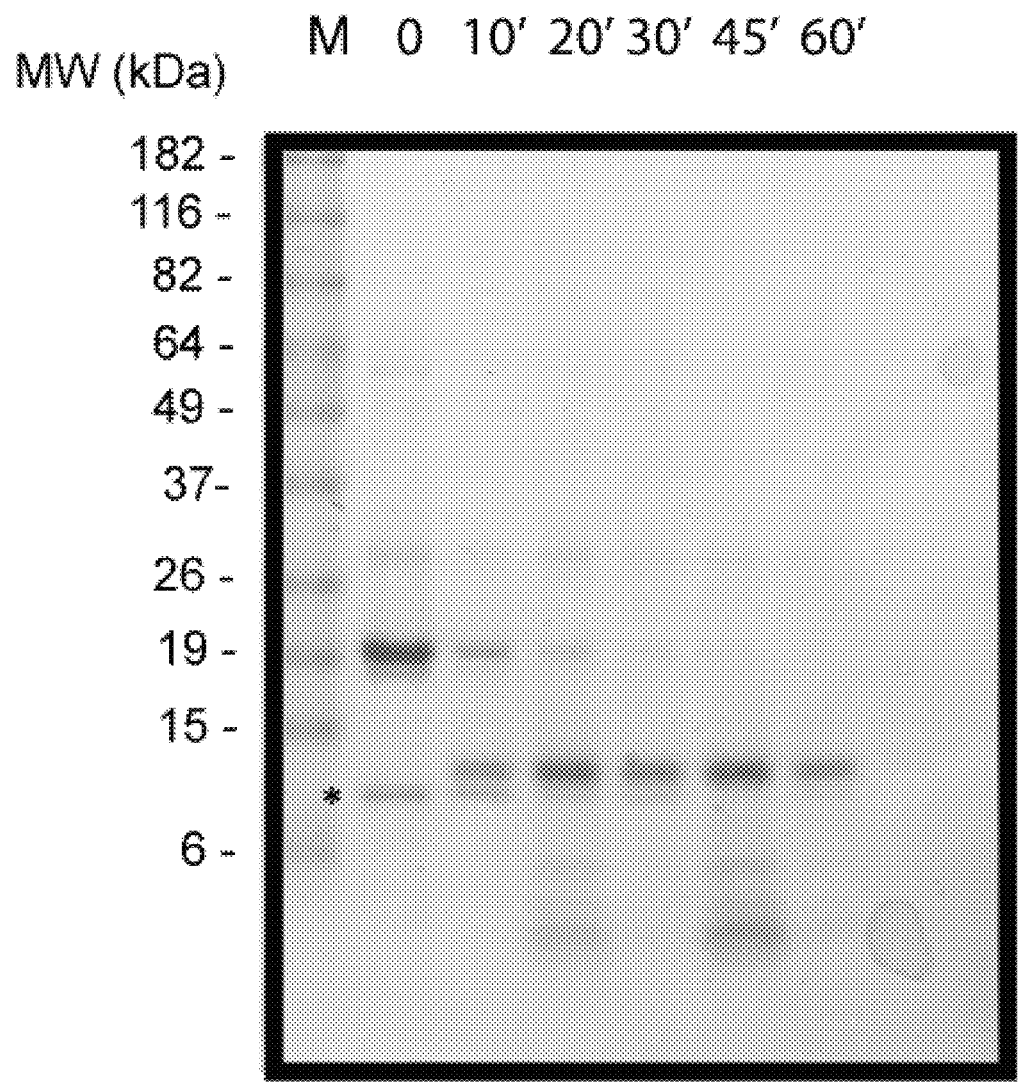
Figure 8B:
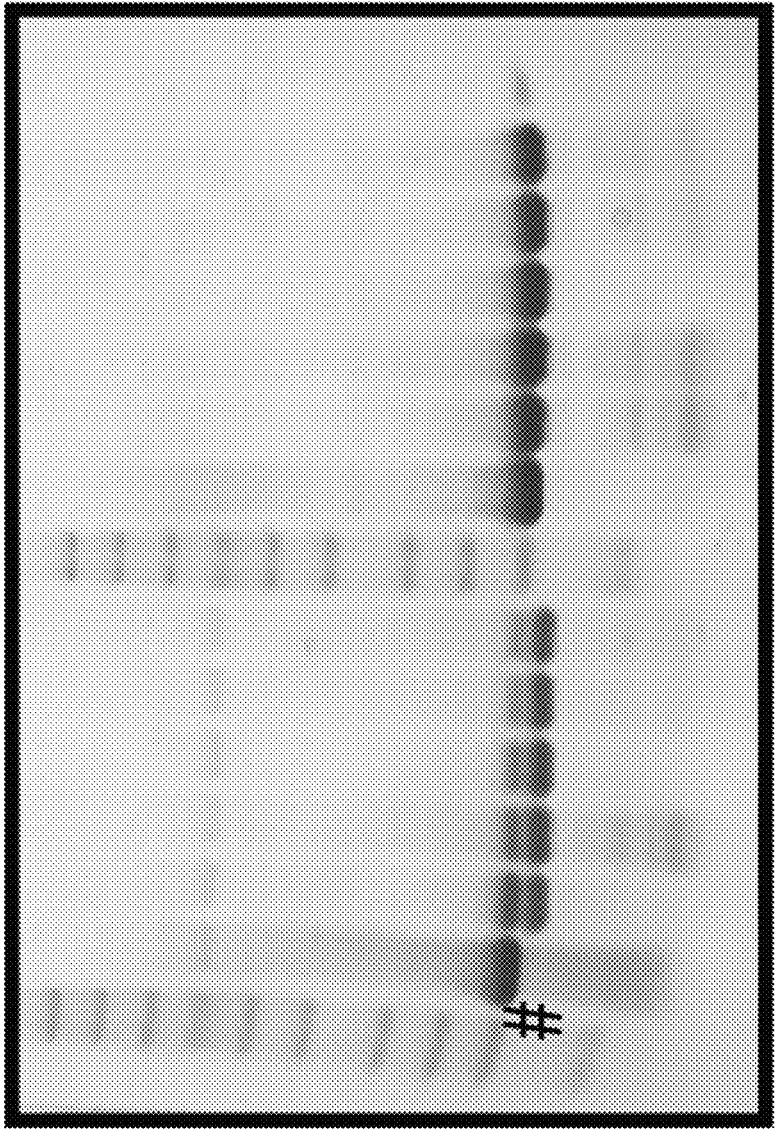
Figure 8C:
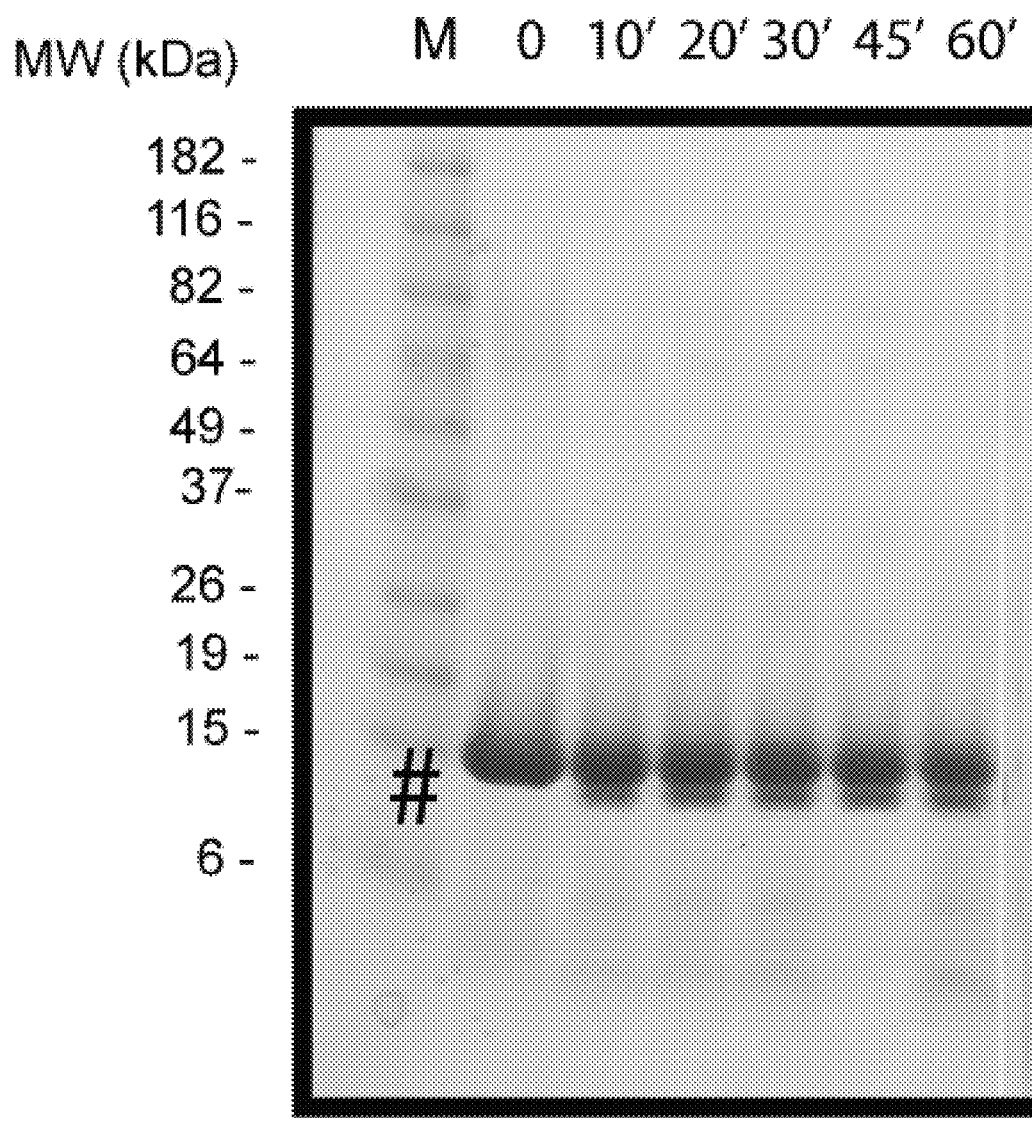

For analysis, 15 µl of each sample is mixed with 5 µl 4× loading dye, boiled for 10 mins and 15 µl is loaded per lane on a polyacrylamide gel (such as NuPAGE 10% acrylamide Bis-Tris gel). Gels are run in SDS-MES buffer at 200 V for 35 mins. Gels are fixed in 40% methanol, 7% acetic acid for 30 mins and stained in colloidal Coomassie Brilliant Blue stain overnight. Gels are destained in water before imaging (such as using ImageQuant LAS4000 with 7 secs exposure) (FIGS. 8A-C). The quantity of intact constructs relative to cleaved constituent polypeptides can be assessed by comparing the corresponding bands in each time point lane. Asterisks and # in the electrophoresis gel figures indicate bands containing cleaved fragments.

5.2.2 Intestinal Stability—Standard Human Faecal Supernatant Intestinal Tract Model ID2B and ID21B were digested for 1 hour in Faecal Pools 3 and 4 (FIG. 9) according to the Standard Human Faecal Supernatant Intestinal Tract Model. Percentage stability of ICVDs was calculated using the Standard Toxin ELISA Assay.

5.3 Conclusion

The single CDR3 substitutions resulted in a minor reduction in potency (FIG. 7, ID21B and ID22B), whilst the double CDR2 substitution resulted in a more pronounced reduction in potency (FIG. 7, ID20B).

Due to the presence of the His-tag in ID2B, the results from the electrophoresis gel in FIG. 8A are unclear. The more central R107H substitution (FIG. 8B, ID21B) provided a greater trypsin stability increase than the more peripheral R109H substitution (FIG. 8C, ID22B). This indicates that such substitutions may be more stabilising when made in a central 'window' of a CDR.

The faecal supernatant stability of ID21B (R107H) was substantially increased in both pool 3 (*C. diff* positive patient faeces) and pool 4 (*C. diff* negative patent faeces) compared to unsubstituted ID2B (FIG. 9).

Example 6: Substitution of an Arginine Residue with a Histidine Residue in CDR2 of Anti-TcdB ICVD ID1B, and the Impact of Substitution Position within CDR3 of ID1B ID1B is a modified anti-TcdB ICVD derived from a progenitor ICVD (B10F1). B10F1 was isolated, cloned and purified from a llama immunised with 100 ug of TcdB toxoids prepared by formalin inactivation of purified TcdB.

Residue R58 in CDR2 of the ID1B polypeptide sequence was substituted with a histidine residue (making "ID24B"). Independently, residues R105 and R108 in CDR3 of the ID1B polypeptide sequence were each substituted with a histidine residue (the R105H substitution making "ID27B" and the R108H substitution making "ID25B"). These ICVDs are summarised in Table 6. The impact of these substitutions on intestinal stability and potency was tested.

TABLE 6

| ICVD | Substitution(s) |
| --- | --- |
| ID1B | None |
| ID24B | R58H (in CDR2) M34I |

TABLE 6-continued

| ICVD | Substitution(s) |
|---|---|
| ID25B | R108H (in CDR3) |
| | M34I |
| ID27B | R105H (in CDR3) |
| | M34I |

DNA encoding ID1B, ID24B, ID25B and ID27B was cloned and expressed in yeast.

6.1 Potency—Vero Cell Cytotoxicity Standard Assay

Figure 10A:
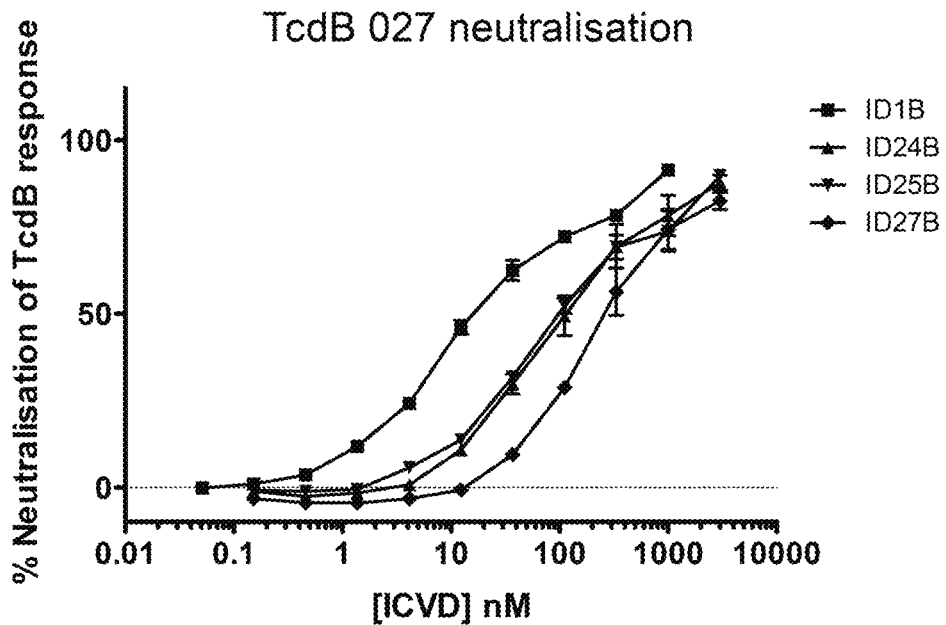

Dose-response curves of each ICVD were generated using TcdB from the 027 C. difficile ribotype in the Vero Cell Cytotoxicity Standard Assay (FIG. 10A).

6.2.1 Intestinal Stability—Standard Human Faecal Supernatant Intestinal Tract Model ID1B, ID24B, ID25B and ID27B were digested for 1 hour in Faecal Pool 2 (FIG. 10B) according to the Standard Human Faecal Supernatant Intestinal Tract Model. Percentage survival of ICVDs was calculated using the Standard Toxin ELISA Assay.

6.2.2 Intestinal stability—The Standard Trypsin Intestinal Tract Model

Figure 11A:
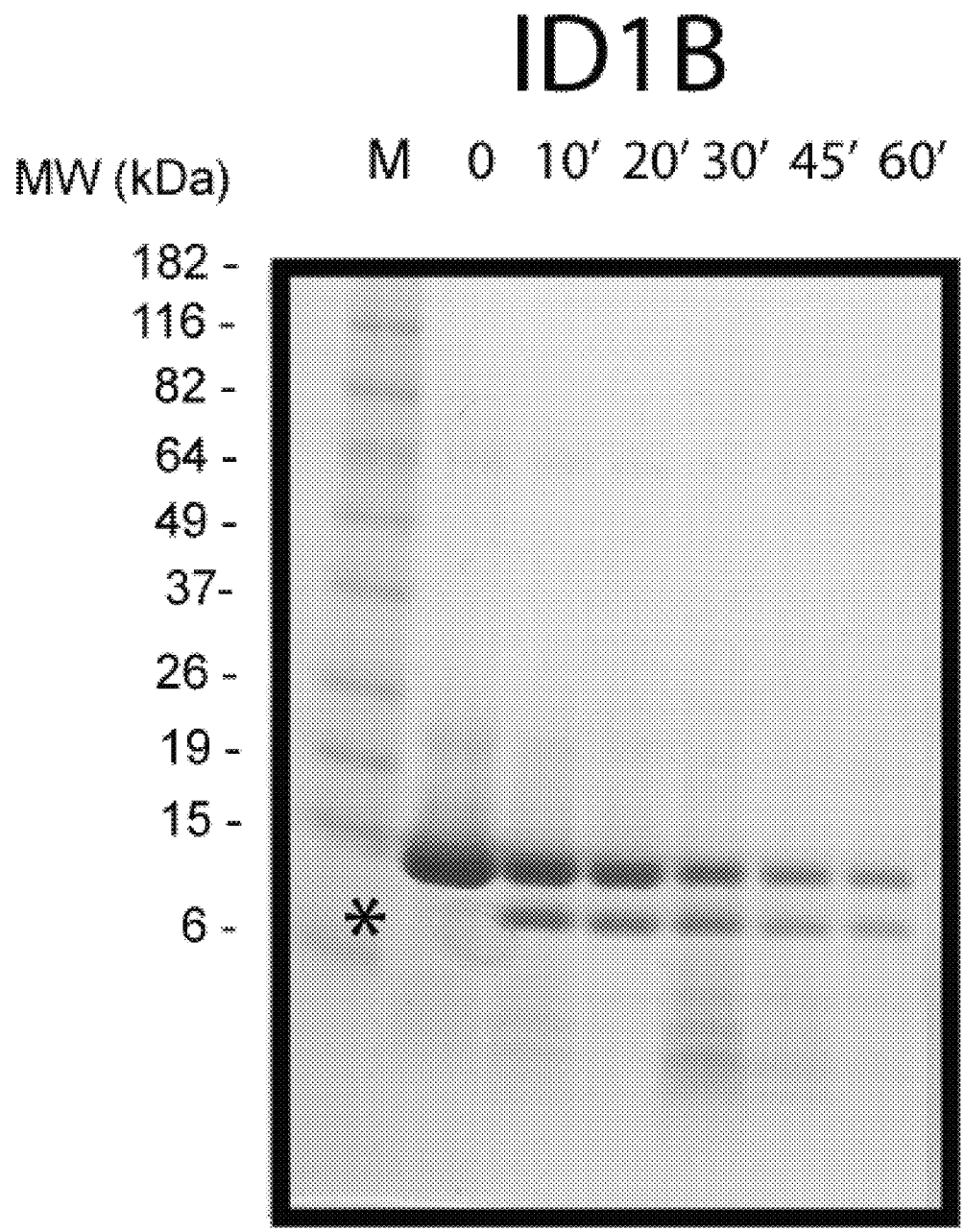
Figure 11B:
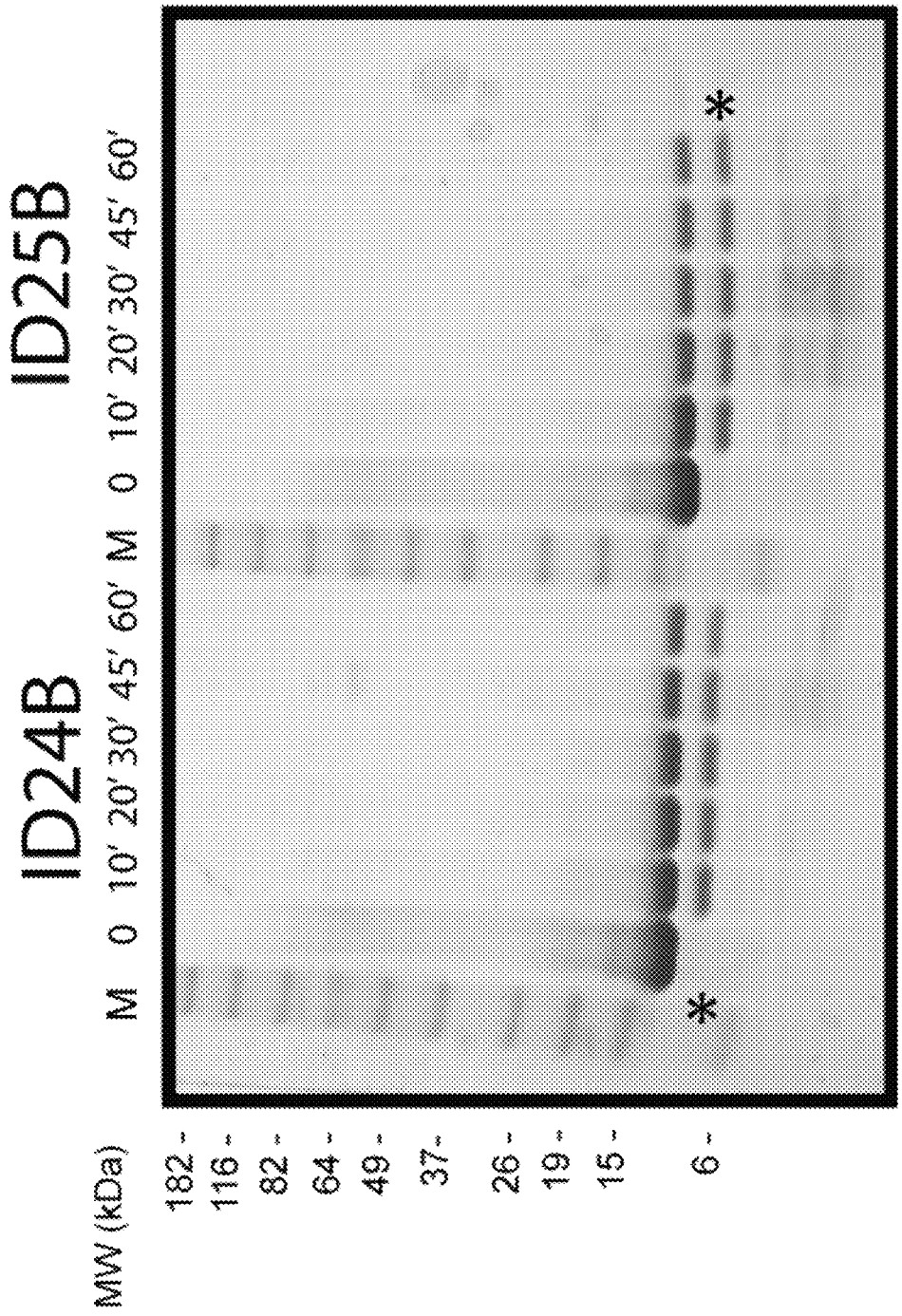
Figure 11C:
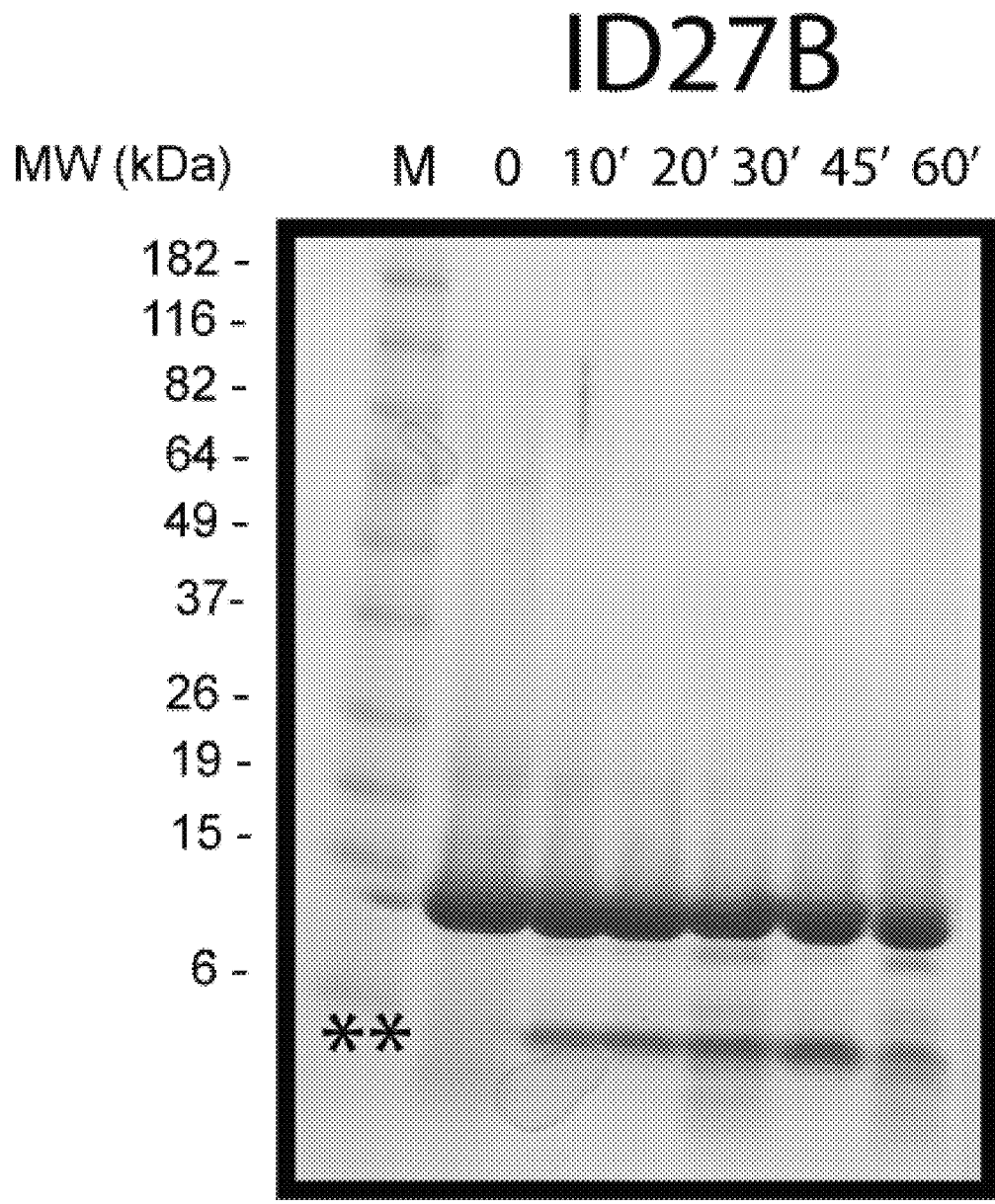

The ICVDs were assayed for trypsin stability, in the manner described in Example 5 above (FIGS. 11A-C).

6.3 Conclusion

The single CDR3 substitutions resulted in a minor reduction in potency (FIG. 10A).

The density of the main band in the ID1B gel (FIG. 11A) appears to reduce to a greater extent over the time periods tested than that of the substituted ICVDs (FIGS. 11B-11C) and therefore the substituted ICVDs appear to be more stable than unsubstituted ID1B in this trypsin assay.

Figure 10B:
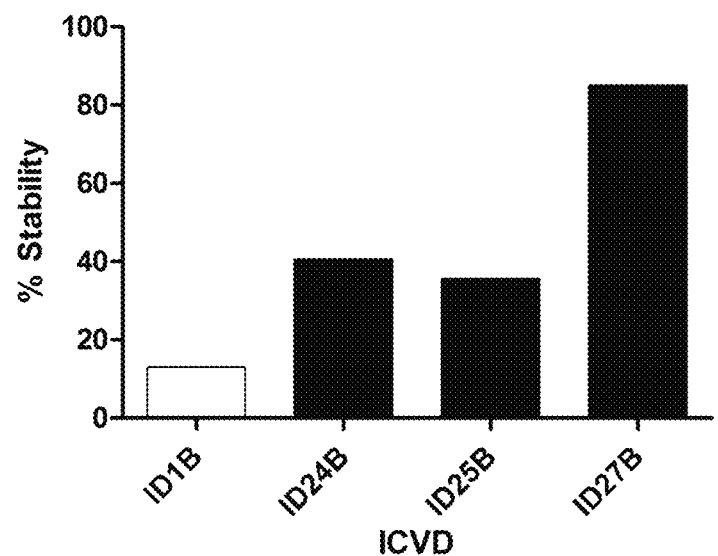

The faecal supernatant stability of all substituted ICVDs was increased (FIG. 10B). The more central R105H CDR3 substitution (FIG. 10B, ID27B) provided a greater faecal supernatant stability increase than the more peripheral R108H CDR3 substitution (FIG. 10B, ID25B). This indicates that such substitutions may be more stabilising when made in a central 'window' of a CDR.

Example 7: Substitution of an Arginine Residue with a Histidine Residue in CDR3 of One Arm of an Anti-TcdB Bivalent Construct ID41B is an anti-TcdB bivalent construct consisting of modified versions of wild type ICVDs Q31B1 and B10F1. An R108H (CDR3) substitution was made in the B10F1 arm of ID41B (making "ID43B"). The impact of this substitution on potency and intestinal stability was tested. DNA encoding ID41B and ID43B was cloned and expressed in yeast.

7.1 Potency—Vero Cell Cytotoxicity Standard Assay

Figure 12A:
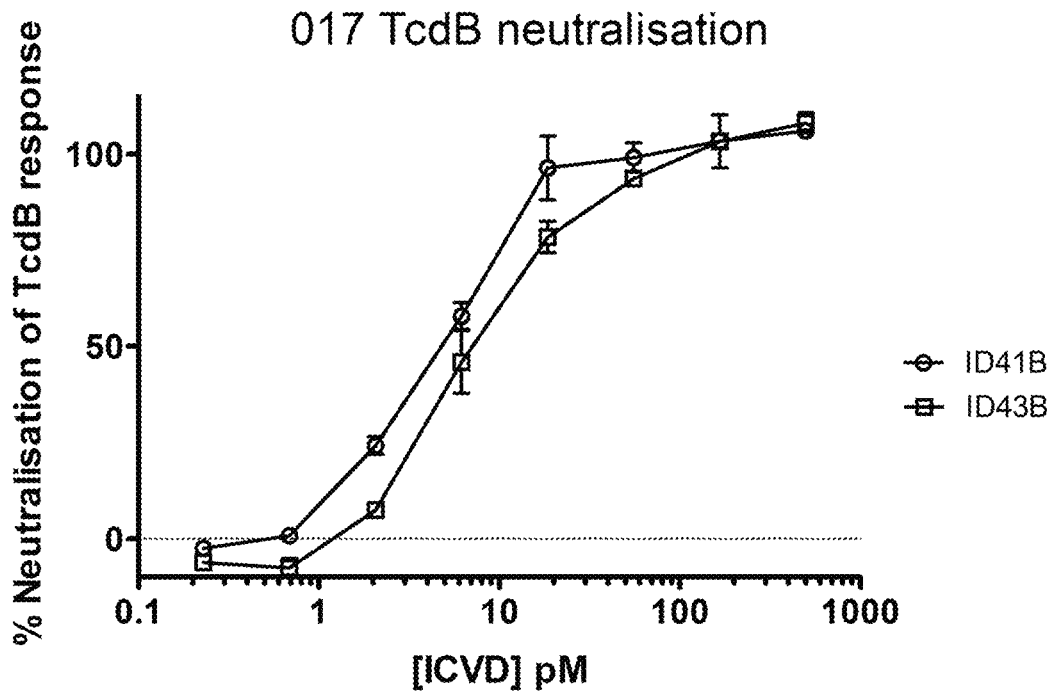
FIG. 12C—Stability of anti-TcdB bihead constructs ID41B and ID43B in *C. difficile* negative human faecal supernatant pool 3 after 4 hour incubation (three repeat ELISAs)
FIG. 12D—Stability of anti-TcdB bihead constructs ID41B and ID43B in *C. difficile* negative human faecal supernatant pool 4 after 4 hour incubation (three repeat ELISAs)

Dose-response curves of each construct were generated using TcdB from the 017 C. difficile ribotype in the Vero Cell Cytotoxicity Standard Assay (FIG. 12A).

7.2 Intestinal Stability—Standard Toxin ELISA Assay

Figure 12B:
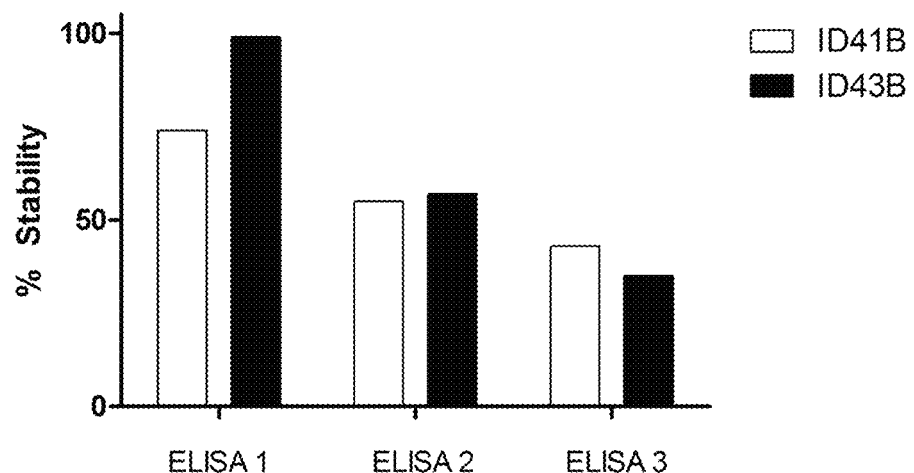

Constructs were digested for 4 hours in Faecal Pools 2, 3 and 4 according to the Standard Human Faecal Supernatant Intestinal Tract Model. Three repeat ELISAs were run for each faecal pool. Percentage survival was calculated using the Standard Toxin ELISA Assay (FIGS. 12B-12D).

7.3 Conclusion

The R108H substitution (ID43B) had a very minor impact on potency (FIG. 12A). In the majority of faecal supernatant assays (six out of nine across all faecal pools), the R108H substitution in ID43B resulted in increased stability (FIGS. 12B-12D).

Example 8: Substitution of an Arginine Residue with a Histidine Residue in CDR3 of an Anti-TcdA Bivalent ICVD ID17A is an anti-TcdA bivalent construct consisting of modified versions of wild type ICVDs B4F10 and Q34A3 (B4F10 and Q34A3 were isolated, cloned and purified from a llama immunised with TcdA toxoids prepared by formalin inactivation of purified TcdA).

An R109H (CDR3) substitution was made in the B4F10 arm of ID17A (making "ID29A"). The impact of this substitution on potency and intestinal stability was tested. DNA encoding ID17A and ID29A was cloned and expressed in yeast.

8.1 Potency—Vero Cell Cytotoxicity Standard Assay

Figure 13A:
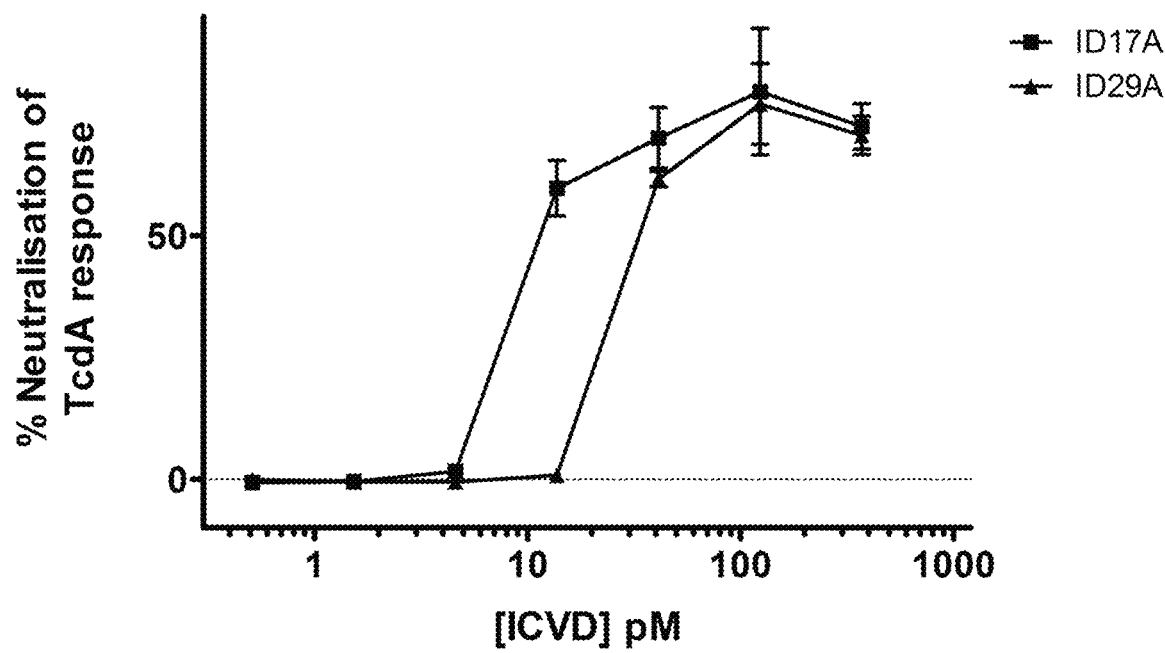
FIG. 13A—TcdA 087 neutralisation by ID17A and ID29A in the Vero cell cytotoxicity assay FIG. 13B—Stability of anti-TcdA bihead constructs ID17A and ID29A in human faecal supernatants after 1 hour incubation

Dose-response curves of each construct were generated using TcdA in the Vero Cell Cytotoxicity Standard Assay (FIG. 13A).

Figure 13B:
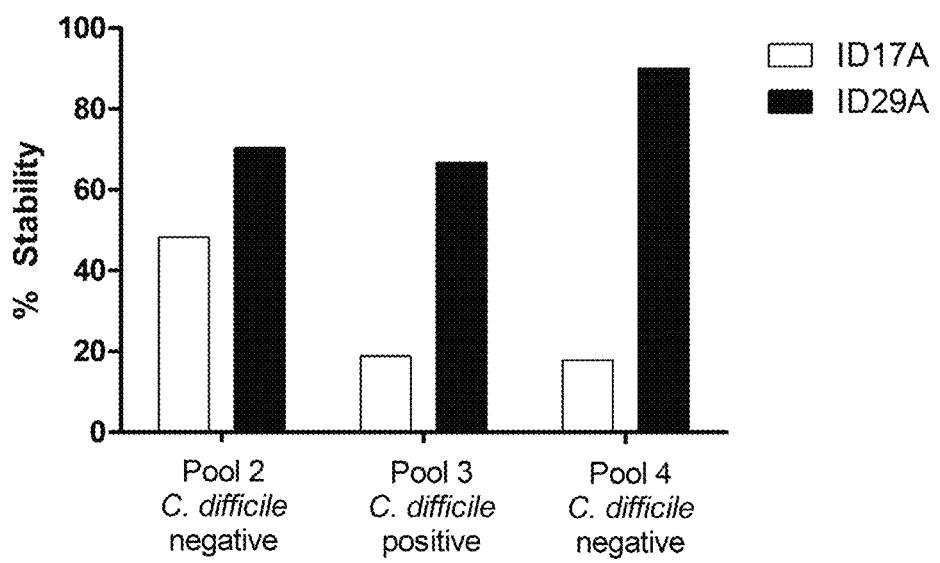

8.2 Intestinal Stability—Standard Human Faecal Supernatant Intestinal Tract Model Constructs were digested for 1 hour in Faecal Pools 2, 3 and 4 according to the Standard Human Faecal Supernatant Intestinal Tract Model. Percentage survival was calculated using the Standard Toxin ELISA Assay (FIG. 13B).

8.3 Conclusion

The R109H (CDR3) substitution in one arm of this anti-TcdA bihead had a minor impact on potency (FIG. 13A). In all faecal pools tested, this substitution resulted in highly increased stability (FIG. 13B).

Example 9: Substitution of an Arginine Residue with a Histidine Residue in CDR3 of an Anti-IL-6R ICVD 7F6

7F6 is an anti-IL-6R ICVD. 7F6 was isolated, cloned and purified from a llama immunised with soluble human recombinant IL-6R.

Residue R102 in CDR3 of the 7F6 polypeptide sequence was substituted with a histidine residue (making "ID-3V") and the impact of this substitution on potency and intestinal stability was tested. DNA encoding 7F6 and ID-3V was cloned and expressed in E. coli.

9.1 Potency—Standard gp130 ELISA Assay

Dose-response curves were generated using the standard gp130 ELISA assay and these were used to generate EC50 values (Table 7, graph not shown).

TABLE 7

| Construct | Substitution | EC50 (nM) |
|---|---|---|
| 7F6 | None (R102) | 0.15 |
| ID-3V | R102H (in CDR3) | 0.16 |

9.2 Intestinal Stability—Standard Mouse Small Intestinal Supernatant Intestinal Tract Model ICVDs were digested for 4 hours in mouse small intestinal material according to the Standard Mouse Small Intestinal Supernatant Intestinal Tract Model. Percentage stability of ICVDs was calculated using the Standard gp130 ELISA assay. The results are shown in Table 8.

TABLE 8

| Construct | Substitution | % Stability |
| --- | --- | --- |
| 7F6 | None (R102) | 1% |
| ID-3V | R102H (in CDR3) | 12% |

9.3 Intestinal stability—Standard Human Faecal Supernatant Intestinal Tract Model ICVDs were digested for 16 hours in human faecal supernatant according to the Standard Human Faecal Supernatant Intestinal Tract Model. Percentage stability of ICVDs was calculated using the Standard gp130 ELISA assay. The results are shown in Table 9.

TABLE 9

| Construct | Substitution | % Stability |
| --- | --- | --- |
| 7F6 | None (R102) | 28% |
| ID-3V | R102H (in CDR3) | 41% |

9.4 Conclusion

This R102H substitution in CDR3 of 7F6 further increased intestinal stability of the ICVD according to both the Standard Mouse Small Intestinal Supernatant Intestinal Tract Model (see Tables 8 and 9), without significantly impacting potency (Table 7).

Example 10: Substitution of an Arginine Residue with a Histidine Residue in CDR3 of an Anti-IL-6R ICVD 5G9

5G9 is an anti-IL-6R ICVD. 5G9 was isolated, cloned and purified from a llama immunised with soluble human recombinant IL-6R.

Residue R105 in CDR3 of the 5G9 polypeptide sequence was substituted with a histidine residue (making "ID-54V") and the impact of this substitution on potency and intestinal stability was tested. DNA encoding 5G9 and ID-54V was cloned and expressed in E. coli.

10.1 Potency—Standard gp130 ELISA Assay

Dose-response curves were generated using the standard gp130 ELISA assay and these were used to generate EC50 values (Table 10, graph not shown).

TABLE 10

| Construct | Substitution | EC50 (nM) |
| --- | --- | --- |
| 5G9 | None (R105) | 0.09 |
| ID-54V | R105H (in CDR3) | 0.15 |

10.2 Intestinal Stability—Standard Mouse Small Intestinal Supernatant Intestinal Tract Model ICVDs were digested for 4 hours in mouse small intestinal material according to the Standard Mouse Small Intestinal Supernatant Intestinal Tract Model. Percentage stability of ICVDs was calculated using the Standard gp130 ELISA assay. The results are shown in Table 11.

TABLE 11

| Construct | Substitution | % Stability |
| --- | --- | --- |
| 5G9 | None (R105) | 5% |
| ID-54V | R105H (in CDR3) | 36% |

10.3 Intestinal Stability—Standard Human Faecal Supernatant Intestinal Tract Model ICVDs were digested for 16 hours in human faecal supernatant according to the Standard Human Faecal Supernatant Intestinal Tract Model. Percentage stability of ICVDs was calculated using the Standard gp130 ELISA assay. The results are shown in Table 12.

TABLE 12

| Construct | Substitution | % Stability |
| --- | --- | --- |
| 5G9 | None (R105) | 40% |
| ID-54V | R105H (in CDR3) | 48% |

10.4 Conclusion

This R105H substitution in CDR3 of 5G9 further increased intestinal stability of the ICVD according to both the Standard Mouse Small Intestinal Supernatant Intestinal Tract Model (see Tables 11 and 12), with only a minor impact on potency (Table 10).

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps. All patents and patent applications mentioned throughout the specification of the present invention are herein incorporated in their entirety by reference. The invention embraces all combinations of preferred and more preferred groups and suitable and more suitable groups and embodiments of groups recited above.

The invention claimed is:

1. A method of making a HIS-substituted VHH with increased intestinal stability when administered to an individual, wherein the method comprises:
   (i) providing a progenitor VHH having an amino acid sequence comprising three complementarity determining regions (CDR1-CDR3) wherein said progenitor VHH binds a target;
   (ii) substituting an arginine residue or a lysine residue with a histidine residue in CDR2 or CDR3 of said amino acid sequence to produce a HIS-substituted VHH comprising a HIS-substituted amino acid sequence, wherein said histidine residue is substituted for said arginine residue or said lysine residue in CDR2 or CDR3, wherein said HIS-substituted VHH comprising a HIS-substituted amino acid sequence is produced in yeast; and
   (iii) selecting from said HIS-substituted VHH comprising a HIS-substituted amino acid sequence a His-substituted VHH that maintains a binding specificity of the progenitor VHH and has increased intestinal stability relative to said progenitor VHH, thereby obtaining a selected HIS-substituted VHH;

wherein the intestinal stability of the selected HIS-substituted VHH is increased by at least 5% relative to the intestinal stability of said progenitor VHH as determined by a Standard Human Fecal Supernatant Intestinal Tract Model;

wherein the EC50 of the selected HIS-substituted VHH is increased by no more than 400% relative to the EC50 of said progenitor VHH by an ELISA-based assay.

2. The method of claim 1, wherein step (ii) comprises substituting said arginine residue or said lysine residue with said histidine residue in two CDRs of said amino acid sequence.

3. The method of claim 1, wherein step (ii) comprises substituting said arginine residue or said lysine residue with said histidine residue in only one CDR of said amino acid sequence.

4. The method of claim 1, wherein step (ii) comprises substituting said arginine residue or said lysine residue with said histidine residue in only CDR2.

5. The method of claim 1, wherein (ii) comprises substituting said arginine residue or said lysine residue with said histidine residue in only CDR3.

6. The method of claim 1, wherein no more than one lysine or arginine residue is substituted.

7. The method of claim 1, wherein the selected HIS-substituted VHH has increased intestinal stability in the duodenum, jejunum, ileum cecum, colon, rectum and/or anal canal, relative to the stability of said progenitor VHH in the duodenum, jejunum, ileum cecum, colon, rectum and/or anal canal, respectively.

8. The method of claim 1, wherein the stability of the selected HIS-substituted VHH is increased by at least 5%, 30%, or 50%, relative to the stability of said progenitor VHH, after 1 hour incubation in the Standard Human Fecal Supernatant Intestinal Tract Model.

9. The method of claim 1, wherein the EC50 of the selected HIS-substituted VHH is increased by no more than 300% relative to the EC50 of said progenitor VHH.

10. The method of claim 9, wherein the EC50 of the selected HIS-substituted VHH is increased by no more than 200% relative to the EC50 of said progenitor VHH.

11. The method of claim 10, wherein the EC50 of the selected HIS-substituted VHH is increased by no more than 50% relative to the EC50 of said progenitor VHH.

12. The method of claim 11, wherein the potency of the selected HIS-substituted VHH is at least the same as the potency of said progenitor VHH.

13. The method of claim 1, wherein the target is accessible via the intestinal tract.

14. The method of claim 1, wherein the target is present within the intestinal tract.

15. The method of claim 1, wherein the selected HIS-substituted VHH is comprised within a multivalent construct.

16. The method of claim 1, wherein the progenitor VHH consists of three CDRs and four framework regions.

* * * * *

SEQUENCE LISTING

```
<160> NUMBER OF SEQ ID NOS: 35

<210> SEQ ID NO 1
<211> LENGTH: 115
<212> TYPE: PRT
<213> ORGANISM: Artificial Sequence
<220> FEATURE:
<223> OTHER INFORMATION: Polypeptide sequence of anti-TNF-alpha ICVD
      Q65B1

<400> SEQUENCE: 1
```

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Ser His
            20                  25                  30

Trp Met Tyr Trp Val Arg Gln Ala Pro Gly Lys Glu Leu Glu Trp Leu
        35                  40                  45

Ser Glu Ile Asn Thr Asn Gly Leu Ile Thr Lys Tyr Gly Asp Ser Val
50                  55                  60

Lys Gly Arg Phe Thr Val Ser Arg Asn Asn Ala Ala Asn Lys Met Tyr
65                  70                  75                  80

Leu Glu Leu Thr Arg Leu Glu Pro Glu Asp Thr Ala Leu Tyr Tyr Cys
            85                  90                  95

Ala Arg Asn Gln Lys Gly Leu Asn Lys Gly Gln Gly Thr Gln Val Thr
            100                 105                 110

Val Ser Ser
        115

<210> SEQ ID NO 2
<211> LENGTH: 115
<212> TYPE: PRT
<213> ORGANISM: Artificial Sequence
<220> FEATURE:
<223> OTHER INFORMATION: Polypeptide sequence of anti-TNF-alpha ICVD
      ID8F-EV (ID32F)

<400> SEQUENCE: 2

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Ser His
            20                  25                  30

Trp Met Tyr Trp Val Arg Gln Ala Pro Gly Lys Glu Leu Glu Trp Leu
        35                  40                  45

Ser Glu Ile Asn Thr Asn Gly Leu Ile Thr His Tyr Gly Asp Ser Val
50                  55                  60

Lys Gly Arg Phe Thr Val Ser Arg Asn Asn Ala Ala Asn Lys Met Tyr
65                  70                  75                  80

Leu Glu Leu Thr Arg Leu Glu Pro Glu Asp Thr Ala Leu Tyr Tyr Cys
            85                  90                  95

Ala Arg Asn Gln Lys Gly Leu Asn Lys Gly Gln Gly Thr Gln Val Thr
            100                 105                 110

Val Ser Ser
        115

<210> SEQ ID NO 3
<211> LENGTH: 115
<212> TYPE: PRT
<213> ORGANISM: Artificial Sequence
<220> FEATURE:
<223> OTHER INFORMATION: Polypeptide sequence of anti-TNF-alpha ICVD
      ID43F

<400> SEQUENCE: 3

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Asp Phe Ser Ser His
            20                  25                  30

Trp Met Tyr Trp Val Arg Gln Ala Pro Gly Lys Glu Leu Glu Trp Leu
        35                  40                  45

Ser Glu Ile Asn Thr Asn Gly Leu Ile Thr Ala Tyr Gly Asp Ser Val
        50                  55                  60

Lys Gly Arg Phe Thr Val Ser Arg Asn Asn Ala Ala Asn Lys Met Tyr
 65                  70                  75                  80

Leu Glu Leu Thr Arg Leu Glu Pro Glu Asp Thr Ala Leu Tyr Tyr Cys
                85                  90                  95

Ala Arg Asn Gln Lys Gly Leu Asn Lys Gly Gln Gly Thr Gln Val Thr
                100                 105                 110

Val Ser Ser
        115

<210> SEQ ID NO 4
<211> LENGTH: 115
<212> TYPE: PRT
<213> ORGANISM: Artificial Sequence
<220> FEATURE:
<223> OTHER INFORMATION: Polypeptide sequence of anti-TNF-alpha ICVD
      ID44F

<400> SEQUENCE: 4

Glu Val Gln Leu Val Glu Ser Gly Gly Gly Leu Val Gln Pro Gly Gly
 1               5                   10                  15

Ser Leu Lys Leu Ser Cys Ala Ala Ser Gly Phe Asp Phe Ser Ser His
                20                  25                  30

Trp Met Tyr Trp Val Arg Gln Ala Pro Gly Lys Glu Leu Glu Trp Leu
            35                  40                  45

Ser Glu Ile Asn Thr Asn Gly Leu Ile Thr Gln Tyr Gly Asp Ser Val
        50                  55                  60

Lys Gly Arg Phe Thr Val Ser Arg Asn Asn Ala Ala Asn Lys Met Tyr
 65                  70                  75                  80

Leu Glu Leu Thr Arg Leu Glu Pro Glu Asp Thr Ala Leu Tyr Tyr Cys
                85                  90                  95

Ala Arg Asn Gln Lys Gly Leu Asn Lys Gly Gln Gly Thr Gln Val Thr
                100                 105                 110

Val Ser Ser
        115

<210> SEQ ID NO 5
<211> LENGTH: 115
<212> TYPE: PRT
<213> ORGANISM: Artificial Sequence
<220> FEATURE:
<223> OTHER INFORMATION: Polypeptide sequence of anti-TNF-alpha ICVD
      ID34F

<400> SEQUENCE: 5

Glu Val Gln Leu Val Glu Ser Gly Gly Gly Leu Val Gln Pro Gly Gly
 1               5                   10                  15

Ser Leu Lys Leu Ser Cys Ala Ala Ser Gly Phe Asp Phe Ser Ser His
                20                  25                  30

Trp Met Tyr Trp Val Arg Gln Ala Pro Gly Lys Glu Leu Glu Trp Leu
            35                  40                  45

Ser Glu Ile Asn Thr Asn Gly Leu Ile Thr His Tyr Gly Asp Ser Val
        50                  55                  60

Lys Gly Arg Phe Thr Val Ser Arg Asn Asn Ala Ala Asn Lys Met Tyr
 65                  70                  75                  80

Leu Glu Leu Thr Arg Leu Glu Pro Glu Asp Thr Ala Leu Tyr Tyr Cys
                85                  90                  95

```
Ala Arg Asn Gln His Gly Leu Asn Lys Gly Gln Gly Thr Gln Val Thr
                100                 105                 110

Val Ser Ser
        115
```

<210> SEQ ID NO 6
<211> LENGTH: 122
<212> TYPE: PRT
<213> ORGANISM: Artificial Sequence
<220> FEATURE:
<223> OTHER INFORMATION: Polypeptide sequence of anti-TcdB ICVD B10F1

<400> SEQUENCE: 6

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Tyr Met Gly Trp Phe Arg Gln Ala Pro Gly Lys Glu Arg Glu Phe Val
        35                  40                  45

Ala Ala Ile Asn Gly Ser Gly Gly Asn Arg Ile Ser Ala Asp Ser Val
    50                  55                  60

Lys Gly Arg Phe Thr Ile Ser Arg Asp Asn Ala Lys Asn Thr Val Tyr
65                  70                  75                  80

Leu Gln Leu Asn Ser Leu Lys Pro Glu Asp Thr Ala Val Tyr Tyr Cys
                85                  90                  95

Ala Ala Ser Leu Thr Tyr Tyr Gly Arg Ser Ala Arg Tyr Asp Tyr Trp
                100                 105                 110

Gly Gln Gly Thr Gln Val Thr Val Ser Ser
            115                 120
```

<210> SEQ ID NO 7
<211> LENGTH: 124
<212> TYPE: PRT
<213> ORGANISM: Artificial Sequence
<220> FEATURE:
<223> OTHER INFORMATION: Polypeptide sequence of anti-TcdB ICVD Q31B1

<400> SEQUENCE: 7

```
Glu Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Leu Ser Ser Tyr
            20                  25                  30

Thr Met Gly Trp Phe Arg Gln Ala Pro Glu Lys Glu Arg Glu Phe Val
        35                  40                  45

Ala Gly Ser Ser Arg Asp Gly Arg Thr Asn Tyr Tyr Ala Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala His Thr Thr Ser Gly Val Pro Val Arg Glu Arg Ser Tyr Ala
                100                 105                 110

Tyr Trp Gly Gln Gly Thr Gln Val Thr Val Ser Ser
            115                 120
```

<210> SEQ ID NO 8
<211> LENGTH: 122
<212> TYPE: PRT
<213> ORGANISM: Artificial Sequence -continued

```
<220> FEATURE:
<223> OTHER INFORMATION: Polypeptide sequence of anti-TcdB ICVD ID1B

<400> SEQUENCE: 8

Asp Val Gln Leu Gln Glu Ser Gly Gly Gly Leu Val Gln Ala Gly Gly
1               5                   10                  15

Ser Leu Arg Leu Ser Cys Ala Ala Ser Gly Ala Thr Phe Ser Ser Tyr
            20                  25                  30

Tyr Met Gly Trp Phe Arg Gln Ala Pro Gly Lys Glu Arg Glu Phe Val
        35                  40                  45

Ala Ala Ile Asn Gly Ser Gly Gly Asn Arg Ile Ser Ala Asp Ser Val
    50                  55                  60

Lys Gly Arg Phe Thr Ile Ser Arg Asp Asn Ala Lys Asn Thr Val Tyr
65                  70                  75                  80

Leu Gln Leu Asn Ser Leu Lys Pro Glu Asp Thr Ala Val Tyr Tyr Cys
                85                  90                  95

Ala Ala Ser Leu Thr Tyr Tyr Gly Arg Ser Ala Arg Tyr Asp Tyr Trp
            100                 105                 110

Gly Gln Gly Thr Gln Val Thr Val Ser Ser
        115                 120

<210> SEQ ID NO 9
<211> LENGTH: 124
<212> TYPE: PRT
<213> ORGANISM: Artificial Sequence
<220> FEATURE:
<223> OTHER INFORMATION: Polypeptide sequence of anti-TcdB ICVD ID2B

<400> SEQUENCE: 9

Asp Val Gln Leu Gln Glu Ser Gly Gly Gly Leu Val Gln Ala Gly Asp
1               5                   10                  15

Ser Leu Arg Leu Ser Cys Ala Ala Ser Gly Ala Thr Leu Ser Ser Tyr
            20                  25                  30

Thr Met Gly Trp Phe Arg Gln Ala Pro Glu Lys Glu Arg Glu Phe Val
        35                  40                  45

Ala Gly Ser Ser Arg Asp Gly Arg Thr Asn Tyr Tyr Ala Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala His Thr Thr Ser Gly Val Pro Val Arg Glu Arg Ser Tyr Ala
            100                 105                 110

Tyr Trp Gly Gln Gly Thr Gln Val Thr Val Ser Ser
        115                 120

<210> SEQ ID NO 10
<211> LENGTH: 124
<212> TYPE: PRT
<213> ORGANISM: Artificial Sequence
<220> FEATURE:
<223> OTHER INFORMATION: Polypeptide sequence of anti-TcdB ICVD ID20B

<400> SEQUENCE: 10

Asp Val Gln Leu Gln Glu Ser Gly Gly Gly Leu Val Gln Ala Gly Asp
1               5                   10                  15

Ser Leu Arg Leu Ser Cys Ala Ala Ser Gly Ala Thr Leu Ser Ser Tyr
            20                  25                  30
```

```
Thr Ile Gly Trp Phe Arg Gln Ala Pro Glu Lys Glu Arg Glu Phe Val
            35                  40                  45

Ala Gly Ser Ser His Asp Gly His Thr Asn Tyr Tyr Ala Asn Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                85                  90                  95

Ala Ala His Thr Thr Ser Gly Val Pro Val Arg Glu Arg Ser Tyr Ala
            100                 105                 110

Tyr Trp Gly Gln Gly Thr Gln Val Thr Val Ser Ser
            115                 120
```

<210> SEQ ID NO 11
<211> LENGTH: 124
<212> TYPE: PRT
<213> ORGANISM: Artificial Sequence
<220> FEATURE:
<223> OTHER INFORMATION: Polypeptide sequence of anti-TcdB ICVD ID21B

<400> SEQUENCE: 11

```
Asp Val Gln Leu Gln Glu Ser Gly Gly Gly Leu Val Gln Ala Gly Asp
 1               5                  10                  15

Ser Leu Arg Leu Ser Cys Ala Ala Ser Gly Ala Thr Leu Ser Ser Tyr
            20                  25                  30

Thr Ile Gly Trp Phe Arg Gln Ala Pro Glu Lys Glu Arg Glu Phe Val
            35                  40                  45

Ala Gly Ser Ser Arg Asp Gly Arg Thr Asn Tyr Tyr Ala Asn Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                85                  90                  95

Ala Ala His Thr Thr Ser Gly Val Pro Val His Glu Arg Ser Tyr Ala
            100                 105                 110

Tyr Trp Gly Gln Gly Thr Gln Val Thr Val Ser Ser
            115                 120
```

<210> SEQ ID NO 12
<211> LENGTH: 124
<212> TYPE: PRT
<213> ORGANISM: Artificial Sequence
<220> FEATURE:
<223> OTHER INFORMATION: Polypeptide sequence of anti-TcdB ICVD ID22B

<400> SEQUENCE: 12

```
Asp Val Gln Leu Gln Glu Ser Gly Gly Gly Leu Val Gln Ala Gly Asp
 1               5                  10                  15

Ser Leu Arg Leu Ser Cys Ala Ala Ser Gly Ala Thr Leu Ser Ser Tyr
            20                  25                  30

Thr Ile Gly Trp Phe Arg Gln Ala Pro Glu Lys Glu Arg Glu Phe Val
            35                  40                  45

Ala Gly Ser Ser Arg Asp Gly Arg Thr Asn Tyr Tyr Ala Asn Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                85                  90                  95
```

Ala Ala His Thr Thr Ser Gly Val Pro Val Arg Glu His Ser Tyr Ala
            100                 105                 110

Tyr Trp Gly Gln Gly Thr Gln Val Thr Val Ser Ser
        115                 120

<210> SEQ ID NO 13
<211> LENGTH: 122
<212> TYPE: PRT
<213> ORGANISM: Artificial Sequence
<220> FEATURE:
<223> OTHER INFORMATION: Polypeptide sequence of anti-TcdB ICVD ID24B

<400> SEQUENCE: 13

Asp Val Gln Leu Gln Glu Ser Gly Gly Gly Leu Val Gln Ala Gly Gly
1               5                   10                  15

Ser Leu Arg Leu Ser Cys Ala Ala Ser Gly Ala Thr Phe Ser Ser Tyr
            20                  25                  30

Tyr Ile Gly Trp Phe Arg Gln Ala Pro Gly Lys Glu Arg Glu Phe Val
        35                  40                  45

Ala Ala Ile Asn Gly Ser Gly Gly Asn His Ile Ser Ala Asp Ser Val
    50                  55                  60

Lys Gly Arg Phe Thr Ile Ser Arg Asp Asn Ala Lys Asn Thr Val Tyr
65                  70                  75                  80

Leu Gln Leu Asn Ser Leu Lys Pro Glu Asp Thr Ala Val Tyr Tyr Cys
                85                  90                  95

Ala Ala Ser Leu Thr Tyr Tyr Gly Arg Ser Ala Arg Tyr Asp Tyr Trp
            100                 105                 110

Gly Gln Gly Thr Gln Val Thr Val Ser Ser
        115                 120

<210> SEQ ID NO 14
<211> LENGTH: 122
<212> TYPE: PRT
<213> ORGANISM: Artificial Sequence
<220> FEATURE:
<223> OTHER INFORMATION: Polypeptide sequence of anti-TcdB ICVD ID25B

<400> SEQUENCE: 14

Asp Val Gln Leu Gln Glu Ser Gly Gly Gly Leu Val Gln Ala Gly Gly
1               5                   10                  15

Ser Leu Arg Leu Ser Cys Ala Ala Ser Gly Ala Thr Phe Ser Ser Tyr
            20                  25                  30

Tyr Ile Gly Trp Phe Arg Gln Ala Pro Gly Lys Glu Arg Glu Phe Val
        35                  40                  45

Ala Ala Ile Asn Gly Ser Gly Gly Asn Arg Ile Ser Ala Asp Ser Val
    50                  55                  60

Lys Gly Arg Phe Thr Ile Ser Arg Asp Asn Ala Lys Asn Thr Val Tyr
65                  70                  75                  80

Leu Gln Leu Asn Ser Leu Lys Pro Glu Asp Thr Ala Val Tyr Tyr Cys
                85                  90                  95

Ala Ala Ser Leu Thr Tyr Tyr Gly Arg Ser Ala His Tyr Asp Tyr Trp
            100                 105                 110

Gly Gln Gly Thr Gln Val Thr Val Ser Ser
        115                 120

<210> SEQ ID NO 15
<211> LENGTH: 122
<212> TYPE: PRT

<213> ORGANISM: Artificial Sequence
<220> FEATURE:
<223> OTHER INFORMATION: Polypeptide sequence of anti-TcdB ICVD ID27B

<400> SEQUENCE: 15

```
Asp Val Gln Leu Gln Glu Ser Gly Gly Gly Leu Val Gln Ala Gly Gly
1               5                   10                  15

Ser Leu Arg Leu Ser Cys Ala Ala Ser Gly Ala Thr Phe Ser Ser Tyr
            20                  25                  30

Tyr Ile Gly Trp Phe Arg Gln Ala Pro Gly Lys Glu Arg Glu Phe Val
        35                  40                  45

Ala Ala Ile Asn Gly Ser Gly Gly Asn Arg Ile Ser Ala Asp Ser Val
    50                  55                  60

Lys Gly Arg Phe Thr Ile Ser Arg Asp Asn Ala Lys Asn Thr Val Tyr
65                  70                  75                  80

Leu Gln Leu Asn Ser Leu Lys Pro Glu Asp Thr Ala Val Tyr Tyr Cys
                85                  90                  95

Ala Ala Ser Leu Thr Tyr Tyr Gly His Ser Ala Arg Tyr Asp Tyr Trp
            100                 105                 110

Gly Gln Gly Thr Gln Val Thr Val Ser Ser
        115                 120
```

<210> SEQ ID NO 16
<211> LENGTH: 266
<212> TYPE: PRT
<213> ORGANISM: Artificial Sequence
<220> FEATURE:
<223> OTHER INFORMATION: Polypeptide sequence of anti-TcdB construct
      ID41B

<400> SEQUENCE: 16

```
Asp Val Gln Leu Gln Glu Ser Gly Gly Gly Leu Val Gln Ala Gly Asp
1               5                   10                  15

Ser Leu Arg Leu Ser Cys Ala Ala Ser Gly Ala Thr Leu Ser Ser Tyr
            20                  25                  30

Thr Met Gly Trp Phe Arg Gln Ala Pro Glu Lys Glu Arg Glu Phe Val
        35                  40                  45

Ala Gly Ser Ser Arg Asp Gly Arg Thr Asn Tyr Tyr Ala Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala His Thr Thr Ser Gly Val Pro Val His Glu Arg Ser Tyr Ala
            100                 105                 110

Tyr Trp Gly Gln Gly Thr Gln Val Thr Val Ser Ser Gly Gly Gly Gly
        115                 120                 125

Ser Gly Gly Gly Gly Ser Gly Gly Gly Gly Ser Gly Gly Gly Gly Ser
    130                 135                 140

Asp Val Gln Leu Gln Glu Ser Gly Gly Gly Leu Val Gln Ala Gly Gly
145                 150                 155                 160

Ser Leu Arg Leu Ser Cys Ala Ala Ser Gly Ala Thr Phe Ser Ser Tyr
            165                 170                 175

Tyr Met Gly Trp Phe Arg Gln Ala Pro Gly Lys Glu Arg Glu Phe Val
        180                 185                 190

Ala Ala Ile Asn Gly Ser Gly Gly Asn Arg Ile Ser Ala Asp Ser Val
    195                 200                 205
```

```
Lys Gly Arg Phe Thr Ile Ser Arg Asp Asn Ala Lys Asn Thr Val Tyr
        210                 215                 220

Leu Gln Leu Asn Ser Leu Lys Pro Glu Asp Thr Ala Val Tyr Tyr Cys
225                 230                 235                 240

Ala Ala Ser Leu Thr Tyr Tyr Gly His Ser Ala Arg Tyr Asp Tyr Trp
                245                 250                 255

Gly Gln Gly Thr Gln Val Thr Val Ser Ser
                260                 265

<210> SEQ ID NO 17
<211> LENGTH: 266
<212> TYPE: PRT
<213> ORGANISM: Artificial Sequence
<220> FEATURE:
<223> OTHER INFORMATION: Polypeptide sequence of anti-TcdB construct
      ID43B

<400> SEQUENCE: 17

Asp Val Gln Leu Gln Glu Ser Gly Gly Gly Leu Val Gln Ala Gly Asp
1               5                   10                  15

Ser Leu Arg Leu Ser Cys Ala Ala Ser Gly Ala Thr Leu Ser Ser Tyr
            20                  25                  30

Thr Met Gly Trp Phe Arg Gln Ala Pro Glu Lys Glu Arg Glu Phe Val
        35                  40                  45

Ala Gly Ser Ser Arg Asp Gly Arg Thr Asn Tyr Tyr Ala Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala His Thr Thr Ser Gly Val Pro Val His Glu Arg Ser Tyr Ala
            100                 105                 110

Tyr Trp Gly Gln Gly Thr Gln Val Thr Val Ser Ser Gly Gly Gly Gly
        115                 120                 125

Ser Gly Gly Gly Gly Ser Gly Gly Gly Ser Gly Gly Gly Gly Ser
    130                 135                 140

Asp Val Gln Leu Gln Glu Ser Gly Gly Gly Leu Val Gln Ala Gly Gly
145                 150                 155                 160

Ser Leu Arg Leu Ser Cys Ala Ala Ser Gly Ala Thr Phe Ser Ser Tyr
            165                 170                 175

Tyr Met Gly Trp Phe Arg Gln Ala Pro Gly Lys Glu Arg Glu Phe Val
        180                 185                 190

Ala Ala Ile Asn Gly Ser Gly Gly Asn Arg Ile Ser Ala Asp Ser Val
    195                 200                 205

Lys Gly Arg Phe Thr Ile Ser Arg Asp Asn Ala Lys Asn Thr Val Tyr
        210                 215                 220

Leu Gln Leu Asn Ser Leu Lys Pro Glu Asp Thr Ala Val Tyr Tyr Cys
225                 230                 235                 240

Ala Ala Ser Leu Thr Tyr Tyr Gly His Ser Ala His Tyr Asp Tyr Trp
                245                 250                 255

Gly Gln Gly Thr Gln Val Thr Val Ser Ser
                260                 265

<210> SEQ ID NO 18
<211> LENGTH: 124
<212> TYPE: PRT
```

-continued

```
<213> ORGANISM: Artificial Sequence
<220> FEATURE:
<223> OTHER INFORMATION: Polypeptide sequence of anti-TcdB ICVD ID45B

<400> SEQUENCE: 18

Glu Val Gln Leu Val Glu Ser Gly Gly Gly Leu Val Gln Ala Gly Asp
1               5                   10                  15

Ser Leu Arg Leu Ser Cys Ala Ala Ser Gly Ala Thr Leu Ser Ser Tyr
            20                  25                  30

Thr Met Gly Trp Phe Arg Gln Ala Pro Glu Lys Glu Arg Glu Phe Val
        35                  40                  45

Ala Gly Ser Ser Arg Asp Gly Arg Thr Asn Tyr Tyr Ala Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala His Thr Thr Ser Gly Val Pro Val Arg Glu Arg Ser Tyr Ala
            100                 105                 110

Tyr Trp Gly Gln Gly Thr Gln Val Thr Val Ser Ser
        115                 120

<210> SEQ ID NO 19
<211> LENGTH: 124
<212> TYPE: PRT
<213> ORGANISM: Artificial Sequence
<220> FEATURE:
<223> OTHER INFORMATION: Polypeptide sequence of anti-TcdB ICVD ID46B

<400> SEQUENCE: 19

Glu Val Gln Leu Val Glu Ser Gly Gly Gly Leu Val Gln Ala Gly Asp
1               5                   10                  15

Ser Leu Arg Leu Ser Cys Ala Ala Ser Gly Ala Thr Leu Ser Ser Tyr
            20                  25                  30

Thr Met Gly Trp Phe Arg Gln Ala Pro Glu Lys Glu Arg Glu Phe Val
        35                  40                  45

Ala Gly Ser Ser Arg Asp Gly Arg Thr Asn Tyr Tyr Ala Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala His Thr Thr Ser Gly Val Pro Val His Glu Arg Ser Tyr Ala
            100                 105                 110

Tyr Trp Gly Gln Gly Thr Gln Val Thr Val Ser Ser
        115                 120

<210> SEQ ID NO 20
<211> LENGTH: 124
<212> TYPE: PRT
<213> ORGANISM: Artificial Sequence
<220> FEATURE:
<223> OTHER INFORMATION: Polypeptide sequence of anti-TcdB ICVD ID47B

<400> SEQUENCE: 20

Glu Val Gln Leu Val Glu Ser Gly Gly Gly Leu Val Gln Ala Gly Asp
1               5                   10                  15

Ser Leu Arg Leu Ser Cys Ala Ala Ser Gly Ala Thr Leu Ser Ser Tyr
            20                  25                  30
```

```
Thr Met Gly Trp Phe Arg Gln Ala Pro Glu Lys Glu Arg Glu Phe Val
        35                  40                  45

Ala Gly Ser Ser Arg Asp Gly Arg Thr Asn Tyr Tyr Ala Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala His Thr Thr Ser Gly Val Pro Val Ala Glu Arg Ser Tyr Ala
                100                 105                 110

Tyr Trp Gly Gln Gly Thr Gln Val Thr Val Ser Ser
            115                 120

<210> SEQ ID NO 21
<211> LENGTH: 124
<212> TYPE: PRT
<213> ORGANISM: Artificial Sequence
<220> FEATURE:
<223> OTHER INFORMATION: Polypeptide sequence of anti-TcdB ICVD ID48B

<400> SEQUENCE: 21

Glu Val Gln Leu Val Glu Ser Gly Gly Gly Leu Val Gln Ala Gly Asp
1               5                   10                  15

Ser Leu Arg Leu Ser Cys Ala Ala Ser Gly Ala Thr Leu Ser Ser Tyr
            20                  25                  30

Thr Met Gly Trp Phe Arg Gln Ala Pro Glu Lys Glu Arg Glu Phe Val
        35                  40                  45

Ala Gly Ser Ser Arg Asp Gly Arg Thr Asn Tyr Tyr Ala Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala His Thr Thr Ser Gly Val Pro Val Gln Glu Arg Ser Tyr Ala
                100                 105                 110

Tyr Trp Gly Gln Gly Thr Gln Val Thr Val Ser Ser
            115                 120

<210> SEQ ID NO 22
<211> LENGTH: 124
<212> TYPE: PRT
<213> ORGANISM: Artificial Sequence
<220> FEATURE:
<223> OTHER INFORMATION: Polypeptide sequence of anti-TcdB ICVD ID49B

<400> SEQUENCE: 22

Glu Val Gln Leu Val Glu Ser Gly Gly Gly Leu Val Gln Ala Gly Asp
1               5                   10                  15

Ser Leu Arg Leu Ser Cys Ala Ala Ser Gly Ala Thr Leu Ser Ser Tyr
            20                  25                  30

Thr Met Gly Trp Phe Arg Gln Ala Pro Glu Lys Glu Arg Glu Phe Val
        35                  40                  45

Ala Gly Ser Ser Arg Asp Gly Arg Thr Asn Tyr Tyr Ala Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
```

```
                         85                  90                  95

Ala Ala His Thr Thr Ser Gly Val Pro Val Phe Glu Arg Ser Tyr Ala
                    100                 105                 110

Tyr Trp Gly Gln Gly Thr Gln Val Thr Val Ser Ser
            115                 120

<210> SEQ ID NO 23
<211> LENGTH: 124
<212> TYPE: PRT
<213> ORGANISM: Artificial Sequence
<220> FEATURE:
<223> OTHER INFORMATION: Polypeptide sequence of anti-TcdB ICVD ID50B

<400> SEQUENCE: 23

Glu Val Gln Leu Val Glu Ser Gly Gly Gly Leu Val Gln Ala Gly Asp
1               5                   10                  15

Ser Leu Arg Leu Ser Cys Ala Ala Ser Gly Ala Thr Leu Ser Ser Tyr
                20                  25                  30

Thr Met Gly Trp Phe Arg Gln Ala Pro Glu Lys Glu Arg Glu Phe Val
            35                  40                  45

Ala Gly Ser Ser Arg Asp Gly Arg Thr Asn Tyr Tyr Ala Asn Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala His Thr Thr Ser Gly Val Pro Val Trp Glu Arg Ser Tyr Ala
                    100                 105                 110

Tyr Trp Gly Gln Gly Thr Gln Val Thr Val Ser Ser
            115                 120

<210> SEQ ID NO 24
<211> LENGTH: 257
<212> TYPE: PRT
<213> ORGANISM: Artificial Sequence
<220> FEATURE:
<223> OTHER INFORMATION: Polypeptide sequence of anti-TcdA construct
      ID17A

<400> SEQUENCE: 24

Asp Val Gln Leu Gln Glu Ser Gly Gly Gly Leu Val Gln Ala Gly Gly
1               5                   10                  15

Ser Leu Arg Leu Ser Cys Ala Ala Ser Gly Ala Thr Ser Asp Val Tyr
                20                  25                  30

Ala Met Gly Trp Phe Arg Gln Val Pro Gly Lys Glu Arg Glu Phe Val
            35                  40                  45

Ala Thr Ile Asn Arg Ser Gly Ser Asp Ser Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Glu Thr Ala Val Tyr Tyr Cys
                85                  90                  95

Ala Ala Ser Arg Ser Asp Cys Ile Gly Tyr Gly Cys Arg Arg Val Ser
                    100                 105                 110

Gln Asp Tyr Trp Gly Gln Gly Thr Gln Val Thr Val Ser Ser Gly Gly
            115                 120                 125

Gly Gly Ser Gly Gly Gly Gly Ser Gly Gly Gly Gly Ser Gly Gly Gly
        130                 135                 140
```

```
Gly Ser Asp Val Gln Leu Gln Glu Ser Gly Gly Leu Val Gln Ala
145                 150                 155                 160

Gly Gly Ser Leu Arg Leu Ser Cys Val Ile Ser Gly Met Asp Phe Ser
                165                 170                 175

His Lys Pro Ala Gly Trp Phe Arg Gln Ala Pro Gly Lys Glu Arg Glu
            180                 185                 190

Phe Val Ala Ser Ile Thr Thr Arg Ala Ser Thr His Tyr Ala Asp Ser
        195                 200                 205

Val Lys Gly Arg Phe Thr Ile Ser Arg Asp Asn Ala Lys Asn Thr Val
    210                 215                 220

Tyr Leu Glu Met Asn Ser Leu Lys Pro Glu Asp Thr Ala Val Tyr Tyr
225                 230                 235                 240

Cys Asn Ser Glu Tyr Tyr Trp Gly Gln Gly Thr Gln Val Thr Val Ser
                245                 250                 255

Ser

<210> SEQ ID NO 25
<211> LENGTH: 257
<212> TYPE: PRT
<213> ORGANISM: Artificial Sequence
<220> FEATURE:
<223> OTHER INFORMATION: Polypeptide sequence of anti-TcdA construct
      ID29A

<400> SEQUENCE: 25

Asp Val Gln Leu Gln Glu Ser Gly Gly Gly Leu Val Gln Ala Gly Gly
1               5                   10                  15

Ser Leu Arg Leu Ser Cys Ala Ala Ser Gly Ala Thr Ser Asp Val Tyr
            20                  25                  30

Ala Met Gly Trp Phe Arg Gln Val Pro Gly Lys Glu Arg Glu Phe Val
        35                  40                  45

Ala Thr Ile Asn Arg Ser Gly Ser Asp Ser Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Glu Thr Ala Val Tyr Tyr Cys
                85                  90                  95

Ala Ala Ser Arg Ser Asp Cys Ile Gly Tyr Gly Cys His Arg Val Ser
            100                 105                 110

Gln Asp Tyr Trp Gly Gln Gly Thr Gln Val Thr Val Ser Ser Gly Gly
        115                 120                 125

Gly Gly Ser Gly Gly Gly Ser Gly Gly Gly Ser Gly Gly Gly
    130                 135                 140

Gly Ser Asp Val Gln Leu Gln Glu Ser Gly Gly Leu Val Gln Ala
145                 150                 155                 160

Gly Gly Ser Leu Arg Leu Ser Cys Val Ile Ser Gly Met Asp Phe Ser
                165                 170                 175

His Lys Pro Ala Gly Trp Phe Arg Gln Ala Pro Gly Lys Glu Arg Glu
            180                 185                 190

Phe Val Ala Ser Ile Thr Thr Arg Ala Ser Thr His Tyr Ala Asp Ser
        195                 200                 205

Val Lys Gly Arg Phe Thr Ile Ser Arg Asp Asn Ala Lys Asn Thr Val
    210                 215                 220

Tyr Leu Glu Met Asn Ser Leu Lys Pro Glu Asp Thr Ala Val Tyr Tyr
225                 230                 235                 240
```

```
Cys Asn Ser Glu Tyr Tyr Trp Gly Gln Gly Thr Gln Val Thr Val Ser
                245                 250                 255
Ser

<210> SEQ ID NO 26
<211> LENGTH: 15
<212> TYPE: PRT
<213> ORGANISM: Artificial Sequence
<220> FEATURE:
<223> OTHER INFORMATION: Example CDR A

<400> SEQUENCE: 26

Ala Arg Asn Glu Cys Asp Gln Gly His Ile Leu Lys Met Phe Pro
1               5                   10                  15

<210> SEQ ID NO 27
<211> LENGTH: 5
<212> TYPE: PRT
<213> ORGANISM: Artificial Sequence
<220> FEATURE:
<223> OTHER INFORMATION: First third of Example CDR A

<400> SEQUENCE: 27

Ala Arg Asn Glu Cys
1               5

<210> SEQ ID NO 28
<211> LENGTH: 5
<212> TYPE: PRT
<213> ORGANISM: Artificial Sequence
<220> FEATURE:
<223> OTHER INFORMATION: Second third of Example CDR A

<400> SEQUENCE: 28

Asp Gln Gly His Ile
1               5

<210> SEQ ID NO 29
<211> LENGTH: 5
<212> TYPE: PRT
<213> ORGANISM: Artificial Sequence
<220> FEATURE:
<223> OTHER INFORMATION: Third third of Example CDR A

<400> SEQUENCE: 29

Leu Lys Met Phe Pro
1               5

<210> SEQ ID NO 30
<211> LENGTH: 8
<212> TYPE: PRT
<213> ORGANISM: Artificial Sequence
<220> FEATURE:
<223> OTHER INFORMATION: Example CDR B

<400> SEQUENCE: 30

Ala Arg Asn Glu Cys Asp Gln Gly
1               5

<210> SEQ ID NO 31
<211> LENGTH: 4
<212> TYPE: PRT
<213> ORGANISM: Artificial Sequence
<220> FEATURE:
<223> OTHER INFORMATION: Second third of Example CDR B
```

```
<400> SEQUENCE: 31

Asn Glu Cys Asp
1

<210> SEQ ID NO 32
<211> LENGTH: 120
<212> TYPE: PRT
<213> ORGANISM: Artificial Sequence
<220> FEATURE:
<223> OTHER INFORMATION: Polypeptide sequence of anti-IL6R ICVD 7F6

<400> SEQUENCE: 32

Glu Val Gln Leu Val Glu Ser Gly Gly Gly Leu Val Gln Ala Gly Gly
1               5                   10                  15

Ser Thr Arg Leu Thr Cys Leu Ala Ser Gly Ser Ile Ser Ser Ile Asn
            20                  25                  30

Val Ile Gly Trp Tyr Arg Gln Ala Pro Gly Lys Gln Arg Glu Leu Val
        35                  40                  45

Ala Met Ile Gly Arg Gly Glu Gly Ala Asn Tyr Gly Asp Phe Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Lys Pro Glu Asp Thr Ala Val Tyr Tyr Cys Tyr
                85                  90                  95

Ala Asp Tyr Glu Asp Arg Asp Ser Pro Phe Asn Gly Ser Trp Gly Gln
            100                 105                 110

Gly Thr Gln Val Thr Val Ser Ser
        115                 120

<210> SEQ ID NO 33
<211> LENGTH: 120
<212> TYPE: PRT
<213> ORGANISM: Artificial Sequence
<220> FEATURE:
<223> OTHER INFORMATION: Polypeptide sequence of anti-IL6R ICVD ID-3V

<400> SEQUENCE: 33

Glu Val Gln Leu Val Glu Ser Gly Gly Gly Leu Val Gln Ala Gly Gly
1               5                   10                  15

Ser Thr Arg Leu Thr Cys Leu Ala Ser Gly Ser Ile Ser Ser Ile Asn
            20                  25                  30

Val Ile Gly Trp Tyr Arg Gln Ala Pro Gly Lys Gln Arg Glu Leu Val
        35                  40                  45

Ala Met Ile Gly Arg Gly Glu Gly Ala Asn Tyr Gly Asp Phe Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Lys Pro Glu Asp Thr Ala Val Tyr Tyr Cys Tyr
                85                  90                  95

Ala Asp Tyr Glu Asp His Asp Ser Pro Phe Asn Gly Ser Trp Gly Gln
            100                 105                 110

Gly Thr Gln Val Thr Val Ser Ser
        115                 120

<210> SEQ ID NO 34
<211> LENGTH: 123
<212> TYPE: PRT
<213> ORGANISM: Artificial Sequence
<220> FEATURE:
```

```
<223> OTHER INFORMATION: Polypeptide sequence of anti-IL6R ICVD 5G9

<400> SEQUENCE: 34

Glu Val Gln Leu Val Glu Ser Gly Gly Gly Leu Val Gln Ala Gly Gly
1               5                   10                  15

Ser Thr Arg Leu Thr Cys Lys Ala Ser Gly Ser Ile Phe Asn Ile Asn
            20                  25                  30

Ser Ile Asn Val Met Ala Trp Tyr Arg Gln Ala Pro Gly Lys Gln Arg
        35                  40                  45

Glu Leu Val Ala Ile Ile Gly Lys Gly Gly Gly Thr Asn Tyr Ala Asp
    50                  55                  60

Phe Val Lys Gly Arg Phe Thr Ile Ser Arg Asp Ala Ala Lys Asn Thr
65                  70                  75                  80

Val Asn Leu Gln Met Asn Ser Leu Lys Pro Glu Asp Thr Ala Val Tyr
                85                  90                  95

Tyr Cys Tyr Ala Asp Tyr Glu Asp Arg Asp Ser Pro Phe Asn Ala Ser
            100                 105                 110

Trp Gly Gln Gly Thr Gln Val Thr Val Ser Ser
            115                 120

<210> SEQ ID NO 35
<211> LENGTH: 123
<212> TYPE: PRT
<213> ORGANISM: Artificial Sequence
<220> FEATURE:
<223> OTHER INFORMATION: Polypeptide sequence of anti-IL6R ICVD ID-54V

<400> SEQUENCE: 35

Glu Val Gln Leu Val Glu Ser Gly Gly Gly Leu Val Gln Ala Gly Gly
1               5                   10                  15

Ser Thr Arg Leu Thr Cys Lys Ala Ser Gly Ser Ile Phe Asn Ile Asn
            20                  25                  30

Ser Ile Asn Val Met Ala Trp Tyr Arg Gln Ala Pro Gly Lys Gln Arg
        35                  40                  45

Glu Leu Val Ala Ile Ile Gly Lys Gly Gly Gly Thr Asn Tyr Ala Asp
    50                  55                  60

Phe Val Lys Gly Arg Phe Thr Ile Ser Arg Asp Ala Ala Lys Asn Thr
65                  70                  75                  80

Val Asn Leu Gln Met Asn Ser Leu Lys Pro Glu Asp Thr Ala Val Tyr
                85                  90                  95

Tyr Cys Tyr Ala Asp Tyr Glu Asp His Asp Ser Pro Phe Asn Ala Ser
            100                 105                 110

Trp Gly Gln Gly Thr Gln Val Thr Val Ser Ser
            115                 120
```

UNITED STATES PATENT AND TRADEMARK OFFICE
CERTIFICATE OF CORRECTION

PATENT NO. : 12,173,054 B2
APPLICATION NO. : 16/950758
DATED : December 24, 2024
INVENTOR(S) : Crowe et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 689 days.

Signed and Sealed this
Eighth Day of July, 2025

Coke Morgan Stewart
*Acting Director of the United States Patent and Trademark Office*